US008858935B2

(12) United States Patent
Chu

(10) Patent No.: US 8,858,935 B2
(45) Date of Patent: Oct. 14, 2014

(54) COMPOSITIONS AND METHODS FOR INCREASING THE STABILITY OF ANTIBODIES

(75) Inventor: Grace C. Chu, Thousand Oaks, CA (US)

(73) Assignee: Amgen Inc., Thousand Oaks, CA (US)

(*) Notice: Subject to any disclaimer, the term of this patent is extended or adjusted under 35 U.S.C. 154(b) by 987 days.

(21) Appl. No.: 11/437,602

(22) Filed: May 18, 2006

(65) Prior Publication Data

US 2006/0269543 A1    Nov. 30, 2006

Related U.S. Application Data

(60) Provisional application No. 60/683,475, filed on May 19, 2005.

(51) Int. Cl.
A61K 39/395 (2006.01)
C07K 16/00 (2006.01)

(52) U.S. Cl.
CPC ............. C07K 16/00 (2013.01); C07K 2317/41 (2013.01)
USPC .................................... 424/130.1; 424/133.1

(58) Field of Classification Search
None
See application file for complete search history.

(56) References Cited

U.S. PATENT DOCUMENTS

| 4,597,966 | A | 7/1986 | Zolton et al. |
| 5,237,054 | A | 8/1993 | Brinks et al. |
| 5,705,364 | A | 1/1998 | Etcheverry et al. |
| 5,714,350 | A | 2/1998 | Co et al. |
| 5,792,838 | A | 8/1998 | Smith et al. |
| 5,908,826 | A | 6/1999 | Fukuda et al. |
| 6,034,080 | A | 3/2000 | Colaco et al. |
| 6,171,586 | B1 | 1/2001 | Lam et al. |
| 6,267,958 | B1 | 7/2001 | Andya et al. |
| 6,313,102 | B1 | 11/2001 | Colaco et al. |
| 6,485,932 | B1 | 11/2002 | McIntosh et al. |
| 7,335,743 | B2 * | 2/2008 | Welcher et al. ......... 530/388.15 |
| 2003/0113316 | A1 | 6/2003 | Kaisheva et al. |
| 2003/0138417 | A1 | 7/2003 | Kaisheva et al. |
| 2004/0009168 | A1 | 1/2004 | Kaisheva et al. |
| 2004/0018200 | A1 | 1/2004 | Oliver et al. |
| 2004/0033228 | A1 | 2/2004 | Krause et al. |
| 2004/0038878 | A1 | 2/2004 | Tanikawa et al. |
| 2004/0156835 | A1 | 8/2004 | Imoto et al. |
| 2004/0191243 | A1 | 9/2004 | Chen et al. |
| 2004/0208870 | A1 | 10/2004 | Allan |
| 2005/0004353 | A1 | 1/2005 | Welcher et al. |
| 2005/0053598 | A1 | 3/2005 | Burke et al. |
| 2005/0118163 | A1 | 6/2005 | Mizushima et al. |
| 2005/0214278 | A1 | 9/2005 | Kakuta et al. |
| 2006/0194280 | A1 | 8/2006 | Dillon et al. |
| 2007/0020255 | A1 | 1/2007 | Ueno et al. |

FOREIGN PATENT DOCUMENTS

| EP | 0170983 | A2 | 2/1986 |
| EP | 1174148 | A1 | 1/2002 |
| EP | 1 254 666 | | 11/2002 |
| EP | 1 391 209 | | 2/2004 |
| WO | WO 90/07861 | | 7/1990 |
| WO | WO 92/08348 | * | 5/1992 |
| WO | WO 02/30463 | | 4/2002 |
| WO | WO 02/38170 | | 5/2002 |
| WO | WO 02/068455 | | 9/2002 |
| WO | WO 02/096457 | | 12/2002 |
| WO | WO 03/066660 | | 8/2003 |
| WO | WO 03/105894 | | 12/2003 |
| WO | WO 03/106644 | | 12/2003 |
| WO | WO 2004/004639 | | 1/2004 |
| WO | WO 2004/034988 | | 4/2004 |
| WO | WO 2004/035747 | | 4/2004 |
| WO | WO 2004/039337 | | 5/2004 |
| WO | WO 2004/071439 | | 8/2004 |

OTHER PUBLICATIONS

Rudikoff et al ,Proc Natl Acad Sci USA 1982 vol. 79 p. 1979-1983.*
Stark and Heath, "Glucose-Dependent Glycosylation of Secretory Glycoprotein in Mouse Myeloma Cells," Archives of Biochemistry and Biophysics 192(2):599-609, 1979.
Essentials of Glycobiology, Varki et al., eds., Cold Spring Harbor Laboratory Press, New York, 1999, pp. 32-33.
Biochemistry, Lehninger, Worth Publishers, Inc., New York, 1970, pp. 45-46 and 133.
Harris et al., "Commercial Manufacturing Scale Formulation and Analytical Characterization of Therapeutic Recombinant Antibodies," Drug Dev. Res. 61: 137-154, 2004.
Patel et al., "Different culture methods lead to differences in glycosylation of a murine IgG monoclonal antibody," Biochem. J. 285: 839-845, 1992.
Thorens and Vassalli, "Chloroquine and ammonium chloride prevent terminal glycosylation of immunoglobulins in plasma cells without affecting secretion," Nature 321: 618-620, 1986.
Lehninger, Biochemistry, Worth Publishers, Inc., 1970, p. 45.
Marino et al., "Effect of Bench-Scale Culture Conditions on Murine IgG Heterogeneity,", Biotechnol. Bioeng. 54:17-25, 1997.
Chu et al., "Two-Dimension LC/LC/MS Poster for Characterization of Therapeutic Antibodies for Pharmaceutics," poster presented at the American Association of Pharmaceutical Sciences in Boston, Massachusetts, May 16-19, 2004.
Chu et al., "Protein Formulation of an IGG1 Antibody With Atypical Glycosylation: A Study on the Stability of Its Glycoforms," abstract submitted to 229th American Chemical Society National Meeting in San Diego, CA, Mar. 13-17, 2005.
Chu et al., "Protein Formulation of an IGG1 Antibody With Atypical Glycosylation: A Study on the Stability of Its Glycoforms," slide presentation given at Cambridge Healthtech Institute's 2nd Annual Monoclonal Antibodies Advancing Conventional Antibody Development and Production Meeting, May 20, 2005.

(Continued)

Primary Examiner — Yunsoo Kim
(74) Attorney, Agent, or Firm — Rosemary Sweeney

(57) ABSTRACT

The invention encompasses pharmaceutical compositions comprising an antibody and methods of formulating antibodies. The heavy and/or a light chain variable region of the antibody may have certain characteristics. In some embodiments, the antibody may comprise an N-glycan site in a heavy and/or light chain variable region. The compositions may comprise a buffering agent and, optionally, a sugar and/or a salt.

29 Claims, 33 Drawing Sheets

(56) References Cited

OTHER PUBLICATIONS

Chu et al., "Protein Formulation of an IGG1 Antibody With Atypical Glycosylation: A Study on the Stability of Its Glycoforms," poster presented at the American Association of Pharmaceutical Sciences in San Francisco, Jun. 5-8, 2005.

Akers, "Excipient-drug interactions in parenteral formulations," *J. Pharm. Sci.* 91(11):2283-2300, 2002.

Andya et al., "Mechanisms of aggregate formation and carbohydrate excipient stabilization of lyophilized humanized monoclonal antibody formulations," *AAPS PharmSci.* 5(2):1-11, 2003.

Arakawa et al., "Factors affecting short-term and long-term stabilities of proteins," *Adv. Drug Del. Rev.* 10:1-28, 1993.

AVASTIN™ (bevacizumab) United States Package Insert, Genentech, Inc., revised Jan. 2005.

BEXXAR® (tositumomab and Iodine I 131 tositumomab) United States Package Insert, Corixa Corp. and GlaxoSmithKline, issued Jun. 2003.

CAMPATH® (alemtuzumab) United States Package Insert, Millennium and ILEX Partners, LP, issued May 2001, last updated Aug. 30, 2001.

Chen et al., "Influence of histidine on the stability and physical properties of a fully human antibody in aqueous and solid forms," *Pharm. Res.* 20(12):1952-1960, 2003.

Chi et al., "Physical stability of proteins in aqueous solution: mechanism and driving forces in nonnative protein aggregation," *Pharm. Res* 20(9):1325-1336, 2003.

Chirino et al., "Characterizing biological products and assessing comparability following manufacturing changes," *Nat. Biotechnol.* 22(11):1383-1391, 2004.

Cleland et al., "A specific molar ratio of stabilizer to protein is required for storage stability of a lyophilized monoclonal antibody," *J. Pharm. Sci.* 90(3):310-321, 2001.

Coloma et al., "Position effects of variable region carbohydrate on the affinity and in vivo behavior of an anti-(1→6) dextran antibody," *J. Immunol* 162:2162-2170, 1999.

Compton et al., "Micro isoelectric point heterogeneity of a murine monoclonal antibody (L6) originating from cell cultivation conditions," *Biotechnol. Tech.* 3(5):349-354, 1989.

Dillon et al., 9$^{th}$ Symposium on the Interface of Regulatory and Analytical Sciences for Biotechnology Health Products—Abstract L-304-M: "Rapid reversed-phase LC/MS characterization of intact monoclonal antibodies for pharmaceutics," Jan. 2005, Abstract.

Dunn-Walters et al., "Effect of somatic hypermutation on potential N-glycosylation sites in human immunoglobulin heavy chain variable regions," *Mol. Immunol.* 37:107-113, 2000.

ERBITUX™ (cetuximab) United States Package Insert, ImClone Systems Incorporated and Bristol-Myers Squibb Company, 2004.

Fishwild et al., "High-avidity human IgG• monoclonal antibodies from a novel strain of minilocus transgenic mice," *Nat. Biotechnol.* 14:845-851, 1996.

Gala and Morrison, "V region carbohydrate and antibody expression," *J. Immunol.* 172:5489-5494, 2004.

Gupta and Kaisheva, "Development of a multidose formulation for a humanized monoclonal antibody using experimental design techniques," *AAPS PharmSci.* 5(2):1-9, 2003.

Harris et al., "Commercial manufacturing scale formulation and analytical characterization of therapeutic recombinant antibodies," *Drug Dev. Res.* 61:137-154, 2004.

Harris et al., "Identification of multiple sources of charge heterogeneity in a recombinant antibody," *J. Chromatogr. B* 752:233-245, 2001.

HERCEPTIN® (trastuzumab) United States Package Insert, Genentech, Inc., Sep. 1998.

Hermeling et al., "Structure-immunogenicity relationships of therapeutic proteins," *Pharm. Res.* 21(6):897-903, 2004.

Huang et al., "Impact of variable domain glycosylation on antibody clearance: an LC/MS characterization," *Anal. Biochem.* 349:197-207, 2006.

HUMIRA™ (adalimumab) United States Package Insert, Abbott Laboratories, issued Dec. 2002.

Jacquemin et al., "Variable region heavy chain glycosylation determines the anticoagulant activity of a factor VIII antibody,", *J. Thromb. Haemost.* 4:1047-1055, 2006.

Jiskoot et al., "Analytical approaches to the study of monoclonal antibody stability," *Pharm. Res.* 7(12):1234-1241, 1990.

Leibiger et al., "Glycosylation analysis of a polyreactive human monoclonal IgG antibody derived from a human-mouse heterohybridoma," *Mol. Immunol.* 32(8):595-602, 1995.

Leibiger et al., "Variable domain-linked oligosaccharides of a human monoclonal IgG: structure and influence on antigen binding," *Biochem. J.* 338:529-538, 1999.

Manning et al., "Stability of protein pharmaceuticals," *Pharm. Res.* 6(11):903-918, 1989.

Matheus et al., "A critical evaluation of $T_{m(FTIR)}$ measurements of high-concentration IgG, antibody formulations as a formulation development tool," Pharm. Res. 23(7):1617-1627, 2006.

Moran et al., "A systematic approach to the validation of process control parameters for monoclonal antibody production in fed-batch culture of a murine myeloma," *Biotechnol. Bioeng.* 69(3):242-255, 2000.

MYOSCINT® (imciromab pentetate) United States Package Insert, Centocor B.V. revised Oct. 1996.

Penichet and Morrison, "Design and engineering human forms of monoclonal antibodies," Drug Dev. Res. 61:121-136, 2004.

PROSTASCINT™ (capromab pendetide) United States Package Insert, Cytogen Corporation, revised Oct. 28, 1996.

REMICADE® (infliximab) United States Package Insert, Centocor, Inc., revised Feb. 2002.

ReoPro® (abciximab) United States Package Insert, Centocor B.V. and Eli Lilly and Company, revised Nov. 4, 1997.

RITUXAN® (rituximab) United States Package Insert, IDEC Pharmaceuticals Corporation and Genentech, Inc., revised Dec. 20, 2001.

Rudd et al., "Diversification of the IgG molecule by oligosaccharides," *Mol. Immunol.* 28(12):1369-1378, 1991.

Simulect® (basiliximab) United States Package Insert, Novartis Pharmaceuticals Corporation, revised Jan. 2003.

Staby et al., "Comparison of chromatographic ion-exchange resins V. strong and weak cation-exchange resins," *J. Chromatogr. A* 1118:168-179, 2006.

SYNAGIS® (palivizumab) United States Package Insert, MedImmune, Inc. and Abbott Laboratories, Inc. , revised Dec. 2, 1999.

Szenczi et al., "The effect of solvent environment on the conformation and stability of human polyclonal IgG in solution," Biologicals 34:5-14, 2006.

Tachibana et al., "Modified antigen-binding of human antibodies with glycosylation variations of the light chains produced in sugar-limited human hybridoma cultures," *In Vitro Cell Dev. Biol.* 32:178-183, 1996.

Wan et al., "Rapid method for monitoring galactosylation levels during recombinant antibody production by electrospray mass spectrometry with selective-ion monitoring," *J. Chromatogr. A* 913:437-446, 2001.

Wang, "Instability, stabilization, and formulation of liquid protein pharmaceuticals," *Int. J. Pharm.* 185:129-188, 1999.

Weitzhandler et al., "Protein variant separations by cation-exchange chromatography on tentacle-type polymeric stationary phases," *J. Chromatogr. A* 828:365-372, 1998.

Wright and Morrison, "Effect of glycosylation on antibody function: implications for genetic engineering," Trends Biotechnol. 15:26-32, 1997.

Wright et al., "Antibody variable region glycosylation: position effects on antigen binding and carbohydrate structure," EMBO J. 10(10):2717-2723, 1991.

XOLAIR® (omalizumab) United States Package Insert, Genentech, Inc., 2003.

ZENAPAX® (daclizumab) United States Package Insert, Hoffman-La Roche Inc., 1999.

Zhang et al., "Separation and characterization of a monoclonal IgG2 antibody by cation exchange chromatography," BioProcessing J. 2(6):37-43, 2003.

Meeler, A. et al., "Charge Heterogeneity Characterization of a Human Monoclonal Antibody.", 2003.

\* cited by examiner

EVQLVQSGAEVKKPGESLKISCKGSGYSFTSYWIGWVRQMPGKGLEWMG
IIYPGDSDTRYSPSFQGQVTISADKSISTAYLQWSSLKASDTAMYYCAR

Figure 10

EVQLVQSGAEVKKPGESLRISCKGSGYSFTSYWISWVRQMPGKGLEWMGR
IDPSDSYTNYSPSFQGHVTISADKSISTAYLQWSSLKASDTAMYYCAR

Figure 11

EIVLTQSPGTLSLSPGERATLSCRASQSVSSSYLA WYQQKPGQAPRLLIYGASSRAT
GIPDRFSGSGSGTDFTLTISRLEPEDFAVYYCQQYGSSP

```
                         SEQUENCE LISTING

<160> NUMBER OF SEQ ID NOS: 60

<210> SEQ ID NO 1
<211> LENGTH: 990
<212> TYPE: DNA
<213> ORGANISM: Homo sapiens

<400> SEQUENCE: 1
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca cgtgcccag cacctgaact cctggggga      360 ccgtcagtct tcctcttccc cccaaaaccc aaggacaccc tcatgatctc ccggacccct     420
```

```
gaggtcacat gcgtggtggt ggacgtgagc cacgaagacc ctgaggtcaa gttcaactgg      480
tacgtggacg gcgtggaggt gcataatgcc aagacaaagc cgcggggagga gcagtacaac     540 agcacgtacc gtgtggtcag cgtcctcacc gtcctgcacc aggactggct gaatggcaag      600
gagtacaagt gcaaggtctc caacaaagcc ctcccagccc ccatcgagaa aaccatctcc      660
aaagccaaag ggcagccccg agaaccacag gtgtacaccc tgcccccatc ccgggatgag      720
ctgaccaaga accaggtcag cctgacctgc ctggtcaaag gcttctatcc cagcgacatc      780
gccgtggagt gggagagcaa tgggcagccg gagaacaact acaagaccac gcctcccgtg      840
ctggactccg acggctcctt cttcctctat agcaagctca ccgtggacaa gagcaggtgg      900
cagcagggga acgtcttctc atgctccgtg atgcatgagg ctctgcacaa ccactacacg      960
cagaagagcc tctccctgtc tccgggtaaa                                       990
```

```
<210> SEQ ID NO 2
<211> LENGTH: 330
<212> TYPE: PRT
<213> ORGANISM: Homo sapiens

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 3
<211> LENGTH: 321
<212> TYPE: DNA
<213> ORGANISM: Homo sapiens

<400> SEQUENCE: 3
cgaactgtgg ctgcaccatc tgtcttcatc ttcccgccat ctgatgagca gttgaaatct     60
ggaactgcct ctgttgtgtg cctgctgaat aacttctatc ccagagaggc caaagtacag    120
tggaaggtgg ataacgccct ccaatcgggt aactcccagg agagtgtcac agagcaggac    180
agcaaggaca gcacctacag cctcagcagc accctgacgc tgagcaaagc agactacgag    240
aaacacaaag tctacgcctg cgaagtcacc catcagggcc tgagctcgcc cgtcacaaag    300
agcttcaaca ggggagagtg t                                              321

<210> SEQ ID NO 4
<211> LENGTH: 107
<212> TYPE: PRT
<213> ORGANISM: Homo sapiens

<400> SEQUENCE: 4

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 5
<211> LENGTH: 351
<212> TYPE: DNA
<213> ORGANISM: Homo sapiens

<400> SEQUENCE: 5
gaggtgcagc tggtacagtc tggagcagag gtgaaaaagc ccggggagtc tctgaagatc     60
tcctgtaagg gttctggata caactttacc agctactgga tcggctgggt gcgccagatg    120
cccgggaaag gcctggagtt gatggggatc atctatcctg gtgactctga taccagatac    180
agcccgtcct tccaaggcca ggtcaccatc tcagccgaca gtccatcagc caccgcctac    240
ctgcagtgga gcagcctgaa ggcctcggac accgccatgt attactgtgg ttcggggagc    300
``` tactttttact tcgatctctg gggccgtggc accctggtca ccgtctctag t         351

<210> SEQ ID NO 6
<211> LENGTH: 117
<212> TYPE: PRT
<213> ORGANISM: Homo sapiens

<400> SEQUENCE: 6

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Thr Ser Tyr
                20                  25                  30

Trp Ile Gly Trp Val Arg Gln Met Pro Gly Lys Gly Leu Glu Leu Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Gly Ser Gly Ser Tyr Phe Tyr Phe Asp Leu Trp Gly Arg Gly Thr Leu
            100                 105                 110

Val Thr Val Ser Ser
        115

<210> SEQ ID NO 7
<211> LENGTH: 324
<212> TYPE: DNA
<213> ORGANISM: Homo sapiens

<400> SEQUENCE: 7
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatatat ggtgcatcca gcagggccac tggcatccca    180
gacaggttca gtggcagtgg gtctgggaca gacttcactc tcaccatcag cagactggag    240
cctgaagatt ttgcagtgta ttactgtcag cggtctggtg gctcatcatt cactttcggc    300
cctgggacca agtggatat caaa                                            324

<210> SEQ ID NO 8
<211> LENGTH: 108
<212> TYPE: PRT
<213> ORGANISM: Homo sapiens

<400> SEQUENCE: 8

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Arg Ser Gly Gly Ser Ser
                85                  90                  95

Phe Thr Phe Gly Pro Gly Thr Lys Val Asp Ile Lys
            100                 105

<210> SEQ ID NO 9
<211> LENGTH: 351
<212> TYPE: DNA
<213> ORGANISM: Homo sapiens

<400> SEQUENCE: 9
gaggtgcagc tggtgcagtc tggagcagag gtgaaaaagc ccggggagtc tctgaagatc    60
tcctgtaagg gttctggata cagctttacc agctactgga tcggctgggt gcgccagatg   120
cccgggaaag gcctggagtg gatggggatc atctatcctg gtgactctga taccagatac   180
agcccgtcct tccaaggcca ggtcaccatc tcagccgaca gtccatcagc accgcctac    240 ctgcagtgga gcagcctgaa ggcctcggac accgccatgt attactgtgg ttcgggagc    300 tactggtact cgatctctg ggccgtggc accctggtca ccgtctctag t              351

<210> SEQ ID NO 10
<211> LENGTH: 117
<212> TYPE: PRT
<213> ORGANISM: Homo sapiens

<400> SEQUENCE: 10

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Gly Ser Gly Ser Tyr Trp Tyr Phe Asp Leu Trp Gly Arg Gly Thr Leu
            100                 105                 110

Val Thr Val Ser Ser
        115

<210> SEQ ID NO 11
<211> LENGTH: 324
<212> TYPE: DNA
<213> ORGANISM: Homo sapiens

<400> SEQUENCE: 11
gaaattgtgt tgacgcagtc tccaggcacc ctgtctttgt ctccagggga aagagccacc    60
ctctcctgca gggccagtca gagtgttagc agcagctcct tagcctggta ccagcagaaa   120
cctggccagg ctcccaggct cctcatatat ggtgcatcca gcagggccac tggcatccca   180
gacaggttca gtggcagtgg gtctgggaca gacttcactc tcaccatcag cagactggag   240
cctgaagatt ttgcagtgta ttactgtcag cggtctggtg gctcatcatt cactttcggc   300
cctgggacca agtggatat caaa                                            324

<210> SEQ ID NO 12
<211> LENGTH: 108

<212> TYPE: PRT
<213> ORGANISM: Homo sapiens

<400> SEQUENCE: 12

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Ser Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Arg Ser Gly Gly Ser Ser
                85                  90                  95

Phe Thr Phe Gly Pro Gly Thr Lys Val Asp Ile Lys
            100                 105

<210> SEQ ID NO 13
<211> LENGTH: 351
<212> TYPE: DNA
<213> ORGANISM: Homo sapiens

<400> SEQUENCE: 13
gaggtgcagc tggtgcagtc tggagcagag gtgaaaaagc ccggggagtc tctgaagatc     60
tcctgtaagg gttctggata caactttacc agctactgga tcggctgggt gcgccagatg    120
cccgggaaag gcctggagtt gatggggatc atctatcctg gtgactctga taccagatac    180
agcccgtcct tccaaggcca ggtcaccatc tcagccgaca gtccatcag caccgcctac     240
ctgcagtgga gcagcctgaa ggcctcggac accgccatgt attactgtgg ttcggggagc    300
tactggtact tcgatctctg gggccgtggc accctggtca ccgtctctag t             351

<210> SEQ ID NO 14
<211> LENGTH: 117
<212> TYPE: PRT
<213> ORGANISM: Homo sapiens

<400> SEQUENCE: 14

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Thr Ser Tyr
            20                  25                  30

Trp Ile Gly Trp Val Arg Gln Met Pro Gly Lys Gly Leu Glu Leu Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Gly Ser Gly Ser Tyr Trp Tyr Phe Asp Leu Trp Gly Arg Gly Thr Leu
            100                 105                 110

Val Thr Val Ser Ser
            115

<210> SEQ ID NO 15
<211> LENGTH: 324
<212> TYPE: DNA
<213> ORGANISM: Homo sapiens

<400> SEQUENCE: 15

```
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatatat ggtgcatcca gcagggccac tggcatccca     180
gacaggttca gtggcagtgg gtctgggaca gacttcactc tcaccatcag cagactggag     240
cctgaagatt ttgcagtgta ttactgtcag cggtctggtg ctcatcatt cactttcggc     300 cctgggacca agtggatat caaa                                              324
```

<210> SEQ ID NO 16
<211> LENGTH: 108
<212> TYPE: PRT
<213> ORGANISM: Homo sapiens

<400> SEQUENCE: 16

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Arg Ser Gly Gly Ser Ser
                85                  90                  95

Phe Thr Phe Gly Pro Gly Thr Lys Val Asp Ile Lys
            100                 105

<210> SEQ ID NO 17
<211> LENGTH: 447
<212> TYPE: PRT
<213> ORGANISM: Homo sapiens

<400> SEQUENCE: 17

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Thr Ser Tyr
            20                  25                  30

Trp Ile Gly Trp Val Arg Gln Met Pro Gly Lys Gly Leu Glu Leu Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Gly Ser Gly Ser Tyr Phe Tyr Phe Asp Leu Trp Gly Arg Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 18
<211> LENGTH: 215
<212> TYPE: PRT
<213> ORGANISM: Homo sapiens

<400> SEQUENCE: 18

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser

```
                 50                  55                  60
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Arg Ser Gly Ser Ser
                 85                  90                  95

Phe Thr Phe Gly Pro Gly Thr Lys Val Asp Ile Lys Arg Thr Val Ala
                100                 105                 110

Ala Pro Ser Val Phe Ile Phe Pro Pro Ser Asp Glu Gln Leu Lys Ser
                115                 120                 125

Gly Thr Ala Ser Val Val Cys Leu Leu Asn Asn Phe Tyr Pro Arg Glu
                130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
                210                 215

<210> SEQ ID NO 19
<211> LENGTH: 447
<212> TYPE: PRT
<213> ORGANISM: Homo sapiens

<400> SEQUENCE: 19

Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Ser Tyr
                 20                  25                  30

Trp Ile Gly Trp Val Arg Gln Met Pro Gly Lys Gly Leu Glu Trp Met
                 35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Gly Ser Gly Ser Tyr Trp Tyr Phe Asp Leu Trp Gly Arg Gly Thr Leu
                100                 105                 110

Val Thr Val Ser Ser Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
                130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205
```

-continued

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 20
<211> LENGTH: 215
<212> TYPE: PRT
<213> ORGANISM: Homo sapiens

<400> SEQUENCE: 20

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Ser Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Arg Ser Gly Gly Ser Ser
                85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

```
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 21
<211> LENGTH: 447
<212> TYPE: PRT
<213> ORGANISM: Homo sapiens

<400> SEQUENCE: 21

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Gly Ser Gly Ser Tyr Trp Tyr Phe Asp Leu Trp Gly Arg Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
```

```
                    290                 295                 300
Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 22
<211> LENGTH: 215
<212> TYPE: PRT
<213> ORGANISM: Homo sapiens

<400> SEQUENCE: 22

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Arg Ser Gly Gly Ser Ser
                85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 23
<211> LENGTH: 24
<212> TYPE: DNA
<213> ORGANISM: Artificial
<220> FEATURE:
<223> OTHER INFORMATION: oligonucleotide primer for PCR
<220> FEATURE:
<221> NAME/KEY: misc_feature
<222> LOCATION: (18)..(23)
<223> OTHER INFORMATION: n is a, c, t, or g

<400> SEQUENCE: 23
ggccggatag gcctccannn nnnt                                          24

<210> SEQ ID NO 24
<211> LENGTH: 21
<212> TYPE: DNA
<213> ORGANISM: Artificial
<220> FEATURE:
<223> OTHER INFORMATION: oligonucleotide primer for PCR

<400> SEQUENCE: 24
ggggtcaggc tggaactgag g                                             21

<210> SEQ ID NO 25
<211> LENGTH: 19
<212> TYPE: DNA
<213> ORGANISM: Artificial
<220> FEATURE:
<223> OTHER INFORMATION: oligonucleotide primer for PCR

<400> SEQUENCE: 25
tgaggacgct gaccacacg                                                19

<210> SEQ ID NO 26
<211> LENGTH: 48
<212> TYPE: DNA
<213> ORGANISM: Artificial
<220> FEATURE:
<223> OTHER INFORMATION: oligonucleotide primer for PCR

<400> SEQUENCE: 26
acaacaaagc ttctagacca ccatggaaac cccagctcag cttctctt                48

<210> SEQ ID NO 27
<211> LENGTH: 33
<212> TYPE: DNA
<213> ORGANISM: Artificial
<220> FEATURE:
<223> OTHER INFORMATION: oligonucleotide primer for PCR

<400> SEQUENCE: 27
cttgtcgact caacactctc ccctgttgaa gct                                33

<210> SEQ ID NO 28
<211> LENGTH: 44
<212> TYPE: DNA
<213> ORGANISM: Artificial
<220> FEATURE:
<223> OTHER INFORMATION: oligonucleotide primer for PCR

<400> SEQUENCE: 28
cagcagaagc ttctagacca ccatggggtc aaccgccatc ctcg                    44

<210> SEQ ID NO 29
<211> LENGTH: 42

```
<212> TYPE: DNA
<213> ORGANISM: Artificial
<220> FEATURE:
<223> OTHER INFORMATION: oligonucleotide primer for PCR

<400> SEQUENCE: 29
cttggtggag gcactagaga cggtgaccag ggtgccacgg cc                    42

<210> SEQ ID NO 30
<211> LENGTH: 117
<212> TYPE: PRT
<213> ORGANISM: Homo sapiens

<400> SEQUENCE: 30
```

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Gly Ser Gly Ser Tyr Trp Tyr Phe Asp Leu Arg Gly Arg Gly Thr Leu
            100                 105                 110

Val Thr Val Ser Ser
        115

```
<210> SEQ ID NO 31
<211> LENGTH: 109
<212> TYPE: PRT
<213> ORGANISM: Homo sapiens

<400> SEQUENCE: 31
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ile Ser Ser
            20                  25                  30

Tyr Leu Ala Trp Tyr Gln Gln Lys Pro Gly Gln Thr Pro Arg Leu Leu
        35                  40                  45

Ile Tyr Gly Val Ser Ser Arg Ala Thr Gly Ile Pro Asp Arg Phe Ser
    50                  55                  60

Gly Ser Gly Ser Gly Thr Asp Phe Thr Leu Thr Ile Thr Arg Leu Glu
65                  70                  75                  80

Pro Glu Asp Phe Ala Val Tyr Tyr Cys Gln Gln Tyr Gly Asn Ser Phe
                85                  90                  95

Met Tyr Thr Phe Gly Gln Gly Thr Lys Leu Glu Ile Lys
            100                 105

```
<210> SEQ ID NO 32
<211> LENGTH: 447
<212> TYPE: PRT
<213> ORGANISM: Homo sapiens

<400> SEQUENCE: 32
```

Glu Val Gln Leu Val Gln Ser Gly Ala Glu Val Lys Lys Pro Gly Glu

```
1               5                   10                  15
Ser Leu Lys Ile Ser Cys Lys Gly Ser Gly Tyr Ser Phe Thr Ser Tyr
            20                  25                  30
Trp Ile Gly Trp Val Arg Gln Met Pro Gly Lys Gly Leu Glu Trp Met
            35                  40                  45
Gly Ile Ile Tyr Pro Gly Asp Ser Asp Thr Arg Tyr Ser Pro Ser Phe
            50                  55                  60
Gln Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Gly Ser Gly Ser Tyr Trp Tyr Phe Asp Leu Arg Gly Arg Gly Thr Leu
                100                 105                 110
Val Thr Val Ser Ser Ala Ser Thr Lys Gly Pro Ser Val Phe Pro Leu
                115                 120                 125
Ala Pro Ser Ser Lys Ser Thr Ser Gly Gly Thr Ala Ala Leu Gly Cys
                130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
                180                 185                 190
Leu Gly Thr Gln Thr Tyr Ile Cys Asn Val Asn His Lys Pro Ser Asn
                195                 200                 205
Thr Lys Val Asp Lys Lys Val Glu Pro Lys Ser Cys Asp Lys Thr His
210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
                260                 265                 270
Val Lys Phe Asn Trp Tyr Val Asp Gly Val Glu Val His Asn Ala Lys
                275                 280                 285
Thr Lys Pro Arg Glu Glu Gln Tyr Asn Ser Thr Tyr Arg Val Val Ser
                290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
                340                 345                 350
Pro Ser Arg Asp Glu Leu Thr Lys Asn Gln Val Ser Leu Thr Cys Leu
                355                 360                 365
Val Lys Gly Phe Tyr Pro Ser Asp Ile Ala Val Glu Trp Glu Ser Asn
                370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
                420                 425                 430
```

His Asn His Tyr Thr Gln Lys Ser Leu Ser Leu Ser Pro Gly Lys
        435                 440                 445

<210> SEQ ID NO 33
<211> LENGTH: 216
<212> TYPE: PRT
<213> ORGANISM: Homo sapiens

<400> SEQUENCE: 33

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ile Ser Ser
            20                  25                  30

Tyr Leu Ala Trp Tyr Gln Gln Lys Pro Gly Gln Thr Pro Arg Leu Leu
        35                  40                  45

Ile Tyr Gly Val Ser Ser Arg Ala Thr Gly Ile Pro Asp Arg Phe Ser
    50                  55                  60

Gly Ser Gly Ser Gly Thr Asp Phe Thr Leu Thr Ile Thr Arg Leu Glu
65                  70                  75                  80

Pro Glu Asp Phe Ala Val Tyr Tyr Cys Gln Gln Tyr Gly Asn Ser Phe
                85                  90                  95

Met Tyr Thr Phe Gly Gln Gly Thr Lys Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 34
<211> LENGTH: 5
<212> TYPE: PRT
<213> ORGANISM: Homo sapiens

<400> SEQUENCE: 34

Ser Tyr Trp Ile Gly
1               5

<210> SEQ ID NO 35
<211> LENGTH: 17
<212> TYPE: PRT
<213> ORGANISM: Homo sapiens

<400> SEQUENCE: 35

Ile Ile Tyr Pro Gly Asp Ser Asp Thr Arg Tyr Ser Pro Ser Phe Gln
1               5                   10                  15

Gly

<210> SEQ ID NO 36
<211> LENGTH: 8
<212> TYPE: PRT
<213> ORGANISM: Homo sapiens

<400> SEQUENCE: 36

Gly Ser Tyr Phe Tyr Phe Asp Leu
1               5

<210> SEQ ID NO 37
<211> LENGTH: 8
<212> TYPE: PRT
<213> ORGANISM: Homo sapiens

<400> SEQUENCE: 37

Gly Ser Tyr Trp Tyr Phe Asp Leu
1               5

<210> SEQ ID NO 38
<211> LENGTH: 12
<212> TYPE: PRT
<213> ORGANISM: Homo sapiens

<400> SEQUENCE: 38

Arg Ala Ser Gln Ser Val Ser Ser Ser Tyr Leu Ala
1               5                   10

<210> SEQ ID NO 39
<211> LENGTH: 12
<212> TYPE: PRT
<213> ORGANISM: Homo sapiens

<400> SEQUENCE: 39

Arg Ala Ser Gln Ser Val Ser Ser Ser Leu Ala
1               5                   10

<210> SEQ ID NO 40
<211> LENGTH: 12
<212> TYPE: PRT
<213> ORGANISM: Homo sapiens

<400> SEQUENCE: 40

Arg Ala Ser Gln Ser Ile Ile Ser Ser Tyr Leu Ala
1               5                   10

<210> SEQ ID NO 41
<211> LENGTH: 7
<212> TYPE: PRT
<213> ORGANISM: Homo sapiens

<400> SEQUENCE: 41

Gly Ala Ser Ser Arg Ala Thr
1               5

<210> SEQ ID NO 42
<211> LENGTH: 7
<212> TYPE: PRT
<213> ORGANISM: Homo sapiens

<400> SEQUENCE: 42

Gly Val Ser Ser Arg Ala Thr
1               5

<210> SEQ ID NO 43
<211> LENGTH: 9

```
<212> TYPE: PRT
<213> ORGANISM: Homo sapiens

<400> SEQUENCE: 43

Gln Arg Ser Gly Gly Ser Ser Phe Thr
1               5

<210> SEQ ID NO 44
<211> LENGTH: 10
<212> TYPE: PRT
<213> ORGANISM: Homo sapiens

<400> SEQUENCE: 44

Gln Gln Tyr Gly Asn Ser Phe Met Tyr Thr
1               5                   10

<210> SEQ ID NO 45
<211> LENGTH: 24
<212> TYPE: DNA
<213> ORGANISM: Homo sapiens

<400> SEQUENCE: 45
gggagctact tttacttcga tctc                                          24

<210> SEQ ID NO 46
<211> LENGTH: 24
<212> TYPE: DNA
<213> ORGANISM: Homo sapiens

<400> SEQUENCE: 46
gggagctact ggtacttcga tctc                                          24

<210> SEQ ID NO 47
<211> LENGTH: 27
<212> TYPE: DNA
<213> ORGANISM: Homo sapiens

<400> SEQUENCE: 47
cagcggtctg gtggctcatc attcact                                       27

<210> SEQ ID NO 48
<211> LENGTH: 9
<212> TYPE: PRT
<213> ORGANISM: Homo sapiens
<220> FEATURE:
<221> NAME/KEY: Unsure
<222> LOCATION: (2)..(9)
<223> OTHER INFORMATION: x is any amino acid

<400> SEQUENCE: 48

Cys Xaa Xaa Xaa Xaa Xaa Xaa Xaa Xaa
1               5

<210> SEQ ID NO 49
<211> LENGTH: 5
<212> TYPE: PRT
<213> ORGANISM: Homo sapiens

<400> SEQUENCE: 49

Leu Glu Trp Ile Gly
1               5

<210> SEQ ID NO 50
<211> LENGTH: 4
<212> TYPE: PRT
```

```
<213> ORGANISM: Homo sapiens
<220> FEATURE:
<221> NAME/KEY: UNSURE
<222> LOCATION: (3)..(3)
<223> OTHER INFORMATION: x is any amino acid

<400> SEQUENCE: 50

Trp Gly Xaa Gly
1

<210> SEQ ID NO 51
<211> LENGTH: 4
<212> TYPE: PRT
<213> ORGANISM: Homo sapiens
<220> FEATURE:
<221> NAME/KEY: UNSURE
<222> LOCATION: (3)..(3)
<223> OTHER INFORMATION: x is any amino acid

<400> SEQUENCE: 51

Phe Gly Xaa Gly
1

<210> SEQ ID NO 52
<211> LENGTH: 20
<212> TYPE: PRT
<213> ORGANISM: Homo sapiens

<400> SEQUENCE: 52

Met Glu Thr Asp Thr Leu Leu Leu Trp Val Leu Leu Trp Val Pro
1               5                   10                  15

Gly Ser Thr Gly
            20

<210> SEQ ID NO 53
<211> LENGTH: 26
<212> TYPE: PRT
<213> ORGANISM: Homo sapiens

<400> SEQUENCE: 53

Met Ala Thr Gly Ser Arg Thr Ser Leu Leu Leu Ala Phe Gly Leu Leu
1               5                   10                  15

Cys Leu Pro Trp Leu Gln Glu Gly Ser Ala
            20                  25

<210> SEQ ID NO 54
<211> LENGTH: 19
<212> TYPE: PRT
<213> ORGANISM: Homo sapiens

<400> SEQUENCE: 54

Met Gly Ser Thr Ala Ile Leu Ala Leu Leu Leu Ala Val Leu Gln Gly
1               5                   10                  15

Val Cys Ala

<210> SEQ ID NO 55
<211> LENGTH: 20
<212> TYPE: PRT
<213> ORGANISM: Homo sapiens

<400> SEQUENCE: 55

Met Glu Thr Pro Ala Gln Leu Leu Phe Leu Leu Leu Leu Trp Leu Pro
1               5                   10                  15

Asp Thr Thr Gly
```

<210> SEQ ID NO 56
<211> LENGTH: 351
<212> TYPE: DNA
<213> ORGANISM: Homo sapiens

<400> SEQUENCE: 56
gaggtgcagc tggtgcagtc tggagcagag gtgaaaaagc ccggggagtc tctgaagatc     60
tcctgtaagg gttctggata cagctttacc agctactgga tcggctgggt gcgccagatg    120
cccgggaaag gcctggagtg gatggggatc atctatcctg gtgactctga taccagatac    180
agcccgtcct tccaaggcca ggtcaccatc tcagccgaca gtccatcag caccgcctac     240 ctgcagtgga gcagcctgaa ggcctcggac accgccatgt attactgtgg ttcggggagc    300
tactggtact cgatctccg gggccgtggc accctggtca ccgtctctag t              351

<210> SEQ ID NO 57
<211> LENGTH: 327
<212> TYPE: DNA
<213> ORGANISM: Homo sapiens

<400> SEQUENCE: 57
gaaattgtgt tgacgcagtc tccaggcacc ctgtctttgt ctccagggga aagagccacc     60
ctctcctgca gggccagtca gagtattatc agcagctact tagcctggta ccagcagaaa    120
cctggccaga ctcccaggct cctcatctat ggtgtatcca gcagggccac tggcatccca    180
gacaggttca gtggcagtgg gtctgggaca gacttcactc tcaccatcac cagactggag    240
cctgaagatt ttgcagtgta ttactgtcag cagtatggta actcatttat gtacactttt    300
ggccagggga ccaagctgga gatcaaa                                        327

<210> SEQ ID NO 58
<211> LENGTH: 98
<212> TYPE: PRT
<213> ORGANISM: Homo sapiens

<400> SEQUENCE: 58

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg

<210> SEQ ID NO 59
<211> LENGTH: 98
<212> TYPE: PRT
<213> ORGANISM: Homo sapiens

<400> SEQUENCE: 59

Glu Val Gln Leu Val Gln Ser Gly Ala Glu Val Lys Lys Pro Gly Glu

```
1               5                   10                  15
Ser Leu Arg Ile Ser Cys Lys Gly Ser Gly Tyr Ser Phe Thr Ser Tyr
                20                  25                  30

Trp Ile Ser Trp Val Arg Gln Met Pro Gly Lys Gly Leu Glu Trp Met
                35                  40                  45

Gly Arg Ile Asp Pro Ser Asp Ser Tyr Thr Asn Tyr Ser Pro Ser Phe
                50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg

<210> SEQ ID NO 60
<211> LENGTH: 96
<212> TYPE: PRT
<213> ORGANISM: Homo sapiens

<400> SEQUENCE: 60

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
                35                  40                  45

Ile Tyr Gly Ala Ser Ser Arg Ala Thr Gly Ile Pro Asp Arg Phe Ser
                50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95
```

COMPOSITIONS AND METHODS FOR INCREASING THE STABILITY OF ANTIBODIES

CROSS-REFERENCE TO RELATED APPLICATION

This application claims the benefit under 35 U.S.C. §119 (e) of U.S. Provisional Application Ser. No. 60/683,475 filed May 19, 2005, which is incorporated herein by reference in its entirety.

FIELD

The invention is in the field of methods and compositions for stabilizing antibodies.

BACKGROUND

In the many applications in which antibodies are used, it is desirable to formulate antibodies such that their physical structure and biological activity are stably maintained over a span of time. Current uses of antibodies include broad research use and use as human therapeutics and diagnostics, among many other uses. Antibodies, as a class of proteins, share many similarities, but different antibodies do possess different physical structures and biological activities. Preparations of a single antibody may be heterogeneous due to differences in, for example, glycosylation, amino acid modification, or tertiary structure. The present invention is directed toward compositions and methods for stabilizing a particular group of antibodies and methods of using such compositions to treat various diseases.

SUMMARY

The invention encompasses stable compositions comprising antibodies and methods for stabilizing antibodies. In particular embodiments, the compositions can comprise antibodies from among disclosed groups of antibodies, and compositions having a pH within certain ranges and/or comprising a particular buffering agent, such as, for example, histidine, sodium acetate, or sodium citrate. In other embodiments, the invention provides compositions including a purified preparation of a monoclonal antibody that comprises plural structural variants, for example, a preparation comprising at least 2, 3, 4, or 5 different isoforms of an antibody. The invention further encompasses methods of stabilizing antibodies, optionally purified preparations of monoclonal antibodies comprising plural structural variants. The structural variants may be isoforms due to heterogeneous sialylation of an N-glycan attached to a variable region of the antibody. The structural variants may be isoforms due to heterogeneous sialylation of any glycan attached to an antibody.

In one aspect, the invention includes stable pharmaceutical composition having a pH from about pH 5.5 to about pH 6.5 comprising a purified preparation of a monoclonal antibody and histidine, sodium acetate, or sodium citrate, wherein the antibody has at least one characteristic selected from the group of characteristics consisting of: (a) the antibody comprises a heavy chain variable region at least about 80%, 85%, 90%, 95%, 98%, or 100% identical to SEQ ID NO:6, SEQ ID NO:10, SEQ ID NO:14, or SEQ ID NO:30; (b) the antibody comprises a light chain variable region at least about 80%, 85%, 90%, 95%, 98% or 100% identical to SEQ ID NO:8, SEQ ID NO:12, SEQ ID NO:16, or SEQ ID NO:31; (c) the antibody comprises a heavy chain variable region which includes an N-glycan site; (d) the antibody comprises a light chain variable region which includes an N-glycan site; (e) the antibody comprises a heavy chain variable region including a heavy chain CDR3 having an amino acid sequence selected from the group consisting of (i) an amino acid sequence comprising at least 7 of the amino acids of SEQ ID NO:36 in the same order and spacing as they occur in SEQ ID NO:36 and (ii) an amino acid sequence comprising SEQ ID NO:37; (f) the antibody comprises a light chain variable region including a light chain CDR3 having an amino acid sequence selected from the group consisting of (i) SEQ ID NO:43 and (ii) SEQ ID NO:44; (g) the antibody comprises a heavy chain variable region at least about 80%, 85% or 90% identical to that encoded by human genomic $V_H$ segment 5-51 (SEQ ID NO:58) or 5-a (SEQ ID NO:59); and (h) the antibody comprises a light chain variable region at least about 80%, 85% or 90% identical to that encoded by human genomic $V_L$ segment VKIII/A27 (SEQ ID NO:60). In a further aspect, the antibody can comprise a heavy chain variable region including: a CDR1 comprising SEQ ID NO:34; a CDR2 comprising SEQ ID NO:35; and a CDR3 comprising SEQ ID NO:36 or SEQ ID NO:37. In still another aspect, the antibody can comprise a light chain variable region including: a CDR1 comprising SEQ ID NO:38, SEQ ID NO:39, or SEQ ID NO:40; a CDR2 comprising SEQ ID NO:41 or SEQ ID NO:42; and a CDR3 comprising SEQ ID NO:43 or SEQ ID NO:44. In some embodiments, the heavy variable region may comprise the following sequences: a CDR1 comprising at least 4 of the amino acids of SEQ ID NO:34 in the same order and spacing as they occur in SEQ ID NO:34; a CDR2 comprising at least 10, 11, 12, 13, 14, or 15 of the amino acids of SEQ ID NO:35 in the same order and spacing as they occur in SEQ ID NO:35; a CDR3 comprising at least 5, 6, or 7 of the amino acids of SEQ ID NO:36 or SEQ ID NO:37 in the same order and spacing as they occur in SEQ ID NO:36 or SEQ ID NO:37. In some embodiments, the light variable region may comprise the following sequences: a CDR1 comprising at least 9, 10, or 11 of the amino acids of SEQ ID NO:38, SEQ ID NO:39, or SEQ ID NO:40 in the same order and spacing as they occur in SEQ ID NO:38, SEQ ID NO:39, or SEQ ID NO:40; a CDR2 comprising at least 4, 5, or 6 of the amino acids of SEQ ID NO:41 or SEQ ID NO:42 in the same order and spacing as they occur in SEQ ID NO:41 or SEQ ID NO:42; a CDR3 comprising at least 7, 8, or 9 of the amino acids of SEQ ID NO:43 or SEQ ID NO:44 in the same order and spacing as they occur in SEQ ID NO:43 or SEQ ID NO:44. The monoclonal antibody can be an IgG antibody, such as, for example, an IgG1, an IgG2, and IgG3, or an IgG4 antibody. The composition may comprise a sugar, such as sorbitol or sucrose, and/or a salt. The pH of the composition can be from about 5.7 to about 6.3 or can be about 6.0. The antibody may be a human or humanized antibody and may bind to interferon gamma (IFN-γ).

The invention provides a pharmaceutical composition comprising a purified preparation of a monoclonal antibody and a buffering agent, wherein the composition is at a pH from about 5.5 to about 6.5 and wherein the purified preparation comprises at least three different isoforms of the antibody. The pH of the composition can be from about 5.7 to about 6.3 or can be about 6.0, and the composition can be a liquid. The antibody can comprise an N-glycan site in a heavy and/or a light chain variable region and can have a heavy chain variable region at least 80%, 90%, 95%, 98%, or 100% identical to SEQ ID NO:6, SEQ ID NO:10, SEQ ID NO:14, or SEQ ID NO:30 and/or a light chain variable region is at least 80%, 90%, 95%, 98%, or 100% identical to SEQ ID NO:8, SEQ ID NO:12, SEQ ID NO:16, or SEQ ID NO:31. The antibody can comprise: a heavy chain variable region including a CDR1 comprising SEQ ID NO:34, a CDR2 comprising SEQ ID NO:35, and a CDR3 comprising SEQ ID NO:36 or SEQ ID NO:37; and/or a light chain variable region including a CDR1 comprising SEQ ID NO:38, SEQ ID NO:39, or SEQ ID NO:40, a CDR2 comprising SEQ ID NO:41 or SEQ ID NO:42, and a CDR3 comprising SEQ ID NO:43 or SEQ ID NO:44. The buffering agent can be histidine, sodium acetate, sodium phosphate, potassium phosphate, or sodium citrate, and the composition can further comprise a sugar, such as, for example, sorbitol, a carbohydrate, and/or a salt. The antibody can be produced in a CHO cell. The antibody can a human or humanized IgG antibody, optionally an IgG1, IgG2, IgG3, or IgG4 antibody. The antibody may bind to interferon gamma, optionally human interferon gamma. At least 90% or 95% of the detectable protein in the purified preparation can be in the monomer peak as assessed by size exclusion chromatography (SEC).

Further, the invention provides a method for stabilizing a purified preparation of a monoclonal antibody comprising formulating the purified preparation in a composition comprising a buffering agent, wherein the composition has a pH from about 5.5 to about 6.5 and wherein the purified preparation comprises at least three different isoforms of the antibody. The antibody can have an N-glycan site in a heavy and/or a light chain variable region. The heavy chain variable region of the antibody can be at least 80%, 90%, 95%, 98%, or 100% identical to SEQ ID NO:6, SEQ ID NO:10, SEQ ID NO:14, or SEQ ID NO:30 and/or the light chain variable region of the antibody can be at least 80%, 90%, 95%, 98%, or 100% identical to SEQ ID NO:8, SEQ ID NO:12, SEQ ID NO:16, or SEQ ID NO:31. The antibody can comprise: a heavy chain variable region including a CDR1 comprising SEQ ID NO:34, a CDR2 comprising SEQ ID NO:35, and a CDR3 comprising SEQ ID NO:36 or SEQ ID NO:37; and/or a light chain variable region including a CDR1 comprising SEQ ID NO:38, SEQ ID NO:39, or SEQ ID NO:40, a CDR2 comprising SEQ ID NO:41 or SEQ ID NO:42, and a CDR3 comprising SEQ ID NO:43 or SEQ ID NO:44. The buffering agent can be histidine, sodium acetate, sodium phosphate, potassium phosphate, or sodium citrate. The composition can further comprise a sugar, such as, for example, sorbitol, a carbohydrate, and/or a salt. The antibody can be made in a CHO cell and can be an IgG antibody, optionally and IgG1, IgG2, IgG3, or IgG4. The antibody can be human or humanized. The pH of the composition can be from about 5.7 to about 6.3 or about 6.0. At least 90% or 95% of the detectable protein in the purified preparation can be in the monomer peak as assessed by size exclusion chromatography (SEC).

In another embodiment, the invention includes a composition comprising histidine and a purified preparation of a monoclonal antibody, wherein the purified preparation comprises at least three isoforms of the antibody and wherein the pH of the composition is from about 5 to about 7. Alternatively, the composition can comprise sodium acetate and a purified preparation of a monoclonal antibody, wherein the purified preparation comprises at least three isoforms of the antibody and wherein the pH of the composition is from about 5 to about 6. The antibody can comprise an N-glycan site in a heavy and/or a light chain variable region and can comprise a heavy chain variable region at least 80%, 90%, 95%, 98%, or 100% identical to SEQ ID NO:6, SEQ ID NO:10, SEQ ID NO:14, or SEQ ID NO:30 and/or a light chain variable region at least 80%, 90%, 95%, 98%, or 100% identical to SEQ ID NO:8, SEQ ID NO:12, SEQ ID NO:16, or SEQ ID NO:31. The antibody can comprise: a heavy chain variable region including a CDR1 comprising SEQ ID NO:34, a CDR2 comprising SEQ ID NO:35, and a CDR3 comprising SEQ ID NO:36 or SEQ ID NO:37; and/or a light chain variable region including a CDR1 comprising SEQ ID NO:38, SEQ ID NO:39, or SEQ ID NO:40, a CDR2 comprising SEQ ID NO:41 or SEQ ID NO:42, and a CDR3 comprising SEQ ID NO:43 or SEQ ID NO:44. The composition can further comprise a sugar, such as, for example, sorbitol, a carbohydrate, and/or a salt. The antibody can be made in a CHO cell and can be an IgG antibody, optionally and IgG1, IgG2, IgG3, or IgG4. The antibody can be human or humanized. The pH of the composition can be from about 5.5 to about 6.5, from about 5.7 to about 6.3, or about 6.0. The composition may be a liquid or may be frozen or lyophilized. The composition can further comprise a sugar, such as, for example, sorbitol, a carbohydrate, and/or a salt. At least 90% or 95% of the detectable protein in the purified preparation can be in the monomer peak as assessed by size exclusion chromatography (SEC).

In another embodiment, the invention comprises a method for stabilizing a purified preparation of a monoclonal antibody comprising formulating the antibody in a composition comprising histidine, wherein the purified preparation comprises at least three isoforms of the antibody, and wherein the pH of the composition is from about 5 to about 7. Alternatively, the composition can comprise sodium acetate and a purified preparation of a monoclonal antibody, wherein the purified preparation comprises at least three isoforms of the antibody, and wherein the pH of the composition is from about 5 to about 6. The composition can further comprise a sugar, such as, for example, sorbitol, a carbohydrate, and/or a salt. The antibody can comprise a heavy chain variable region at least 80%, 90%, 95%, 98%, or 100% identical to SEQ ID NO:6, SEQ ID NO:10, SEQ ID NO:14, or SEQ ID NO:30 and/or a light chain variable region at least 80%, 90%, 95%, 98%, or 100% identical to SEQ ID NO:8, SEQ ID NO:12, SEQ ID NO:16, or SEQ ID NO:31. The antibody can comprise: a heavy chain variable region including a CDR1 comprising SEQ ID NO:34, a CDR2 comprising SEQ ID NO:35, and a CDR3 comprising SEQ ID NO:36 or SEQ ID NO:37; and/or a light chain variable region including a CDR1 comprising SEQ ID NO:38, SEQ ID NO:39, or SEQ ID NO:40, a CDR2 comprising SEQ ID NO:41 or SEQ ID NO:42, and a CDR3 comprising SEQ ID NO:43 or SEQ ID NO:44. At least 90% or 95% of the detectable protein in the purified preparation can be in the monomer peak as assessed by size exclusion chromatography (SEC).

The invention also includes a pharmaceutical composition comprising a purified preparation of a monoclonal antibody and histidine, wherein the pharmaceutical composition has a pH from about 5 to about 7 or has a pH of about 6. The purified preparation can comprise at least 3 isoforms of the antibody. The antibody can comprise a heavy chain variable region at least about 80%, 85%, 90%, 95%, or 100% identical to the amino acid sequence of SEQ ID NO:6, SEQ ID NO:10, SEQ ID NO:14, or SEQ ID NO:30 and/or a light chain variable region at least about 80%, 85%, 90%, 95%, or 100% identical to the amino acid sequence of SEQ ID NO:8, SEQ ID NO:12, SEQ ID NO:16, or SEQ ID NO:31 The composition can also comprise sorbitol.

The invention further includes a pharmaceutical composition comprising a purified preparation of a monoclonal antibody and sodium acetate, sodium phosphate, or potassium phosphate, wherein the pharmaceutical composition has a pH from about 5 to about 6 or has a pH of about 6. The purified preparation can comprise at least 3 isoforms of the antibody. The antibody can comprise a heavy chain variable region at least about 80%, 85%, 90%, 95%, or 100% identical to the amino acid sequence of SEQ ID NO:6, SEQ ID NO:10, SEQ ID NO:14, or SEQ ID NO:30 and/or a light chain variable region at least about 80%, 85%, 90%, 95%, or 100% identical to the amino acid sequence of SEQ ID NO:8, SEQ ID NO:12, SEQ ID NO:16, or SEQ ID NO:31, The composition can also comprise sorbitol.

The invention further includes a pharmaceutical composition comprising a purified preparation of a monoclonal antibody and sodium citrate, wherein the pharmaceutical composition has a pH from about 6 to about 7 or has a pH of about 6. The purified preparation can comprise at least 3 isoforms of the antibody. The antibody can comprise a heavy chain variable region at least about 80%, 85%, 90%, 95%, or 100% identical to the amino acid sequence of SEQ ID NO:6, SEQ ID NO:10, SEQ ID NO:14, or SEQ ID NO:30 and/or a light chain variable region at least about 80%, 85%, 90%, 95%, or 100% identical to the amino acid sequence of SEQ ID NO:8, SEQ ID NO:12, SEQ ID NO:16, or SEQ ID NO:31. The composition can also comprise sorbitol.

In another aspect, the invention provides a stable pharmaceutical composition comprising a purified preparation of a human or humanized monoclonal antibody that binds specifically to a human antigen, histidine, sodium acetate, sodium phosphate, potassium phosphate, or sodium citrate, and a salt and/or a sugar, wherein the antibody has an N-glycan site in its heavy and/or light chain variable region. In another embodiment, the invention provides a stable pharmaceutical composition comprising a purified preparation of a human or humanized monoclonal antibody that binds specifically to a human antigen, a buffering agent, and a salt and/or a sugar, wherein the antibody comprises an N-glycan in its heavy and/or light chain variable region and wherein the pH of the composition is from about 5.5 to about 6.5. Optionally, the pH of the composition can be from about 5.7 to about 6.3 or can be about 6. Further, the invention encompasses a stable pharmaceutical composition comprising a purified preparation of a human or humanized monoclonal antibody that binds specifically to a human antigen, a buffering agent, for example histidine, sodium acetate, sodium phosphate, potassium phosphate, or sodium citrate, and a salt and/or a sugar, wherein the antibody is at least about 80%, 85%, 90%, 95%, 98%, or 100% identical to SEQ ID NO:6, SEQ ID NO:10, SEQ ID NO:14, and/or SEQ ID NO:30. The pH of the composition may be from about 5.5 to about 6.5. In a further aspect, the invention includes a stable pharmaceutical composition comprising a purified preparation of a human or humanized monoclonal antibody that binds specifically to a human antigen, a buffering agent, for example histidine, sodium acetate, sodium phosphate, potassium phosphate, or sodium citrate, and a salt and/or a sugar, wherein the antibody is at least about 80%, 85%, 90%, 95%, 98%, or 100% identical to SEQ ID NO:8, SEQ ID NO:12, SEQ ID NO:16, and/or SEQ ID NO:31. The pH of the composition may be from about 5.5 to about 6.5. Optionally, the pH of the composition can be from about 5.7 to about 6.3 or can be about 6. The composition can be liquid, and, if so, may not have been previously lyophilized. Alternatively, the composition can be lyophilized.

The invention also includes a method for stabilizing an antibody comprising the steps of: selecting a purified preparation of a monoclonal antibody having an N-glycan site in its heavy and/or light chain variable region and formulating the purified preparation in a solution comprising histidine, sodium acetate, sodium phosphate, potassium phosphate, or sodium citrate, and having a pH from about 5.5 to about 6.5. The solution can further comprise a sugar, such as sorbitol or sucrose, and/or a salt. The pH of the solution may be about 6.0. The antibody can comprise an amino acid sequence at least 80%, 85%, 90%, 95%, 98%, or 100% identical to SEQ ID NO:6, SEQ ID NO:10, SEQ ID NO:14, and/or SEQ ID NO:30. Alternatively or in addition, the antibody can comprise an amino acid sequence at least 80%, 85%, 90%, 95%, 98%, or 100% identical to SEQ ID NO:8, SEQ ID NO:12, SEQ ID NO:16, and/or SEQ ID NO:31.

Finally, the invention provides a method for stabilizing a purified preparation a human or humanized monoclonal antibody that binds to a human antigen, wherein the purified preparation comprises plural structural variants of the monoclonal antibody, comprising selecting a mixture of at least two, three, or four structural variants, wherein the structural variants are due to heterogeneous glycosylation of an N-glycan site, and formulating the mixture in a composition comprising a buffering agent, for example histidine, phosphate, citrate, or acetate, and a sugar and/or a salt at a pH from about 5 to about 6.5. The composition may further comprise sorbitol or sucrose.

BRIEF DESCRIPTION OF THE FIGURES

FIG. 5 shows the percent of low molecular weight and high molecular weight (LMW and HMW, respectively) species formed in purified isoform Peaks −2, −1, 0, +1, and +2 and FPB after 3 months of storage at 4° C.

as detected by SEC after 3 months of incubation at 37° C. at various pHs, as indicated. The samples were formulated as in FIG. 4.

Figure 7A:
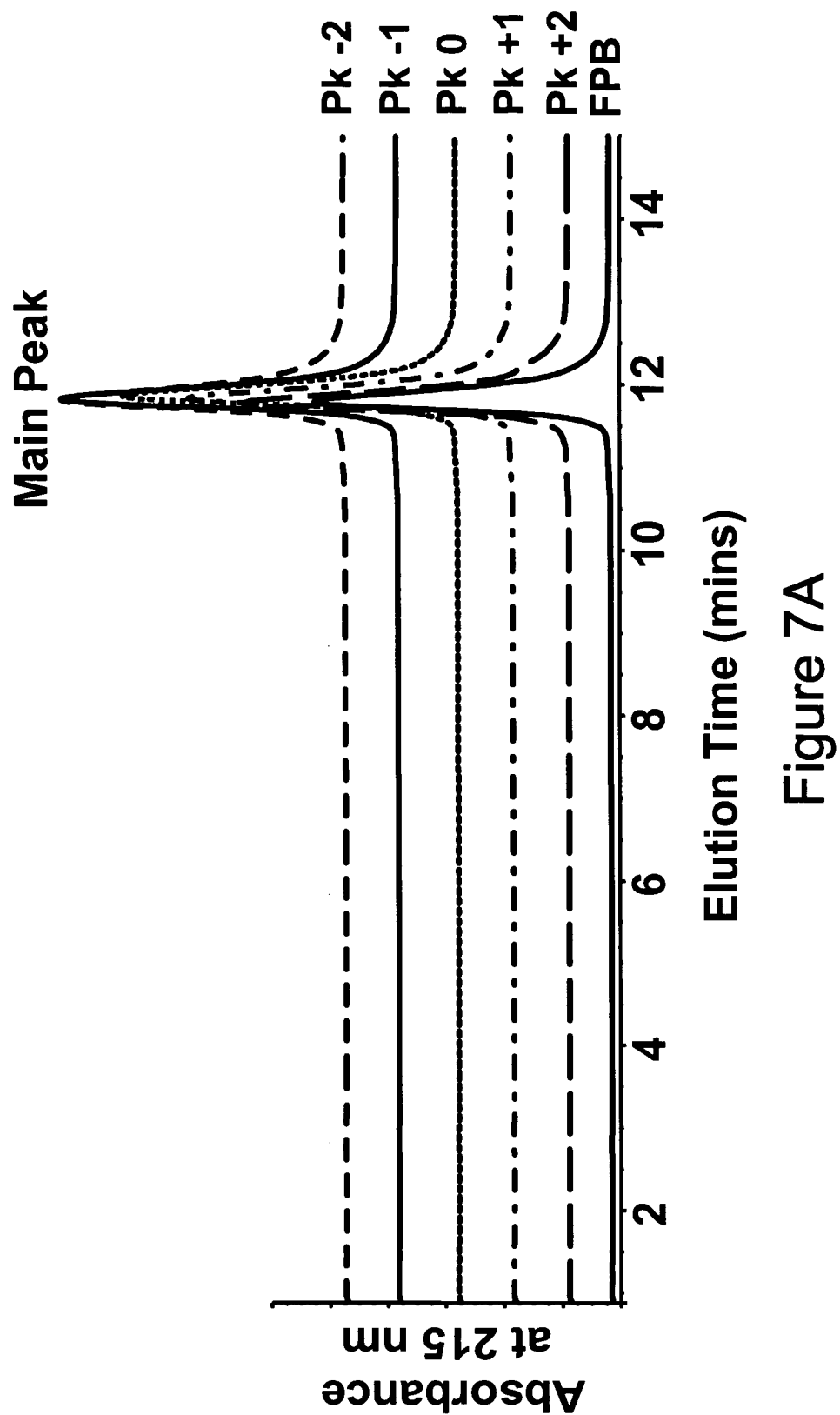
Figure 7B:
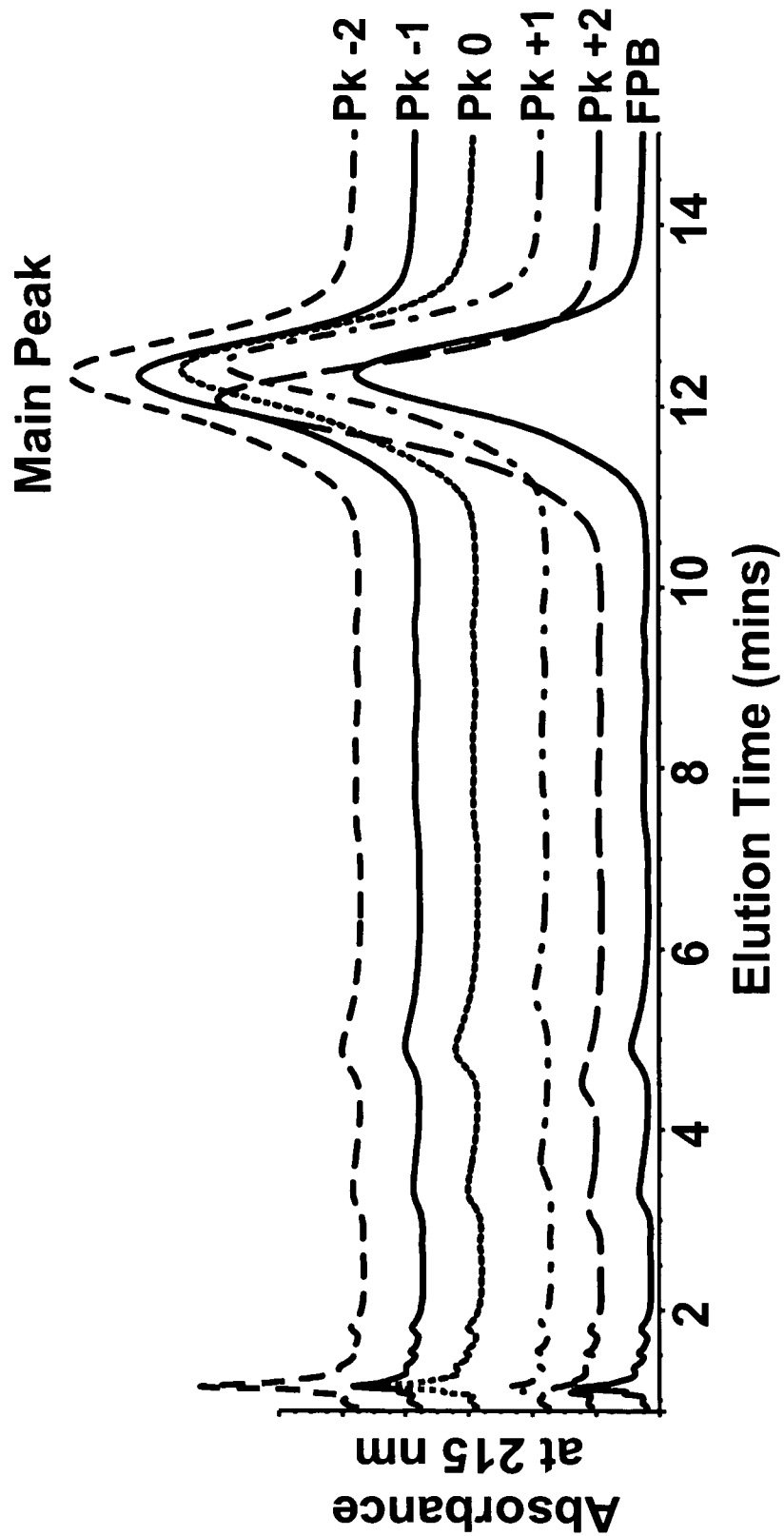

FIG. 7 shows overlaid $OD_{215}$ reversed phase chromatography (RPC) column profiles of material from purified isoform Peaks −2, −1, 0, +1, and +2 and FPB, as indicated in the figure, stored for three months at 4° C. (FIG. 7A) or at 37° C. (FIG. 7B) at pH 8 in a formulation containing 10 mM sodium phosphate and 5% sorbitol.

Figure 8A:
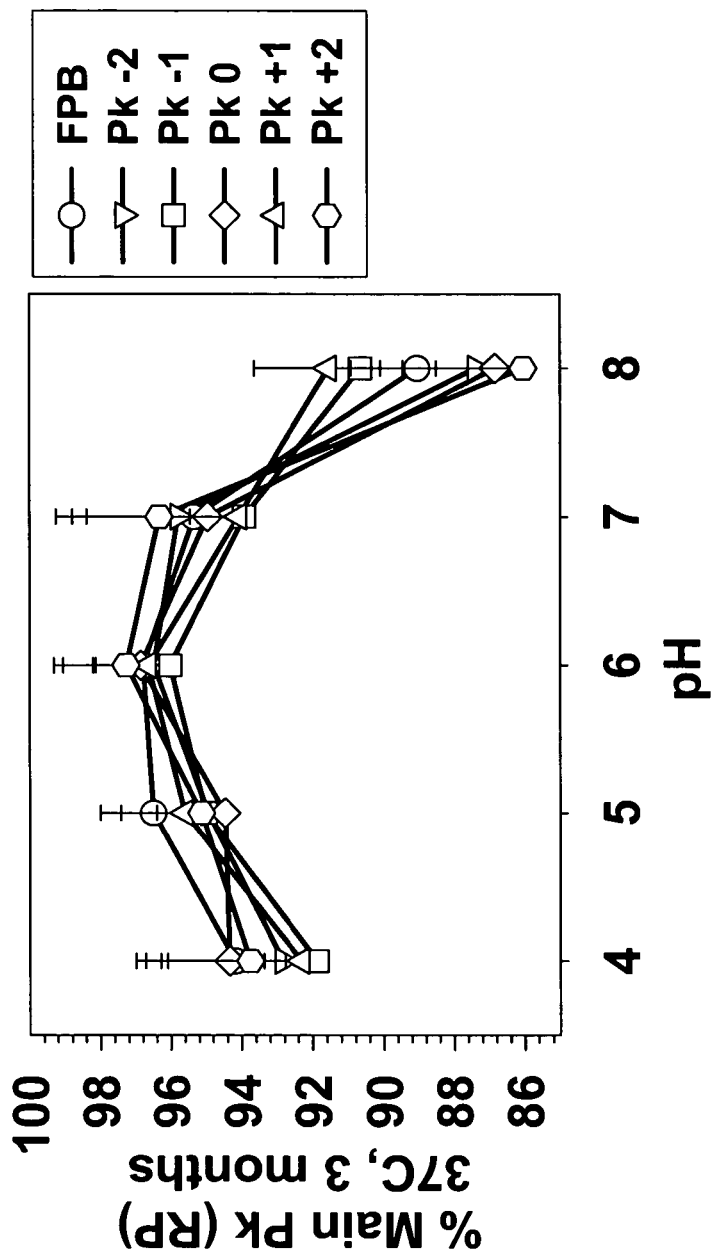
Figure 8B:
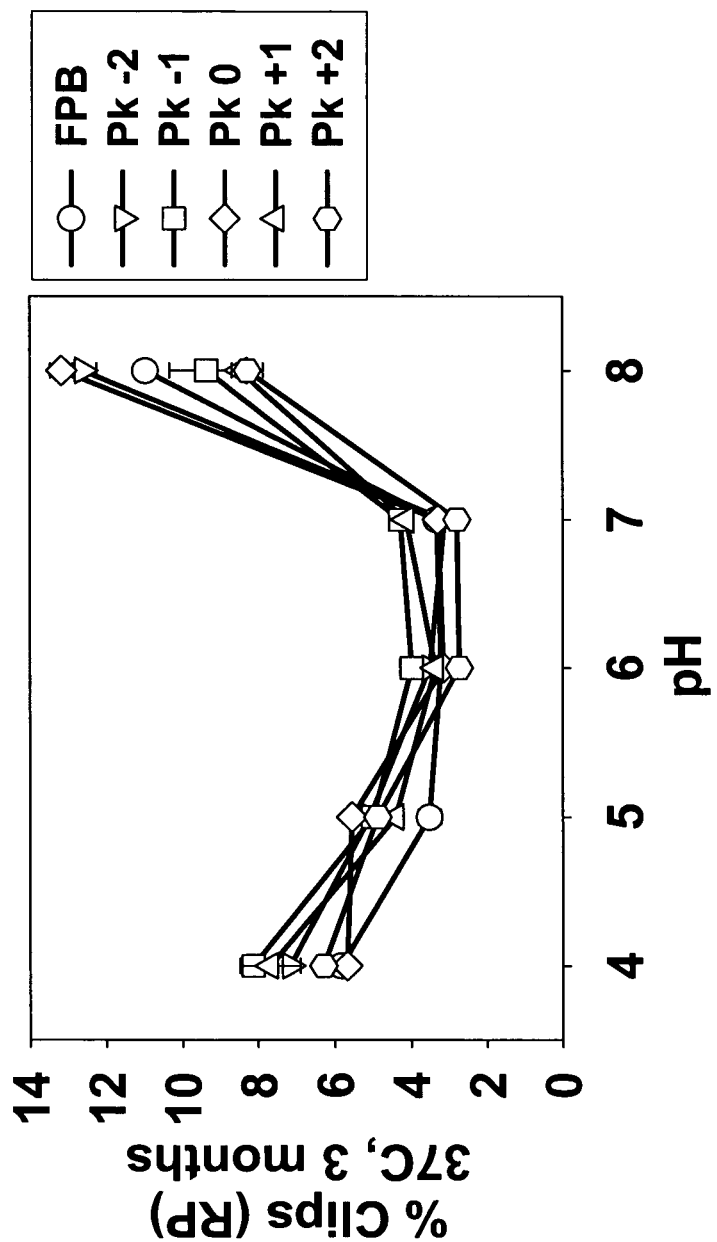

FIG. 8 shows the effects of pH on the percent of total antibody in the main peak (FIG. 8A) and in a hydrophilic clip species (FIG. 8B) in purified isoform Peaks −2, −1, 0, +1, and +2 and FPB, as indicated in the figure, after 3 months of incubation at 37° C. at various pHs, as indicated. Detection is by RPC. The samples were formulated as in FIG. 4.

Figure 9:
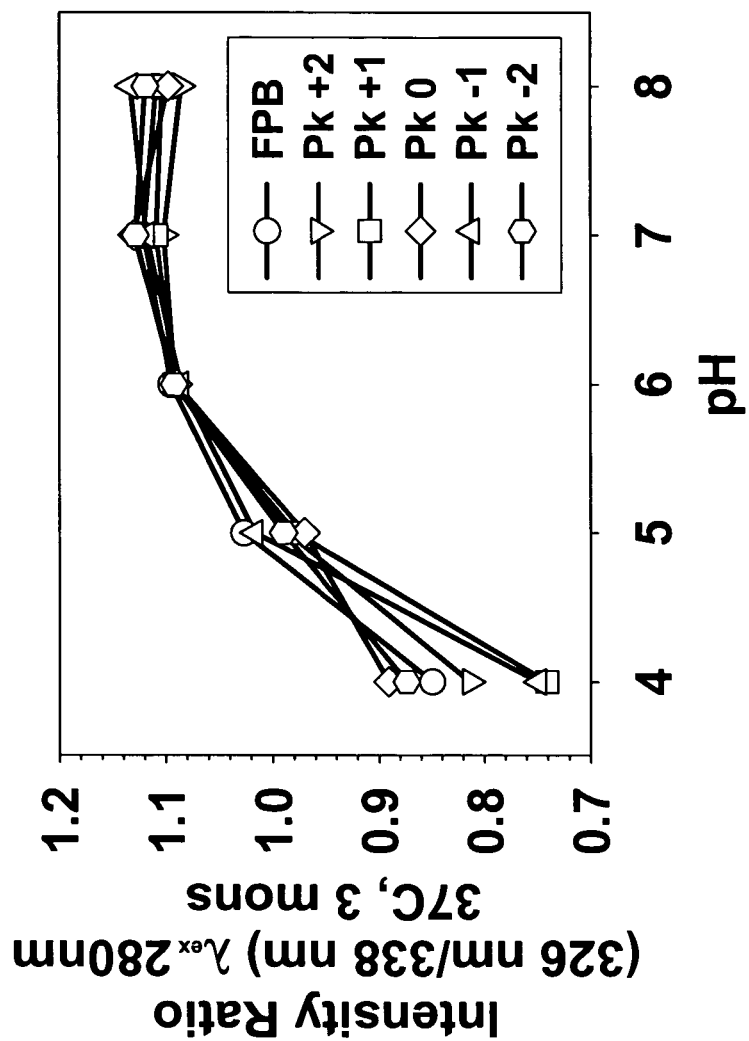

FIG. 9 shows the ratio of the intrinsic fluorescent intensity at emission wavelength 326 nm relative to that at 338 nm for formulations of peaks −2, −1, 0, +1, and +2 and FPB, as indicated in the figure, after 3 months of incubation at 37° C. at various pH's. The excitation wavelength is 280 nm. The samples were formulated as in FIG. 4.

FIG. 10 shows the amino acid sequence encoded by the human $V_H$ segment 5-51.

FIG. 11 shows the amino acid sequence encoded by the human $V_H$ segment 5-a.

FIG. 12 shows the amino acid sequence encoded by the human $V_K$ segment VKIII/A27.

Figure 13:
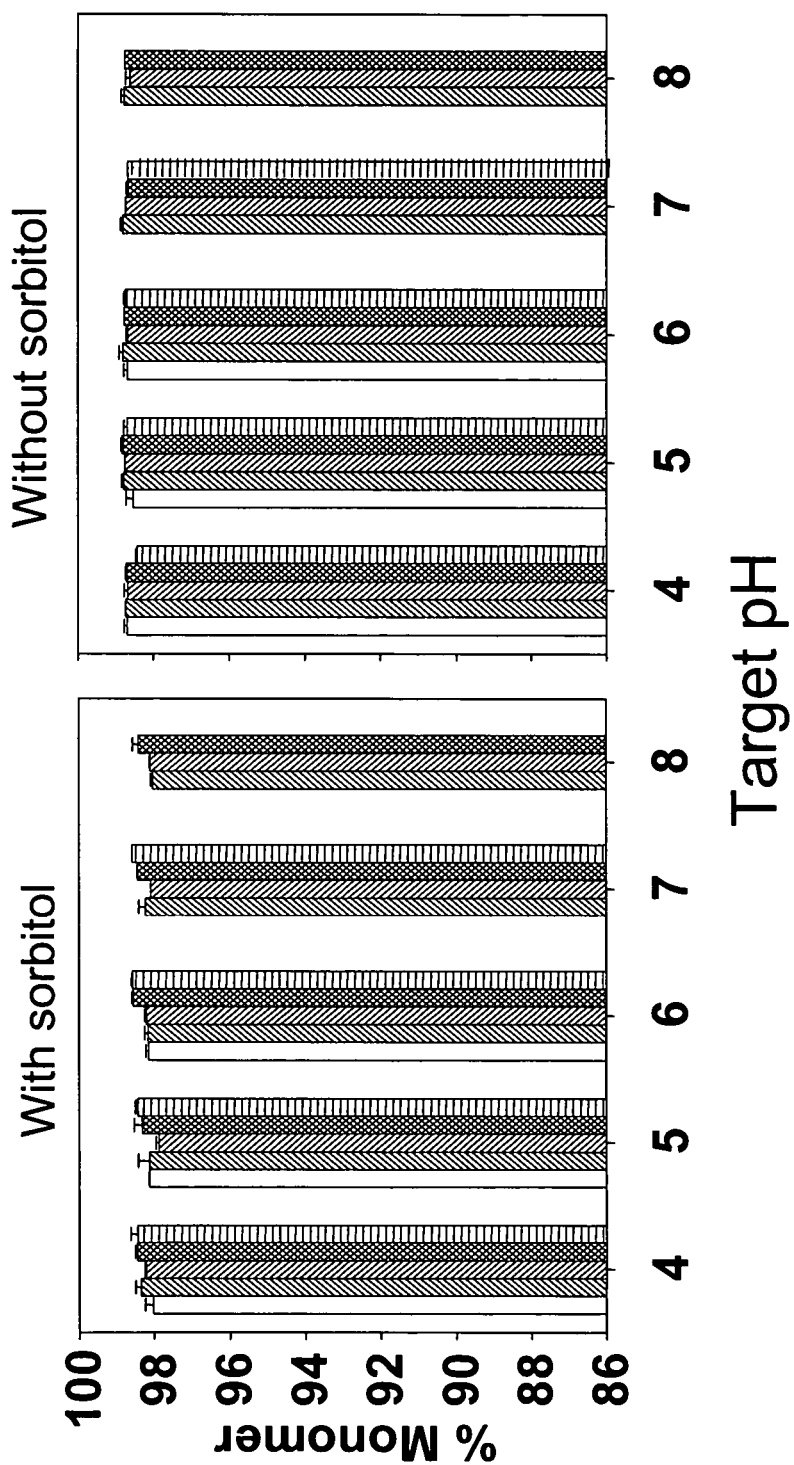

FIG. 13 shows the percent monomer as measured by SEC in samples in 10 mM sodium acetate ▭, histidine ▨, potassium phosphate ▨, sodium phosphate ▨, or sodium citrate ▭ with (left panel) or without (right panel) 5% sorbitol at the zero timepoint. All samples with a target pH of 4 are shown, although some are not at pH 4. See Example 3, Table 4. All other samples that are not within 0.4 pH units from the target pH are omitted.

Figure 14:
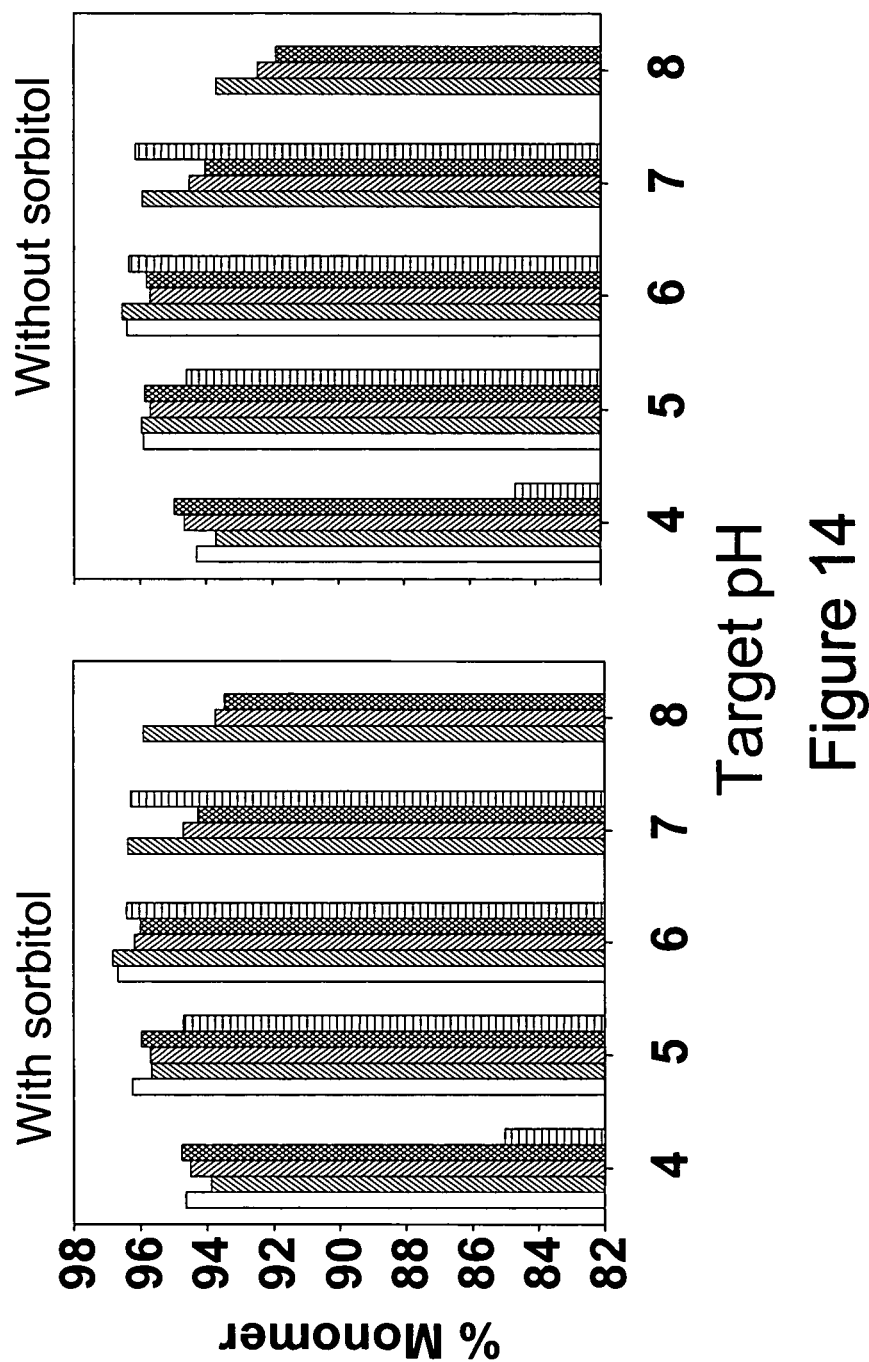

FIG. 14 shows the percent monomer as measured by SEC in samples incubated in 10 mM sodium acetate ▭, histidine ▨, potassium phosphate ▨, sodium phosphate ▨, or sodium citrate ▭ with (left panel) or without (right panel) 5% sorbitol after 12 weeks static at 37° C. Other than samples at target pH 4, all samples not within 0.4 pH units of the target pH are omitted.

Figure 15:
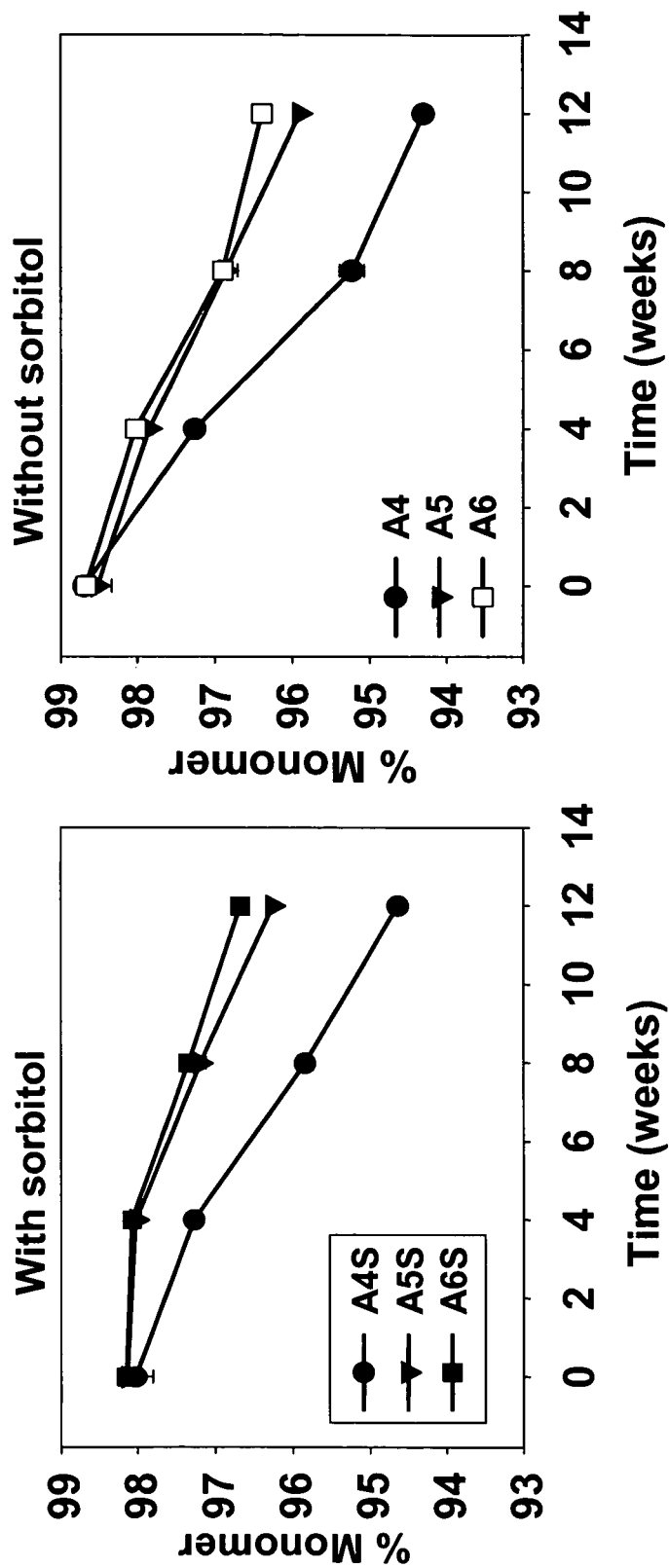

FIG. 15 shows the percent monomer as determined by SEC as a function of time at 37° C. in samples in 10 mM sodium acetate with (left panel) or without (right panel) 5% sorbitol. Sample designations in the figure are as in Table 4 (Example 3). Samples not within 0.4 pH units of the target pH are omitted.

Figure 16:
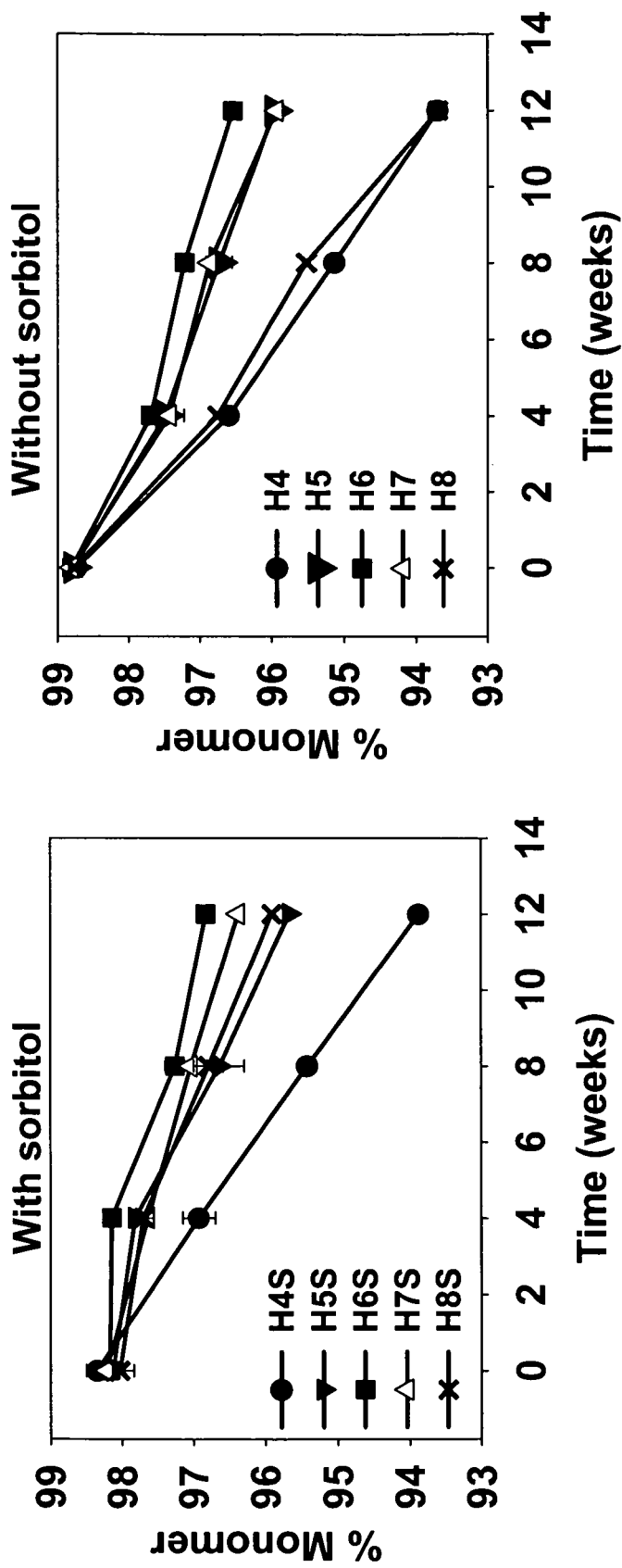

FIG. 16 shows the percent monomer as determined by SEC as a function of time at 37° C. in samples in 10 mM histidine with (left panel) or without (right panel) 5% sorbitol. Sample designations in the figure are as in Table 4 (Example 3).

Figure 17:
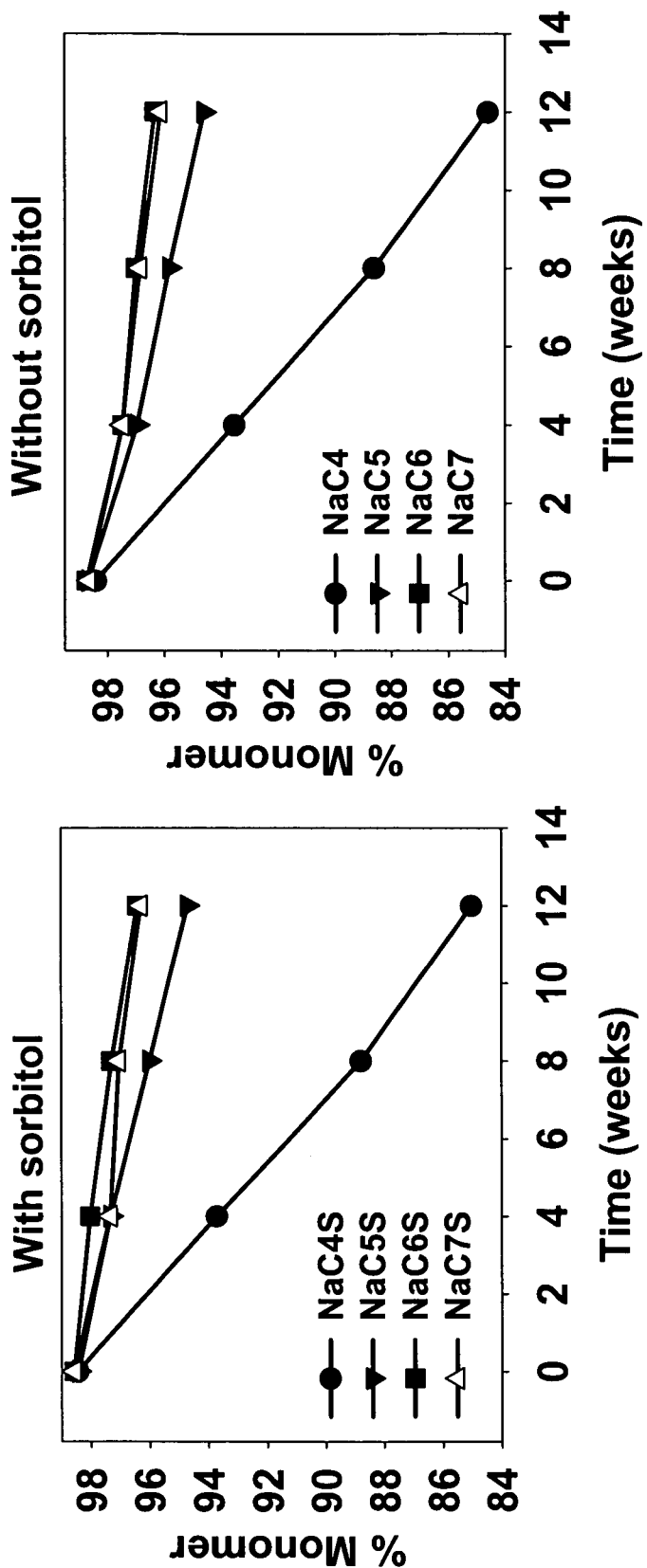

FIG. 17 shows the percent monomer as determined by SEC as a function of time at 37° C. in samples in 10 mM sodium citrate with (left panel) and without (right panel) 5% sorbitol. Sample designations in the figure are as in Table 4 (Example 3). Samples not within 0.4 pH units of the target pH are omitted.

Figure 18:
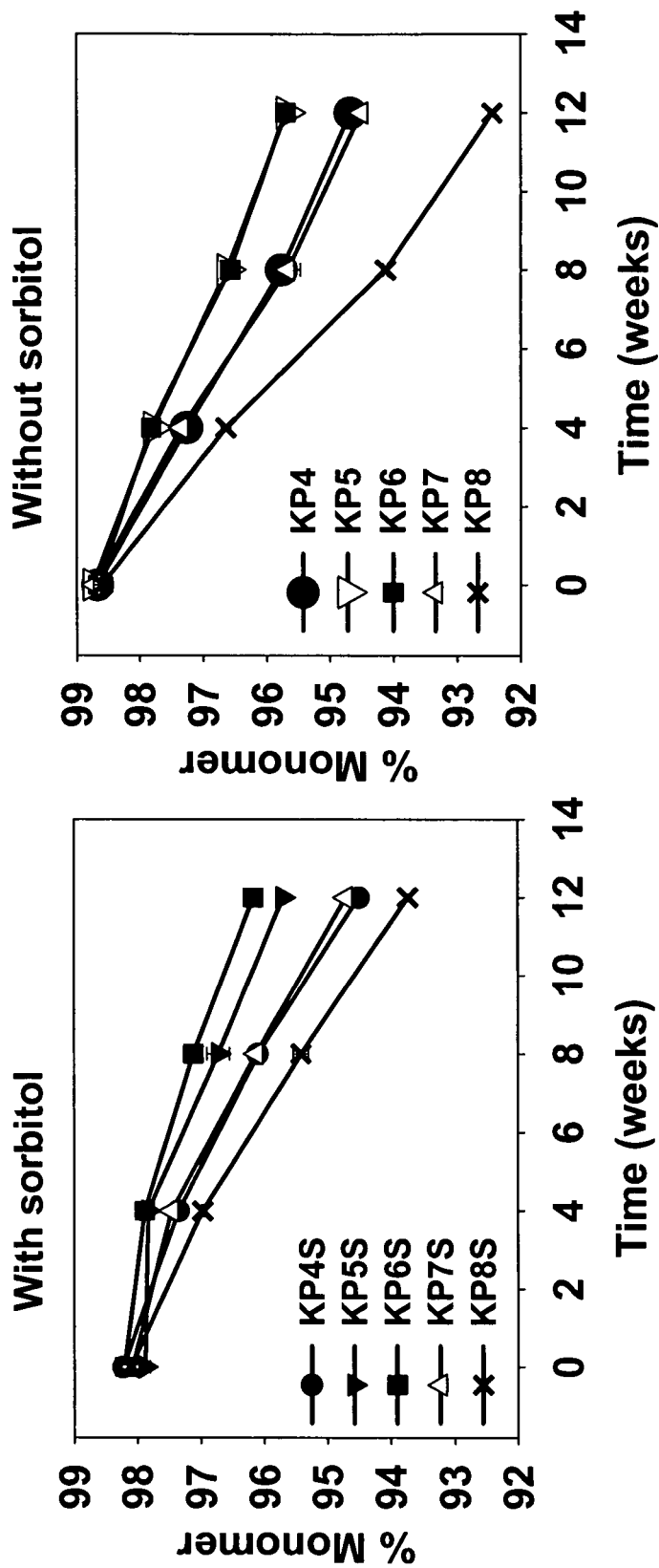

FIG. 18 shows the percent monomer as determined by SEC as a function of time at 37° C. in samples in 10 mM potassium phosphate with (left panel) and without (right panel) 5% sorbitol. Sample designations in the figure are as in Table 4 (Example 3).

Figure 19:
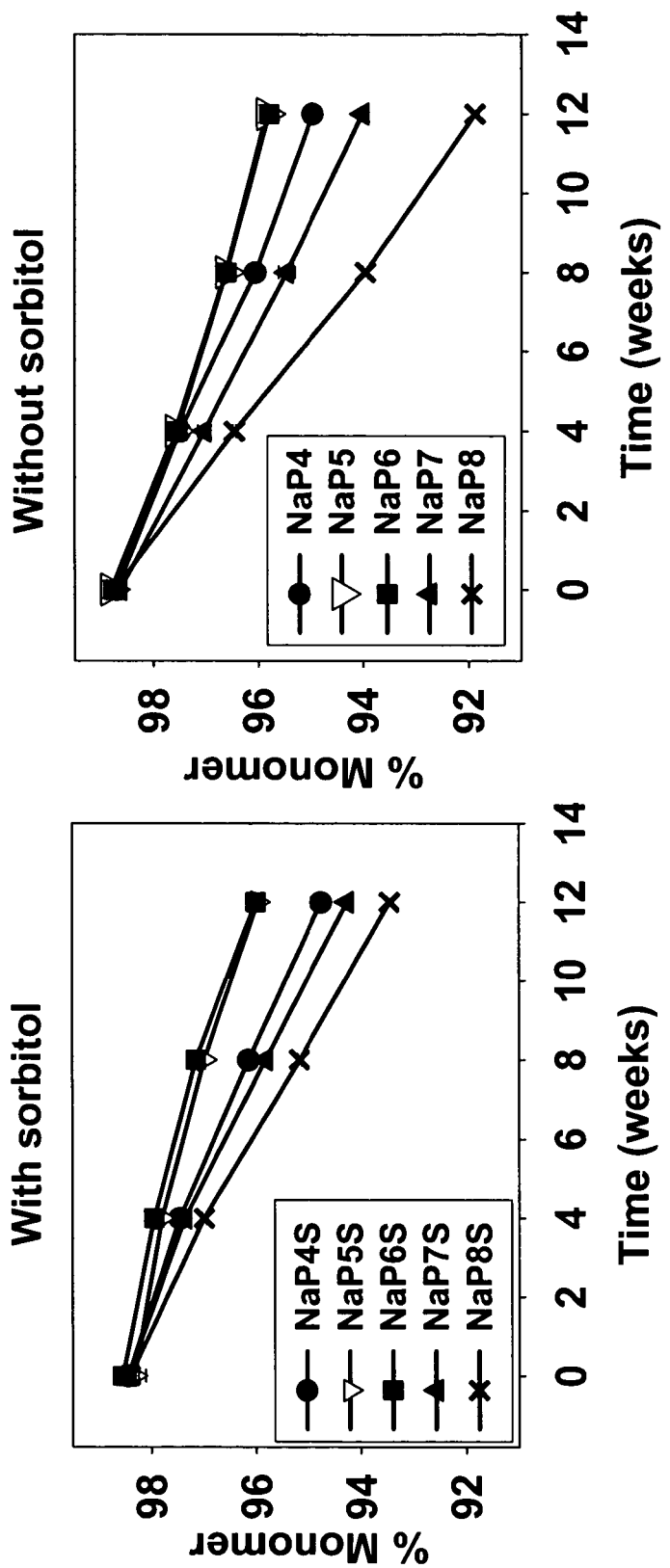

FIG. 19 shows the percent monomer as determined by SEC as a function of time at 37° C. in samples in 10 mM sodium phosphate with (left panel) and without (right panel) 5% sorbitol. Sample designations in the figure are as in Table 4 (Example 3).

Figure 20:
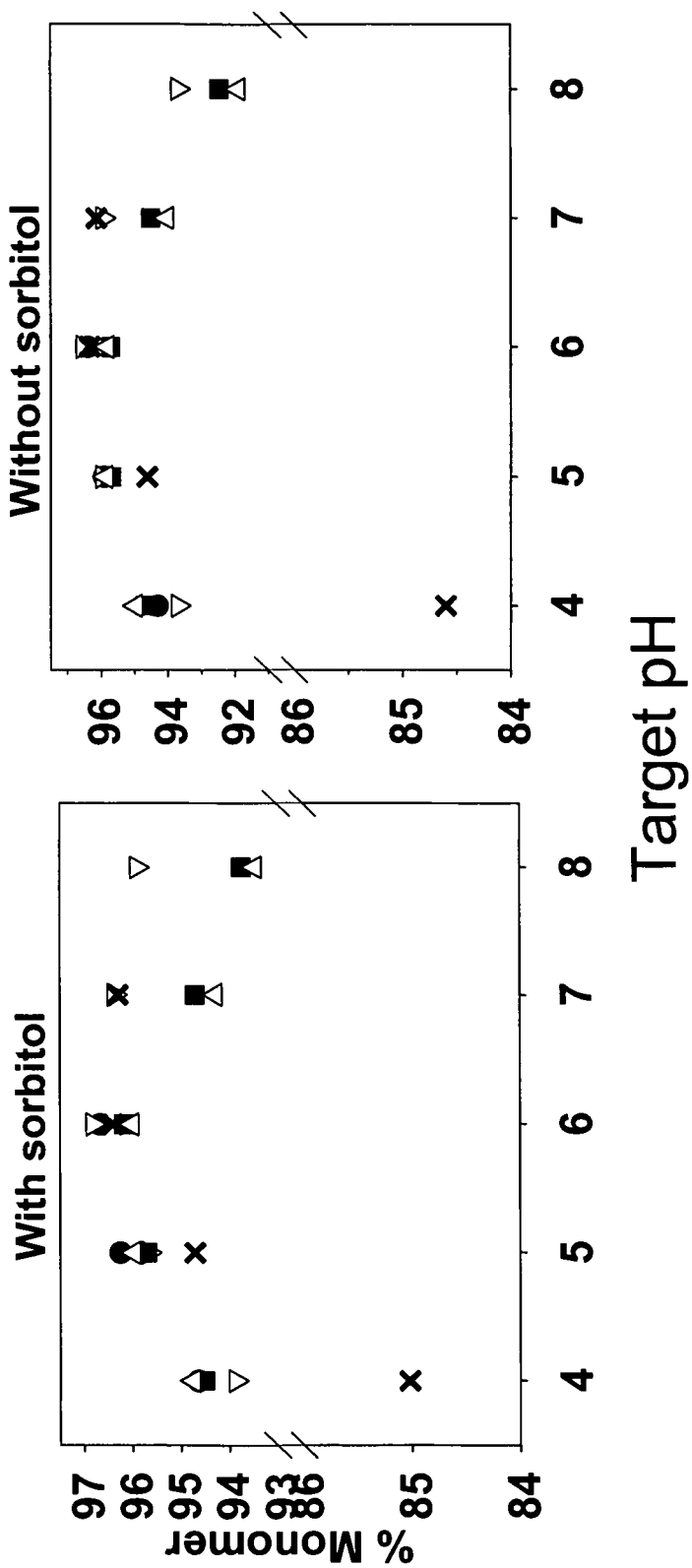

FIG. 20 shows the percent monomer as determined by SEC after 12 weeks of static incubation at 37° C. as a function of target pH. All samples at target pH 4 are shown, but all other samples that are more than 0.4 pH units from the target pH are omitted. Samples in the left panel contain 5% sorbitol, and samples in the right panel do not contain sorbitol. Different buffering agents, which are present at a concentration of 10 mM, are designated as follows: ●, sodium acetate; ∇, histidine; ■, potassium phosphate; ∆, sodium phosphate; and X, sodium citrate. The scale of the y axis is different in the left and right panels.

Figure 21:
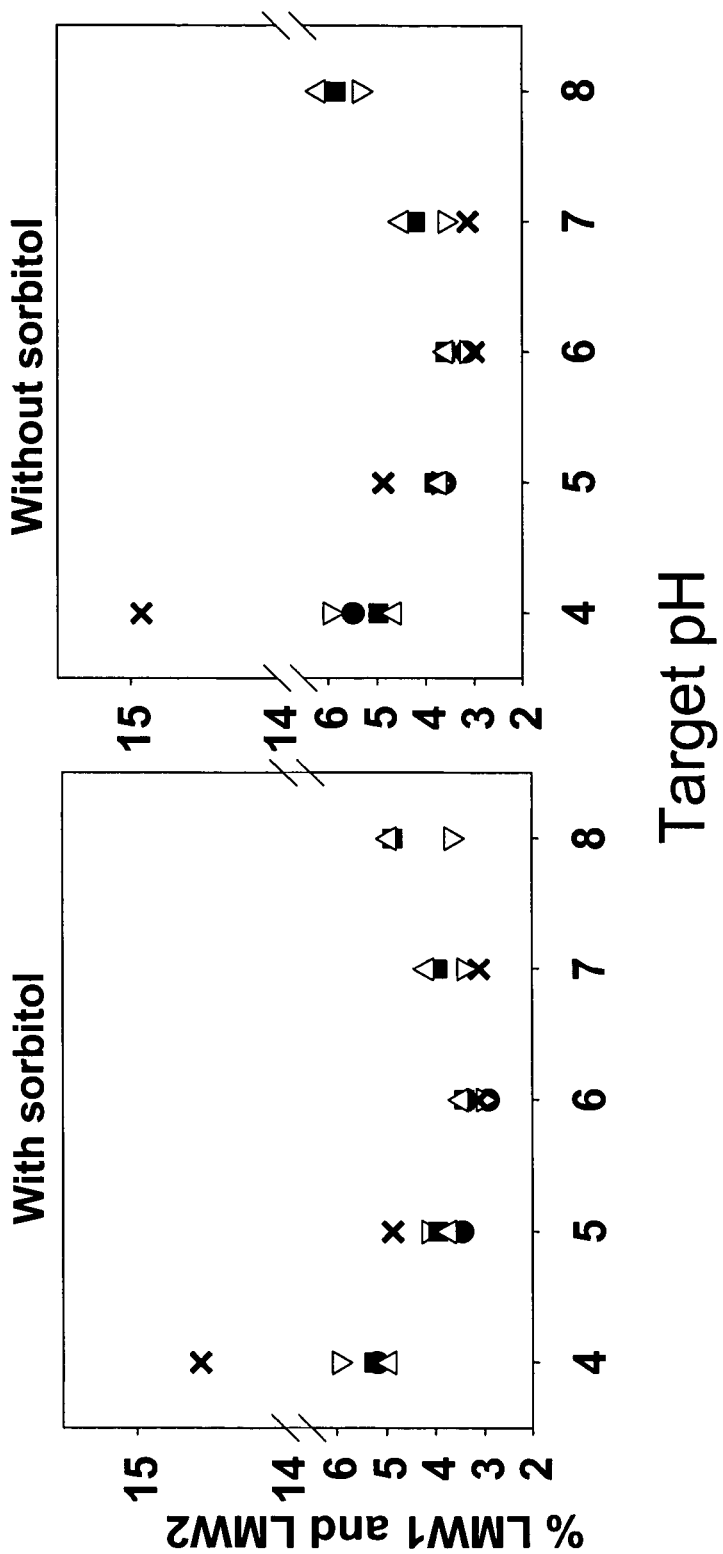

FIG. 21 shows the percent of low molecular weight species, LMW 1 and LMW 2, as determined by SEC after 12 weeks of static incubation at 37° C. as a function of target pH in samples with (left panel) and without (right panel) 5% sorbitol. Different buffering agents, which are present at a concentration of 10 mM, are designated as described in the description of FIG. 20. Samples, other than those of target pH 4, that are more than 0.4 pH units from the target pH are omitted.

Figure 22:
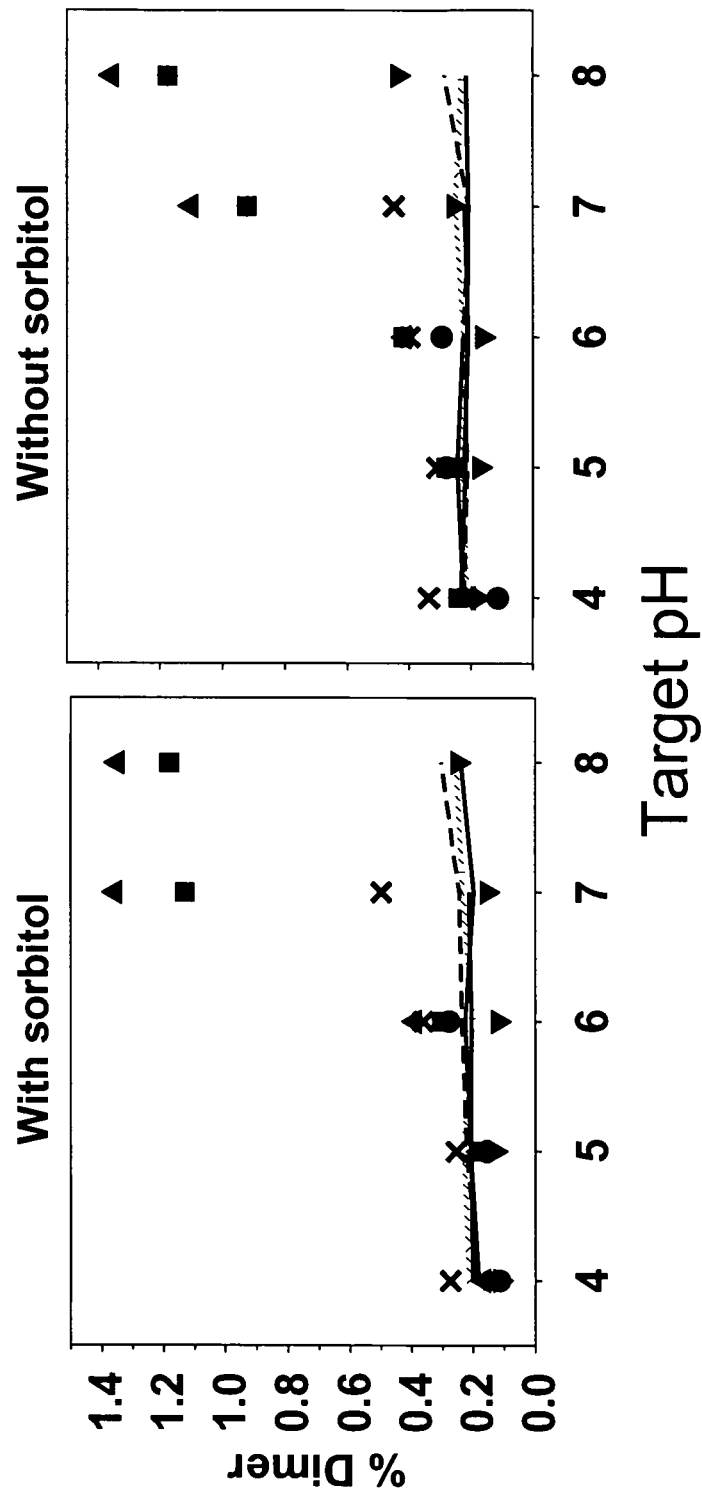

FIG. 22 shows the percent dimer as determined by SEC after 12 weeks of static incubation at 37° C. as a function of target pH in samples with (left panel) and without (right panel) 5% sorbitol. Different buffering agents, which are present at a concentration of 10 mM, are designated as follows: ●, sodium acetate; ∇, histidine; ■, potassium phosphate; ▲, sodium phosphate; and X, sodium citrate. Samples, other than those of target pH 4, that are more than 0.4 pH units from the target pH are omitted. The lines along the bottom of the figure represent the percent dimer at the zero timepoint for various samples, which were all very similar.

Figure 23:
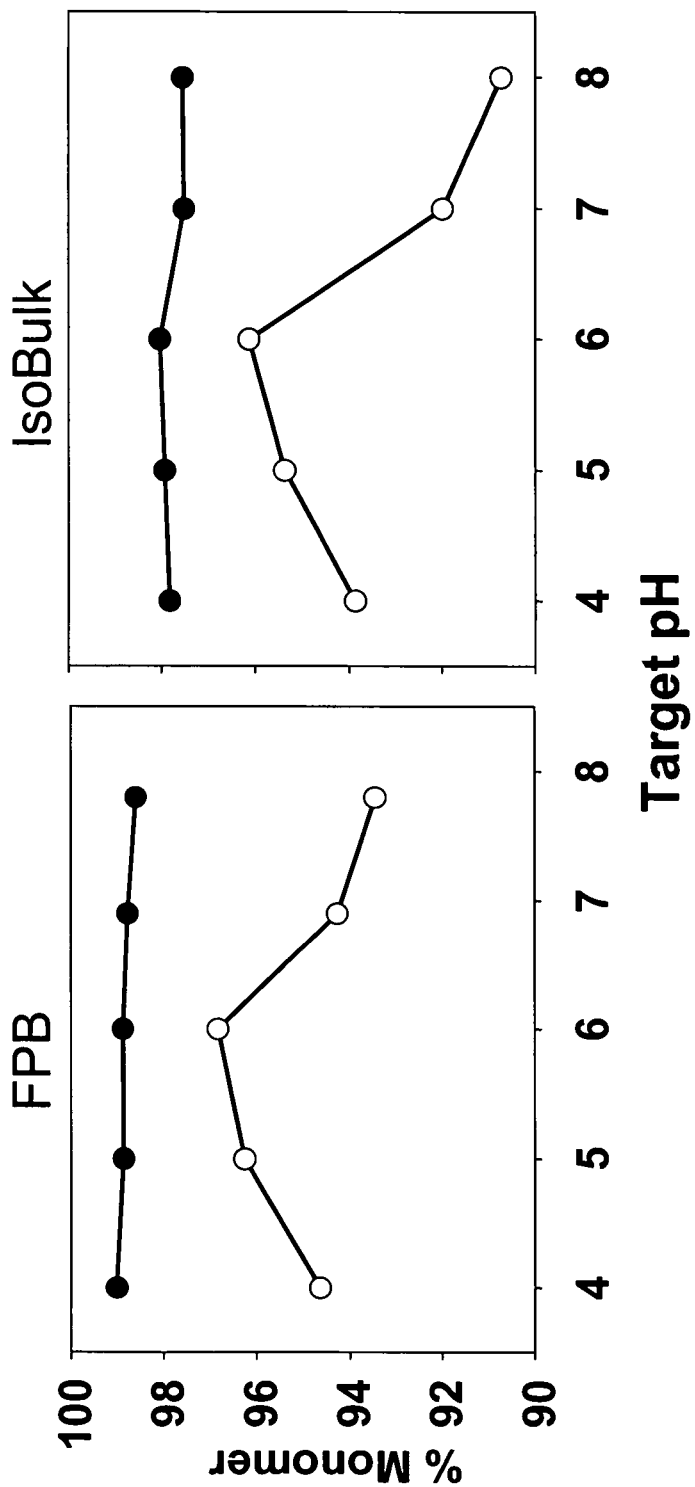

FIG. 23 shows the percent monomer as determined by SEC as a function of target pH for samples containing either FPB (left panel) or the IsoBulk mixture (right panel, described in detail in Example 4 and Table 5) after 12 weeks static incubation at either 4° C. (closed circles) or 37° C. (open circles). All samples contained sorbitol. Target pH was very close to actual pH. Samples at pHs 4 and 5 were formulated in 10 mM sodium acetate. Samples at pH 6 were formulated in 10 mM histidine. Samples at pHs 7 and 8 were formulated in 10 mM sodium phosphate.

Figure 24:
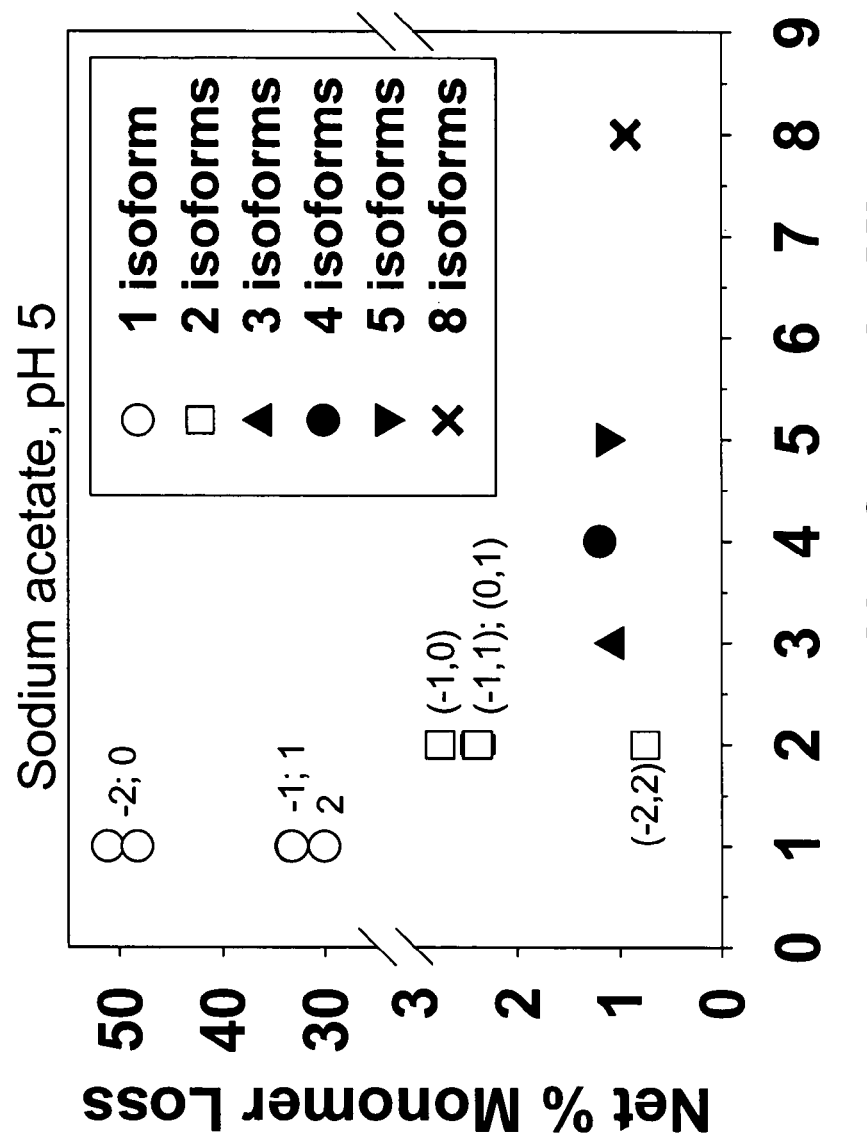

FIG. 24 shows the net loss in percent monomer as determined by SEC after eight weeks of static incubation at 37° C. for individual samples containing either a single purified isoform or mixtures of two, three, four, five, or eight different isoforms, as indicated. All samples are formulated in 5% sorbitol, 10 mM sodium acetate, pH 5. Data for single purified isoforms is from the experiments described in Example 2. Data for the isoform mixtures is derived from experiments described Examples 3 and 4. Numbers next to the data points for samples containing one or two isoforms indicate which isoforms are included in the sample. Samples containing three, four, and five isoforms are A5S (−1, −2, −3), A5S (1, 2, 3, 4), and A5S (IsoBulk), respectively. These are described in Example 4 and Table 5. The sample containing eight isoforms is FPB.

Figure 25:
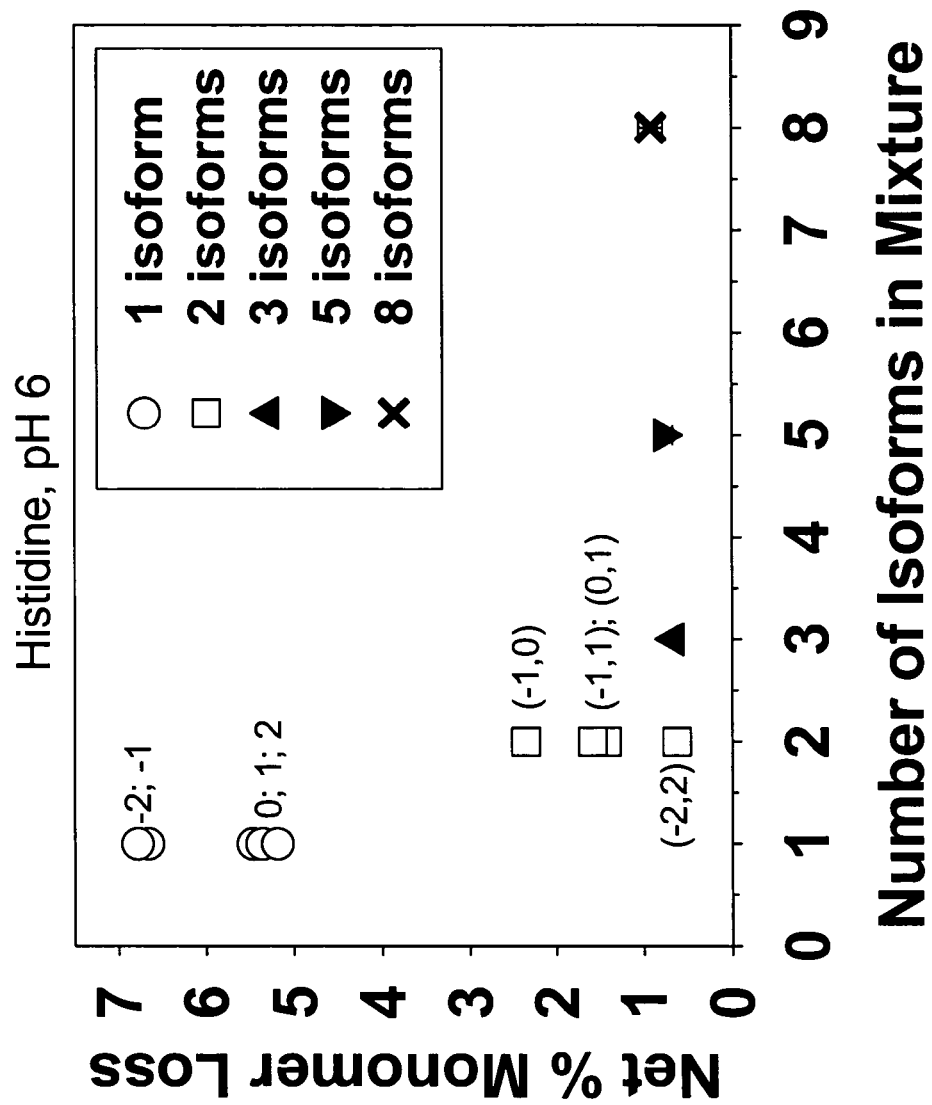

FIG. 25 shows the net loss in percent monomer as determined by SEC after eight weeks of static incubation at 37° C. for individual samples containing either a single purified isoform or mixtures of two, three, five, or eight different isoforms, as indicated. All samples are formulated in 5% sorbitol, 10 mM hisitidine, pH 6. Data for single purified isoforms is from the experiments described in Example 2. Data for the mixtures is derived from experiments described Examples 3 and 4. Numbers next to the data points for samples containing one or two isoforms indicate which isoforms are included in the sample. Samples containing three and five isoforms are H6S (−1, −2, −3) and H6S (IsoBulk), respectively. These are described in Example 4 and Table 5. The sample containing eight isoforms is FPB.

TABLE 1

BRIEF DESCRIPTION OF THE SEQUENCE LISTINGS

| Sequence Identification Number | Brief Description |
|---|---|
| SEQ ID NO: 1 | Nucleotide sequence encoding the heavy chain constant region of the 1118, 1118*, 1119, 1121, or 1121* antibody |
| SEQ ID NO: 2 | Amino acid sequence of the heavy chain constant region of the 1118, 1118*, 1119, 1121, or 1121* antibody |
| SEQ ID NO: 3 | Nucleotide sequence encoding the light chain constant region of the 1118, 1118*, 1119, 1121, or 1121* antibody |
| SEQ ID NO: 4 | Amino acid sequence of the light chain constant region of the 1118, 1118*, 1119, 1121, or 1121* antibody |
| SEQ ID NO: 5 | Nucleotide sequence encoding the heavy chain variable region of the 1119 antibody |
| SEQ ID NO: 6 | Amino acid sequence of the heavy chain variable region of the 1119 antibody |
| SEQ ID NO: 7 | Nucleotide sequence encoding the light chain variable region of the 1119 antibody |
| SEQ ID NO: 8 | Amino acid sequence of the light chain variable region of the 1119 antibody |
| SEQ ID NO: 9 | Nucleotide sequence encoding the heavy chain variable region of the 1118 antibody |
| SEQ ID NO: 10 | Amino acid sequence of the heavy chain variable region of the 1118 antibody |
| SEQ ID NO: 11 | Nucleotide sequence encoding the light chain variable region of the 1118 or 1118* antibody |
| SEQ ID NO: 12 | Amino acid sequence of the light chain variable region of the 1118 or 1118* antibody |
| SEQ ID NO: 13 | Nucleotide sequence encoding the heavy chain variable region of the 1121 or 1121* antibody |
| SEQ ID NO: 14 | Amino acid sequence of the heavy chain variable region of the 1121 or 1121* antibody |
| SEQ ID NO: 15 | Nucleotide sequence encoding the light chain variable region of the 1121 antibody |
| SEQ ID NO: 16 | Amino acid sequence of the light chain variable region of the 1121 antibody |
| SEQ ID NO: 17 | Amino acid sequence of the entire heavy chain of the 1119 antibody |
| SEQ ID NO: 18 | Amino acid sequence of the entire light chain of the 1119 antibody |
| SEQ ID NO: 19 | Amino acid sequence of the entire heavy chain of the 1118 antibody |
| SEQ ID NO: 20 | Amino acid sequence of the entire light chain of the 1118 or 1118* antibody |
| SEQ ID NO: 21 | Amino acid sequence of the entire heavy chain of the 1121 or 1121* antibody |
| SEQ ID NO: 22 | Amino acid sequence of the entire light chain of the 1121 antibody |
| SEQ ID NO: 23 | Nucleotide sequence of a PCR primer |
| SEQ ID NO: 24 | Nucleotide sequence of a PCR primer |
| SEQ ID NO: 25 | Nucleotide sequence of a PCR primer |
| SEQ ID NO: 26 | Nucleotide sequence of a PCR primer |
| SEQ ID NO: 27 | Nucleotide sequence of a PCR primer |
| SEQ ID NO: 28 | Nucleotide sequence of a PCR primer |
| SEQ ID NO: 29 | Nucleotide sequence of a PCR primer |
| SEQ ID NO: 30 | Amino acid sequence of the heavy chain variable region of 1118* antibody |
| SEQ ID NO: 31 | Amino acid sequence of the light chain variable region of 1121* antibody |
| SEQ ID NO: 32 | Amino acid sequence of the entire heavy chain of the 1118* antibody |
| SEQ ID NO: 33 | Amino acid sequence of the entire light chain of the 1121* antibody |
| SEQ ID NO: 34 | Amino acid sequence of the heavy chain CDR1 of the 1119, 1118, 1118*, 1121, or 1121* antibody |
| SEQ ID NO: 35 | Amino acid sequence of the heavy chain CDR2 of the 1119, 1118, 1118*, 1121, or 1121* antibody |
| SEQ ID NO: 36 | Amino acid sequence of the heavy chain CDR3 of the 1119 antibody |
| SEQ ID NO: 37 | Amino acid sequence of the heavy chain CDR3 of the 1118, 1118*, 1121, or 1121* antibody |
| SEQ ID NO: 38 | Amino acid sequence of the light chain CDR1 of the 1119 or 1121 antibody |

TABLE 1-continued

BRIEF DESCRIPTION OF THE SEQUENCE LISTINGS

| Sequence Identification Number | Brief Description |
| --- | --- |
| SEQ ID NO: 39 | Amino acid sequence of the light chain CDR1 of the 1118 or 1118* antibody |
| SEQ ID NO: 40 | Amino acid sequence of the light chain CDR1 of the 1121* antibody |
| SEQ ID NO: 41 | Amino acid sequence of the light chain CDR2 of the 1119, 1118, 1118*, or 1121 antibody |
| SEQ ID NO: 42 | Amino acid sequence of the light chain CDR2 of the 1121* antibody |
| SEQ ID NO: 43 | Amino acid sequence of the light chain CDR3 of the 1119, 1118, 1118*, or 1121 antibody |
| SEQ ID NO: 44 | Amino acid sequence of the light chain CDR3 of the 1121* antibody |
| SEQ ID NO: 45 | Nucleotide sequence encoding the heavy chain CDR3 of the 1119 antibody |
| SEQ ID NO: 46 | Nucleotide sequence encoding the heavy chain CDR3 of the 1118, 1118*, 1121, or 1121* antibody |
| SEQ ID NO: 47 | Nucleotide sequence encoding the light chain CDR3 of the 1118, 1118*, 1119, or 1121 antibody |
| SEQ ID NO: 48 | Amino acid sequence immediately preceding a heavy chain CDR1 |
| SEQ ID NO: 49 | Amino acid sequence that may immediately precede a heavy chain CDR2 |
| SEQ ID NO: 50 | Amino acid sequence that almost always follows a heavy chain CDR3 |
| SEQ ID NO: 51 | Amino acid sequence that usually follows a light chain CDR3 |
| SEQ ID NO: 52 | Amino acid sequence of a signal sequence |
| SEQ ID NO: 53 | Amino acid sequence of a signal sequence |
| SEQ ID NO: 54 | Amino acid sequence of a signal sequence |
| SEQ ID NO: 55 | Amino acid sequence of a signal sequence |
| SEQ ID NO: 56 | Nucleotide sequence of the heavy chain variable region of the 1118* antibody |
| SEQ ID NO: 57 | Nucleotide sequence of the light chain variable region of the 1121* antibody |
| SEQ ID NO: 58 | The amino acid sequence encoded by the human $V_H$ segment 5-51. |
| SEQ ID NO: 59 | The amino acid sequence encoded by the human $V_H$ segment 5-a. |
| SEQ ID NO: 60 | The amino acid sequence encoded by the human $V_\kappa$ segment VKIII/A27. |

DETAILED DESCRIPTION

An antibody can be formulated so as to stabilize its physical structure and biological activity. A particularly important aspect to stabilizing an antibody is to inhibit or prevent aggregation of the antibody since aggregated antibodies may be more immunogenic than monomers. See e.g., Hermeling et al. (2004), Pharm. Res. 21(6): 897-903. Immune responses to a therapeutic may produce unwanted side effects or decrease the effectiveness of the antibody. The instant invention provides compositions and methods for the formulation of antibodies, optionally compositions and methods for the formulation of purified preparations of monoclonal antibodies that are heterogeneous, for example, because of differences in glycosylation.

Important parameters for antibody stabilization include the purity and degree of heterogeneity of the antibody, the pH, and the buffering agent. Other attributes of a composition, such as salts, carbohydrates and/or sugars, amino acids, and/or many other ingredients, can also affect antibody stability. Concentration of the antibody may also affect stability. Different antibodies may be sensitive to some attributes of a composition and not to others. The invention is directed towards methods for stabilizing purified preparations monoclonal antibodies, stable compositions comprising these antibodies, and methods of using these compositions to treat certain diseases.

In some embodiments, the antibodies of the invention are "heterogeneous." A purified preparation of a monoclonal antibody is heterogeneous, as meant herein, if it comprises plural "structural variants," even though the antibody is a monoclonal antibody and substantially all of the molecules of the antibody in the purified preparation have identical amino acid sequences. Heterogeneity may arise, for example, from heterogeneous glycosylation, heterogeneity in disulfide bond formation, and/or heterogeneity in protein folding, among other possibilities. Not included among "structural variants," as meant herein, are variants with different amino acid sequences such as, for example, variants lacking C-terminal lysines or cyclized N-terminal glutamines. See e.g., Moorhouse et al. (1997), J. Pharmaceut. Biomed. Analysis 16: 593-603. For example, a heterogeneous monoclonal antibody may be an IgG antibody having an N-glycan site or O-glycan site other than the highly conserved N-glycan site in the $CH_2$ domain of the IgG heavy chain. This conserved N-glycan site is virtually unsialylated and is important for effector functions of an antibody. See e.g. Wright and Morrison (1997), TIBTECH 15: 26-32; Tao and Morrison (1989). J. Immunol. 143: 2595-2601; Sheeley et al. (1997), Analytical Biochem. 247: 102-10. Other N-glycan sites or O-glycan sites can occur anywhere in the antibody amino acid sequence, optionally in a heavy or light chain variable region or in the $C_L$, $CH_1$, $CH_2$, or $CH_3$ regions, and may be sialylated to varying degrees, thus generating different structural variants with different charges. Such differently charged variants are referred to herein as "isoforms." Alternatively, a heterogeneous antibody preparation may comprise structural variants that are differently folded, and the differently folded species may be separable by column chromatography. In some embodiments, such differently folded variants may have different disulfide bonding patterns and may be separable by column chromatography. A heterogeneous antibody preparation can exhibit different stability characteristics than a homogeneous preparation, and different homogeneous preparations comprising isolated structural variants may exhibit different stability characteristics from each other. Thus, compositions comprising just one structural variant or combinations of structural variants may be stable compositions suitable for marketing.

To determine whether observed heterogeneity of a purified antibody preparation is due to heterogeneous glycosylation among N-glycans, samples of a purified preparation of antibody can be analyzed by cation exchange chromatography, as described in Example 1, both with and without digestion with peptide: N-glycosidase F (PNGase F). Because PNGase F removes N-glycans from a protein, the N-glycanase-digested sample would be expected to exhibit little or no heterogeneity as compared to the undigested sample if the heterogeneity observed in the undigested sample were due to heterogeneous glycosylation. Digestion with PNGase can be carried out essentially as recommended by a manufacturer, for example New England Biolabs (Massachusett, USA). New England Biolabs supplies a 10×G7 reaction buffer and recommends incubating the reaction at 37° C. in 1× reaction buffer (50 mM sodium phosphate, pH 7.5) plus 1% NP-40. Other enzymes that specifically remove N-glycans, such as N-glycanase, could also be used with reaction conditions appropriate for those enzymes.

Primary sequence can be an important determinant of antibody structure. In some embodiments, the amino acid sequence of a heavy chain variable region of an antibody of the invention can be at least about 80%, optionally, at least about 85%, 87%, 90%, 92%, 95%, 98%, or 100% identical to SEQ ID NO:6, SEQ ID NO:10, SEQ ID NO:14, and/or SEQ ID NO:30. The amino acid sequence of a light chain variable region of an antibody of the invention can be at least 80%, optionally, at least 85%, 87%, 90%, 92%, 95%, 98%, or 100% identical to SEQ ID NO:8, SEQ ID NO:12, SEQ ID NO:16, and/or SEQ ID NO:31. The identity regions, as defined below, in any of these sequence comparisons can be at least about 40, 50, 60, 70, 80, 90, or 100 amino acids long. Further, an antibody of the invention may comprise a heavy chain CDR3 having an amino acid sequence comprising at least 7 of the amino acids of SEQ ID NO:36 in the same order and spacing as they occur in SEQ ID NO:36; or having an amino acid sequence comprising SEQ ID NO:37.

An "antibody," as meant herein, refers to a protein comprising one or more polypeptide chains that includes all or part of a heavy chain variable region and/or a light chain variable region of an antibody, wherein the antibody can bind to an antigen. Numerous naturally-occurring antibodies are described in, e.g. Kabat et al. (1991, Sequences of Proteins of Immunological Interest, Public Health Service N.I.H., Bethesda, Md.). An antibody may be able to modulate, i.e., agonize or antagonize, the biological activity of the antigen. "Antibodies" include naturally occurring antibodies, which are described below, including antibodies containing two complete heavy chains and two complete light chains, as well as antibody fragments such as F(ab), F(ab'), F(ab')$_2$, Fv, single chain Fv fragments, and antibodies comprising a single heavy or light chain variable regions without other domains found in naturally-occurring antibodies. Single-chain, chimeric, humanized, human, polyclonal, and monoclonal antibodies are antibodies as meant herein. In certain embodiments, antibodies are produced by recombinant DNA techniques. In additional embodiments, antibodies are produced by enzymatic or chemical cleavage of naturally occurring antibodies.

Antibodies may be of the IgG (including IgG$_1$, IgG$_2$, IgG$_3$, and IgG$_4$ subclasses), IgA (including IgA, and IgA$_2$ subclasses), IgM, IgD, or IgE isotypes and may comprise a kappa- or lambda-type light chain. An antibody may be a human or humanized antibody, a murine antibody, a rabbit antibody, a dromedary antibody, or any mammalian antibody.

The antibodies used in the compositions and methods of the invention are, in some embodiments, "monoclonal antibodies." As meant herein, a "monoclonal antibody" preparation contains, for the most part, antibodies having the same amino acid sequence. In some instances, sequence variation of a monoclonal antibody may occur due to post-translational events, including, for example, amino acid modification or cleavage. In contrast, polyclonal antibody preparations, which can, for example, be purified from blood samples from inoculated animals, comprise antibodies with many different amino acid sequences. Monoclonal antibodies can be made by any appropriate means. For example, monoclonal antibodies can be isolated from hybridoma cell lines that produce an antibody with a single amino acid sequence. Such hybridoma lines can be isolated by the method of Kohler and Milstein (1975, Nature 256: 495) and cultured either in vivo or in vitro. Alternatively, monoclonal antibodies can be produced as follows. Nucleic acids encoding an antibody can be introduced into a host cell line that does not normally produce an antibody, for example, a bacterial, yeast, insect, or mammalian cell line. If the cell line is a mammalian cell line, it can, for example, be a Chinese hamster ovary (CHO) cell line or a VERO, BHK, HeLa, CV1 (including Cos), MDCK, 293, 3T3, myeloma (e.g., NSO, NS1), PC12, or W138 cell line. The cell line containing the antibody-encoding nucleic acids can be cultured, and the antibody can be harvested from the culture medium or the cells.

A "purified preparation of a monoclonal antibody" refers to a preparation in which at least about 80%, optionally at least about 85%, 90%, 92%, 95%, 97%, 98%, or 99%, of the detectable protein in the preparation is in the monomer (as defined below) peak as assessed by size exclusion chromatography (SEC). The method of SEC is explained in Example 2 and FIG. 3. The monomer peak detected in Example 2 contains a tetrameric antibody comprising two complete heavy chains and two complete light chains. However, monomer peaks containing other kinds of antibodies (as defined above) is contemplated in defining what a purified preparation of a monoclonal antibody is.

An "scFv" is a single chain antibody comprising a heavy chain variable region (V$_H$) and a light chain variable region (V$_L$) and not comprising a constant region of an antibody. In some embodiments scFv's can also comprise a linker of variable length between the heavy and light chain variable regions. Although an scFv can be fused to other amino acid sequences, the portion of a protein referred to as an scFv preferably does not comprise any substantial amount of amino acid sequence other than a V$_H$ region, a V$_L$ region, and, optionally, a linker joining these sequences.

An "Fc region" of an antibody is a heavy chain fragment comprising a C$_H$2 and a C$_H$3 domain and a hinge region (or a portion thereof) or a variant of such a fragment, and not comprising a C$_H$1 domain or a V$_H$ domain. See e.g. Kuby, Immunology, Second Edition, p. 110-11, W.H. Freeman and Co., New York (1994). An Fc fragment can be of the IgA, IgD, IgE, IgG, or IgA isotype, including IgG$_1$, IgG$_2$, IgG$_3$, IgG$_4$ or other subclasses.

An "scFv-Fc" is an antibody containing an scFv fused to an Fc region.

In general, naturally-occurring antibodies from most mammals comprise two heavy chains and two light chains. A heavy chain comprises three or four constant domains, the $CH_1$, $CH_2$, and $CH_3$ domains, and, in IgE and IgM antibodies, also the $CH_4$ domain. A heavy chain comprises one variable domain, the $V_H$ domain. A light chain comprises one constant domain, the $C_L$ domain, and one variable domain, the $V_L$ region. Light chain variable regions can belong to either the lambda family or kappa family, which are two groups of light chains that are related in sequence. A heavy or light chain variable domain comprises three complementarity determining regions (CDRs, also known as hypervariable regions, designated CDR1, CDR2, and CDR3 by Kabat et al., 1991, Sequences of Proteins of Immunological Interest, Public Health Service N.I.H., Bethesda, Md.; see also Chothia and Lesk, 1987, J. Mol. Biol. 196: 901-17; Chothia et al., 1989, Nature 342: 877-83) embedded within a framework region (designated framework regions 1-4, FR1, FR2, FR3, and FR4, by Kabat et al., supra; see also Chothia and Lesk, supra). The CDRs and the framework segments are interspersed as follows, starting at the amino terminus of the variable region: FR1-CDR1-FR2-CDR2-FR3-CDR3-FR4. The antibodies of the invention may be human or humanized antibodies having human framework regions.

Antibody variable regions can generally be identified as such by their primary amino acid sequence. The primary sequences of the framework regions of antibody variable regions have a handful of residues that are universally conserved across phyla. In addition, many residues are highly conserved across phyla and/or within species and/or phyla, and many positions within antibodies are usually occupied by one of a known group of amino acids. See Kabat et al., supra. Alternatively, or in addition, a sequence can be recognized as an antibody by its predicted tertiary structure. The tertiary structure of the variable regions, which comprises 9 β strands forming a structure known as a Greek key β barrel, is extremely well conserved, and the positions of the CDRs within this structure are also highly conserved. See e.g., Bork et al., 1994, J. Mol. Biol. 242: 309-20; Hunkapiller and Hood, 1989, Adv. Immunol. 44: 1-63; Williams and Barclay, 1988, Ann. Rev. Immunol. 6: 381-405; Chothia and Lesk, supra; Kabat et al., supra.

The genomic sequences encoding heavy chain variable regions have been mapped and sequenced. See e.g., Cook and Tomlinson (1995), Immunol. Today 16(5): 237-42. In nature, a heavy chain variable region is encoded by DNA comprising three disparate germline DNA segments, the $V_H$, D, and $J_H$ segments, which are brought together by DNA rearrangement events in antibody-producing cells. Most of the length of a naturally occurring heavy chain variable region is encoded by the $V_H$ segment, which encodes approximately 94 of a total of about 108 amino acids of a human heavy chain variable region. Thus, a group of germline $V_H$ segments can be determined, one of which partially encodes a particular heavy chain variable region in question, based on sequence similarity to known $V_H$ segments. In some cases, sequence similarity can point to a single germline $V_H$ segment as encoding an antibody in question. There are approximately fifty-one functional human germline $V_H$ segments, which are classified into seven families by sequence similarity. In some embodiments, the antibodies of the invention are at least about 80%, optionally at least about 85%, 90%, 95% or 98% identical to the amino acid sequence encoded by a human germline $V_H$ segment of family 5, optionally $V_H$ segment 5-51 or 5-a. See e.g., Cook and Tomlinson (1995), Immunol. Today 16(5): 237-42. Alternatively, the antibodies of the invention may be at least about 80%, optionally at least about 85%, 90%, 95%, or 98% identical to the amino acid sequence encoded by a human germline $V_H$ segment of family 1, 2, 3, 4, 6, or 7.

Similarly, naturally-occurring DNA encoding a human light chain variable region normally results from DNA rearrangement events in antibody producing cells that bring together a germline $V_L$ segment and a $J_L$ segment. Human $V_L$ and $J_L$ segments are found at two genetic loci, one on chromosome 2 and another on chromosome 22, which contain sequences that encode kappa chains and lambda chains, respectively. There are approximately 31 functional human $V_\lambda$ gene seqments (which are $V_L$ segments that encode lambda-type light chains), which fall into ten families (VL1 to VL10) on the basis of sequence similarity. Williams et al. (1996), J. Mol. Biol. 264: 220-32. There are about 40 functional germline $V_\kappa$ segments (which are $V_L$ segments that encode kappa-type light chains), which fall into seven families, VKI to VKVII. The antibodies of the invention may comprise a kappa or a lambda light chain, optionally one comprising a light chain variable region at least about 80%, optionally at least about 85%, 90%, 95%, or 98% identical to the amino acid sequence encoded by a germline $V_\kappa$ segment in the VKIII family, such as, for example, VKIII/A27. Alternatively, the light chain variable region may be at least about 80%, 90%, 95%, or 98% identical to the amino acid sequence encoded by a $V_\kappa$ segment in the VKI, VKII, VKIV, VKV, VKVI, or VKVII families.

As meant herein, a "monomer," when it refers to an antibody, is one complete antibody, which may comprise more that one polypeptide chain. For example, a monomer of many naturally-occurring antibodies consists of two heavy and two light chains, i.e. four polypeptide chains in all. Further, a monomer of some single chain antibodies (an scFv comprising one heavy chain variable region and one light chain variable region) is a single polypeptide chain. However, scFvs may spontaneously dimerize because of the length of the linker between the heavy and light chain variable regions. In such cases a monomer can be a dimeric scFv (or diabody). Similarly, a monomer of a naturally-occurring dromedary antibody, which comprises two heavy chains and no light chains (Muldernans et al., 2001, J. Biotechnol. 74:277-302; Desmyter et al., 2001, J. Biol. Chem. 276:26285-90) or an scFv-Fc is a dimer. In short, a monomer is one complete antibody, complete with all molecules that are part of the antibody.

"Human" antibodies are antibodies that are encoded by sequences that are ultimately derived from a human source. For example, an antibody isolated from human blood is a human antibody. An antibody from a hybridoma cell line that is a fusion of a human antibody-producing cell with an immortalized cell is a human antibody. Further, antibodies isolated from phage libraries of human DNA encoding antibody variable regions are human antibodies. Human antibodies also include antibodies with human sequences produced by transgenic animals in which human antibody-encoding sequences have replaced at least some of the antibody-encoding sequences in the transgenic animal, such as those described in, e.g., U.S. Pat. Nos. 5,625,126 and 6,075,181. Further, a human antibody may be produced by host cells into which nucleic acids of human origin encoding the antibody have been introduced. A "human" antigen is a molecule present in a human, such as, for example, a protein expressed in a human or a sugar or carbohydrate found in humans, among other possibilities.

"Humanized antibodies" are antibodies in which the framework regions of the variable region(s) of an antibody are of human origin, and the CDRs originate elsewhere. Humanized antibodies are described in, e.g., U.S. Pat. No. 5,693,761.

Antibodies may have N- or O-linked glycans attached to them. O-linked glycans are added to some but not all serine or threonine residues. There is no consensus sequence for predicting which serines or threonines will be glycosylated, although some predictive factors are known. See Essentials of Glycobiology, Varki et al., eds., Chapter 8, Cold Spring Harbor Laboratory Press, New York (1999). N-linked glycans are added to asparagine residues that occur in the sequence context Asn-Xxx-Ser/Thr, where Xxx is any amino acid except proline. Such a sequence is referred to herein as an N-glycan site or an N-glycosylation site. Essentials of Glycobiology, Varki et al., eds., Chapter 7, Cold Spring Harbor Laboratory Press, New York (1999). A proline following the Asn-Xxx-Ser/Thr sequence substantially decreases the frequency with which the asparagine is glycosylated. Gavel and von Heijne (1990), Protein Eng. 3(5): 433-42.

Figures 1A, 1B, 1C, 1D:
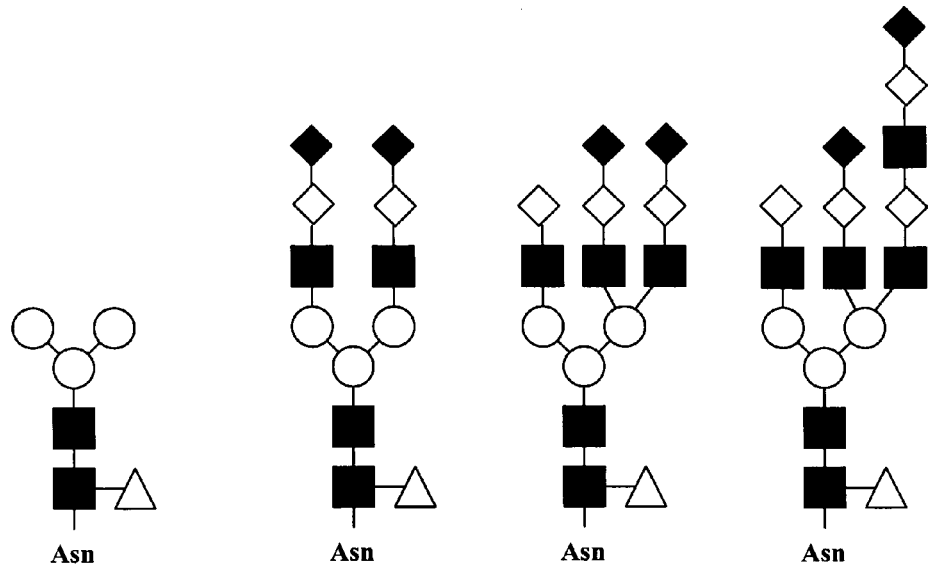
FIGS. 1A to 1G are diagrams depicting the structures of an N-glycan core structure (1A), a disialylated biantennary N-glycan with no branches comprising more than one N-acetylglucoseamine plus galactose (LacNAc) unit (1B), a disialylated triantennary N-glycan (1C), a disialylated triantennary N-glycan with one branch comprising two LacNAc units (1D), a tetrasialylated tetraantennary N-glycan (1E), a trisialylated tetraantennary N-glycan with one branch comprising two LacNAc units (1F), and a trisialylated tetraantennary N-glycan with two branches comprising two LacNAc units (1G). The symbols represent the following sugar residues: filled square, N-acetylglucosamine (GlcNAc); open circle, mannose (Man); open diamond, galactose (Gal); filled diamond, sialic acid (Sia); and open triangle, fucose (Fuc).
Figures 1E, 1F, 1G:
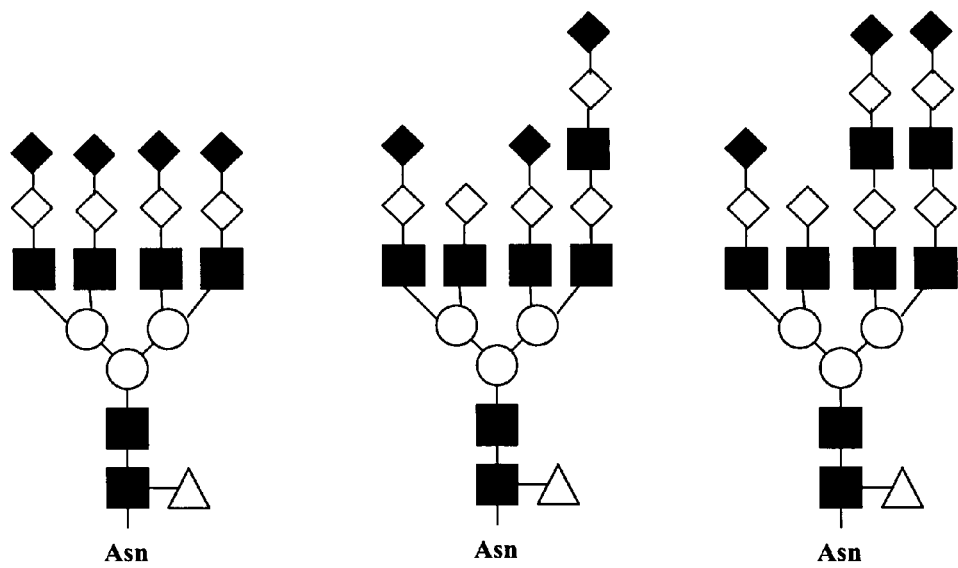

N-glycans can have a complex and heterogeneous structure. As shown in FIG. 1, N-glycans may have, for example, no branches (referred to as a high mannose oligosaccharide) or two, three, or four branches, each of which may or may not terminate with a sialic acid residue. Structures other than those shown in FIG. 1 are possible. Branches may vary in length. For example, a single branch may comprise two or more units (called LacNAc units) comprising N-acetyl glucosamine and galactose or only one LacNAc unit. See FIGS. 1B to 1G. Since sialic acid residues are generally negatively charged, antibodies comprising different numbers of sialic acid residues may be separated on the basis of charge, for example by cation or anion exchange chromatography. Such heterogeneity can also be detected using isoelectric focusing gels, possibly using capillary electrophoresis. Structural variants having different charges due to different numbers of sialic acid residues are referred to herein as "isoforms."

A $CH_2$ domain of all classes of naturally-occurring antibodies can, and usually does, contain an N-linked glycan site. Tao and Morrison (1989), J. Immunol. 143: 2595-2601; Wright and Morrison (1997), Trends in Biotechnol (TIBTECH) 15: 26-32; Riott et al., IMMUNOLOGY, $3^{RD}$ Edition, Mosby, 1993. However, sialic acid is rarely found above trace amounts on recombinant IgG antibodies, suggesting that the $CH_2$ N-glycan site is rarely, if ever, sialylated. Harris et al. (2004), Drug Dev. Res. 62: 137-54. Antibodies of the compositions and methods of the invention may have an N-linked glycan site in their Fc region. Further, antibodies used in the compositions and methods of the invention may have an N-linked glycan site elsewhere, for example in a variable domain, optionally the $V_H$ and/or $V_L$ domain, which may have a variety of N-glycans attached to it that can be sialylated to varying extents. Such variable region glycosylation may affect binding affinity for the antigen, production of the antibody, in vivo half life, and organ targeting. Coloma et al. (1999), J. Immunol. 162: 2162-70; Gala and Morrison (2004), J. Immunol. 172: 5489-94. Antibodies of the IgA, IgE, IgM and IgD isotypes are generally more highly glycosylated than IgG antibodies. Riott et al., supra. Therefore, preparations of monoclonal antibodies of these subclasses are likely to comprise plural structural variants due to differences in glycosylation, including differences in sialylation.

Another way in which structural variants can arise is through differential formation of disulfide bonds. Naturally-occurring antibodies generally contain disulfide bonds, both within and between polypeptide chains. For example, each constant and variable domain of the heavy and light chains comprises highly conserved cysteine residues that can form intra-chain disulfide bonds, each of which encloses a loop of about 60 to 70 amino acids. Further, inter-chain disulfide bonds can exist between the heavy and light chains and between two heavy chains. Most naturally-occurring antibodies can have one or more interchain disulfide bonds between two heavy chains via cysteine residues in the hinge region. Disulfide bonds may form between a variety of different pairs of cysteine residues, giving rise to structural variants with different patterns of disulfide bonds. These structural variants having different disulfide bonding patterns can be separated from each other by, for example, ion exchange high performance liquid chromatography (HPLC) or reversed phase HPLC.

The antibodies of the invention can have particular physical characteristics such as those described in detail in US Patent Application Publication No. US 2005/0004353 A1, which is incorporated by reference herein in its entirety. Among the antibodies described in this application are five antibodies referred to by the numbers 1118, 1118*, 1119, 1121, and 1121*. The sequences of these antibodies and portions thereof are disclosed in the attached sequence listing, and the identity of the sequences in the sequence listing are explained briefly in Table 1. In one aspect, an antibody comprising two heavy and two light chains may be of an IgG, IgM, IgE, IgM, or IgA isotype. If an antibody is an IgG antibody, it can be an IgG1, IgG2, IgG3, or IgG4 antibody. An antibody of the invention can comprise a heavy chain variable region that is at least 80%, optionally at least 85%, 90%, 95%, 98%, or 100%, identical to SEQ ID NO:6, SEQ ID NO:10, SEQ ID NO:14, and/or SEQ ID NO:30. An antibody of the invention can comprise a light chain variable region that is at least 80%, optionally at least 85%, 90%, 95%, 98%, or 100%, identical to SEQ ID NO:8, SEQ ID NO:11, SEQ ID NO:15, and/or SEQ ID NO:31. In another aspect, an antibody of the invention may have particular sequences for its CDRs. For example, an antibody may have a heavy chain CDR3 comprising one of the following amino acid sequences: (a) an amino acid sequence comprising at least 7 of the amino acids of SEQ ID NO:36 in the same order and spacing as they occur in SEQ ID NO:36; or (b) an amino acid sequence comprising SEQ ID NO:37.

As used herein, when a first sequence consists of, for example, 10 amino acids of the sequence RASQSVSSSY (SEQ ID NO: 56), another sequence has 7 amino acids in the "same order and spacing" as they occur in the first sequence if 7 amino acids are identical to those in the sequence and occur in the same relative positions as they occur in the sequence. For example, a sequence RAAAAVSSSY (SEQ ID NO: 57) has 7 amino acids in the same order and spacing as they occur in RASQSVSSSY (SEQ ID NO: 56). In contrast, this is not true for a sequence RASSVSSSY (SEQ ID NO: 58), since it contains an internal deletion relative to RASQSVSSSY (SEQ ID NO: 56), with 3 and 6 amino acids on either side of the deletion. Therefore, it has at most 6 amino acids in the same order and spacing as the first sequence. The shortest possible sequence that could have 7 amino acids in the same order and spacing as in RASQSVSSSY (SEQ ID NO: 56) would be 7 amino acids long, for example SQSVSSS (SEQ ID NO: 59).

"Identity" refers to a comparison between pairs of nucleic acid or amino acid molecules. Methods for determining sequence identity are known. An exemplary, preferred computer program is the Genetics Computer Group (GCG; Madison, Wis.) Wisconsin package version 10.0 program, 'GAP' (Devereux et al., 1984, Nucl. Acids Res. 12: 387; Smith and Waterman, 1981, Adv. Appl. Math. 2:482-489). The preferred default parameters for the 'GAP' program includes: (1) The GCG implementation of a unary comparison matrix (containing a value of 1 for identities and 0 for non-identities) for nucleotides, and the weighted amino acid comparison matrix of Gribskov and Burgess, Nucl. Acids Res. 14:6745, 1986, as described by Schwartz and Dayhoff, eds., Atlas of Polypeptide Sequence and Structure, National Biomedical Research Foundation, pp. 353-358, 1979; or other comparable comparison matrices; (2) a penalty of 30 for each gap and an additional penalty of 1 for each symbol in each gap for amino acid sequences, or penalty of 50 for each gap and an additional penalty of 3 for each symbol in each gap for nucleotide sequences; (3) no penalty for end gaps; and (4) no maximum penalty for long gaps. In determining identity using GAP, two sequences can be aligned over part or all of their length. This aligned portion is referred to herein as an "identity region."

"Substantially similar" polypeptides, as meant herein, are at least about 90%, identical to each other in amino acid sequence and maintain or alter in a desirable manner the biological activity of the unaltered polypeptide.

A "recombinant protein" or "recombinant antibody" is a protein or antibody produced by host cells that is not naturally produced by the cells. The host cells produce the recombinant protein or antibody as a result of the introduction of nucleic acid sequences that allow expression of the protein or antibody into host cells using methods of "genetic engineering," such as viral infection with a recombinant virus, transfection, transformation, bombardment with microprojectiles coated with nucleic acids, or electroporation, among other methods of introducing nucleic acids into cells.

In some embodiments, an antibody may bind specifically to IFN-γ, optionally human IFN-γ. The antibody may also bind to other antigens, which may or may not be proteins. The antibodies contained in the compositions of the invention may be identical or substantially similar to a naturally-occurring antibody and/or may, or may not, be a recombinant protein. Optionally, the antigen to which the antibody binds may comprise a human polypeptide, a fragment thereof, or a substantially similar polypeptide that is at least 10 amino acids in length.

Generally, the methods and compositions of the invention are useful for stabilizing antibodies that bind to any molecule, including, for example, to all or part of one of the following polypeptides: a flt3 ligand (as described in International Application WO 94/28391, incorporarted herein by reference), a CD40 ligand (as described in U.S. Pat. No. 6,087,329 incorporated herein by reference), erythropoeitin, thrombopoeitin, calcitonin, Tek, Tek-delta, Tie-2, leptin, IL-2, angiopoietin-2 (as described by Maisonpierre et al. (1997), Science 277(5322): 55-60, incorporated herein by reference), Fas ligand, ligand for receptor activator of NF-kappa B (RANKL, as described in International Application WO 01/36637, incorporated herein by reference), tumor necrosis factor (TNF)-related apoptosis-inducing ligand (TRAIL, as described in International Application WO 97/01633, incorporated herein by reference), thymic stroma-derived lymphopoietin, granulocyte colony stimulating factor (G-CSF), granulocyte-macrophage colony stimulating factor (GM-CSF, as described in Australian Patent No. 588819, incorporated herein by reference), mast cell growth factor, stem cell growth factor (described in e.g. U.S. Pat. No. 6,204,363, incorporated herein by reference), epidermal growth factor, keratinocyte growth factor, megakaryote growth and development factor, RANTES, growth hormone, insulin, insulinotropin, insulin-like growth factors, parathyroid hormone, interferons including α interferons, γ interferon, and consensus interferons (such as those described in U.S. Pat. Nos. 4,695,623 and 4,897,471, both of which are incorporated herein by reference), nerve growth factor, brain-derived neurotrophic factor, glial cell-derived neurotrophic factors including GDNF, synaptotagmin-like proteins (SLP 1-5), neurotrophin-3, glucagon, interleukins 1 through 18, colony stimulating factors, lymphotoxin-β, tumor necrosis factor (TNF), leukemia inhibitory factor, oncostatin-M, and various ligands for cell surface molecules ELK and Hek (such as the ligands for eph-related kinases or LERKS). Descriptions of polypeptides that can be produced according to the inventive methods may be found in, for example, *Human Cytokines: Handbook for Basic and Clinical Research, Vol. II* (Aggarwal and Gutterman, eds. Blackwell Sciences, Cambridge, Mass., 1998); *Growth Factors: A Practical Approach* (McKay and Leigh, eds., Oxford University Press Inc., New York, 1993); and *The Cytokine Handbook* (A. W. Thompson, ed., Academic Press, San Diego, Calif., 1991), all of which are incorporated herein by reference.

Other antigens to which the antibodies used in the compositions or methods of the invention may bind include all or part of the amino acid sequence of a receptor for any of the above-mentioned polypeptides or an antagonist to such a receptor, including the following: both forms of tumor necrosis factor receptor (TNFR, referred to as p55 and p75, as described in U.S. Pat. No. 5,395,760 and U.S. Pat. No. 5,610, 279, both of which are incorporated herein by reference, including the fusion protein etanercept, which is marketed as ENBREL®), Interleukin-1 (IL-1) receptors (types I and II; described in EP Patent No. 0 460 846, U.S. Pat. No. 4,968, 607, and U.S. Pat. No. 5,767,064, all of which are incorporated herein by reference), IL-1 receptor antagonists (such as those described in U.S. Pat. No. 6,337,072, incorporated herein by reference), IL-1 antagonists or inhibitors (such as those described in U.S. Pat. Nos. 5,981,713, 6,096,728, and 5,075,222, all of which are incorporated herein by reference) IL-2 receptors, IL-4 receptors (as described in EP Patent No. 0 367 566 and U.S. Pat. No. 5,856,296, both of which are incorporated by reference), IL-15 receptors, IL-17 receptors, IL-18 receptors, granulocyte-macrophage colony stimulating factor receptor, granulocyte colony stimulating factor receptor, receptors for oncostatin-M and leukemia inhibitory factor, receptor activator of NF-kappa B (RANK, described in WO 01/36637 and U.S. Pat. No. 6,271,349, both of which are incorporated by reference), osteoprotegerin (described in e.g. U.S. Pat. No. 6,015,938, incorporated by reference), receptors for TRAIL (including TRAIL receptors 1, 2, 3, and 4), and receptors that comprise death domains, such as Fas or Apoptosis-Inducing Receptor (AIR).

Other antigens to which the antibodies used in the compositions or methods of the invention may bind comprise all or part of the amino acid sequences of differentiation antigens (referred to as CD polypeptides) or their ligands or polypeptides substantially similar to either of these. Such antigens are disclosed in *Leukocyte Typing VI (Proceedings of the VIth International Workshop and Conference*, Kishimoto, Kikutani et al., eds., Kobe, Japan, 1996, which is incorporated by reference). Similar CD polypeptides are disclosed in subsequent workshops. Examples of such antigens include CD22, CD27, CD30, CD39, CD40, and ligands thereto (CD27 ligand, CD30 ligand, etc.). Several of the CD antigens are members of the TNF receptor family, which also includes 41BB and OX40. The ligands are often members of the TNF family, as are 41BB ligand and OX40 ligand. Accordingly, members of the TNF and TNFR families may also be antigens to which the antibodies stabilized by the methods of the invention can bind.

The antibodies stabilized by the methods and compositions of the invention may also bind to enzymatically active polypeptides or their ligands. Examples include polypeptides comprising all or part of one of the following polypeptides or their ligands or a polypeptide substantially similar to one of these: metalloproteinase-disintegrin family members, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, TNF-alpha Converting Enzyme, ligands for any of the above-mentioned enzymes, and numerous other enzymes and their ligands.

The compositions and methods of the invention may further be used to stabilize antibodies that bind to the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1α, IL-1β, IL-2, IL-3, IL-7, IL-4, IL-5, IL-8, IL-10, IL-2 receptor, IL-4 receptor, IL-6 receptor, IL-13 receptor, IL-18 receptor subunits, PDGF-β and analogs thereof (such as those described in U.S. Pat. Nos. 5,272,064 and 5,149,792), VEGF, TGF, TGF-β2, TGF-β1, EGF receptor (including those described in U.S. Pat. No. 6,235,883 B1, incorporated by reference) VEGF receptor, hepatocyte growth factor, osteoprotegerin ligand, interferon gamma, B lymphocyte stimulator (BlyS, also known as BAFF, THANK, TALL-1, and zTNF4; see Do and Chen-Kiang (2002), Cytokine Growth Factor Rev. 13(1): 19-25), C5 complement, IgE, tumor antigen CA125, tumor antigen MUC1, PEM antigen, LCG (which is a gene product that is expressed in association with lung cancer), HER-2, a tumor-associated glycoprotein TAG-72, the SK-1 antigen, tumor-associated epitopes that are present in elevated levels in the sera of patients with colon and/or pancreatic cancer, cancer-associated epitopes or polypeptides expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA4, B2 integrins, c-MET, MET, TRAIL receptors 1, 2, 3, and 4, RANK, RANK ligand, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, L-selectin, Respiratory Syncitial Virus, human immunodeficiency virus (HIV), hepatitis B virus (HBV), *Streptococcus mutans*, and *Staphlycoccus aureus*.

The antibodies stabilized by the methods and compositions of the invention may be anti-idiotypic antibodies, including anti-idiotypic antibodies against: an antibody targeted to the tumor antigen gp72; an antibody against the ganglioside GD3; an antibody against the ganglioside GD2; or antibodies substantially similar to these.

A pharmaceutical composition of the invention is considered to be "stable," as meant herein, if the antibody essentially retains its starting physical and chemical structure and biological activity after storage at 4° C. for 2 years. Physical structure and biological activity can be measured in a variety of ways, for example, by size exclusion chromatography, reversed phase chromatography, an A549 assay, and/or fluorescence emission, as explained in Example 2, among many possible assays. A method or composition is "stabilizing" if it promotes the substantial retention of the characteristics of the starting material as measured by at least one of these methods.

A "lyophilized" pharmaceutical composition, which is a freeze-dried composition, can be described as containing certain molecules in certain concentrations and/or being at a certain pH. As meant herein, this means that when the lyophilized composition is resuspended in the amount of diluent recommended for use, it contains the described molecules at the described concentrations and has the described pH.

A pharmaceutical composition of the invention comprises at least a buffering agent and an antibody and, optionally, at least one stabilizing compound, such as, for example, a sugar, a carbohydrate, a salt, an amino acid, or a surfactant. One of skill in the art is aware that components other than a buffering agent are often contained within a pharmaceutical composition comprising an antibody. For example, a pharmaceutical composition is often isotonic, that is, it has a concentration of solutes such that it will not cause osmotic volume changes of cells if cells were immersed in it. An isotonic composition generally has an osmotic pressure from about 250 to about 350 mOsm. Various kinds of solutes, for example sugars, polysaccharides, carbohydrates, or salts, can be used to make a solution isotonic, i.e., to tonicify it.

The buffering agent can be, for example, any of the following or salts thereof: succinate, histidine, acetate, gluconate, citrate, tartaric acid, malic acid, lactic acid, organic acids, Tris, bis-Tris, mono-Tris, pyrophosphoric acid, phosphate, proprionate, carbonic acid, sulphate, 3-(N-morpholino)propanesulfonic acid (MOPS), 4-(2-hydroxyethyl)-1-piperazineethanesulfonic acid (HEPES), N-tris(Hydroxymethyl) methylglycine (TRICINE), N,N-bis(2-hydroxyethyl)glycine (BICINE), N-(2-acetamido)iminodiacetic acid (ADA), N-(2-Acetamido)-2-aminoethanesulfonic acid (ACES), imidazole, aminoethanesulfonate or a derivative thereof (such as tris (hydroxymethyl)-methyl-2-aminoethane sulfonate, also known as TES, or 2-morpholinoethanesulfonic acid, also known as MES), aminopropanesulfonate or a derivative thereof, oxalic acid, fumaric acid, and diethanolamine. The salts of the above-mentioned buffering agents may include sodium, magnesium, calcium, chloride, and/or potassium salts, among others. For example, sodium phosphate, potassium phosphate, histidine chloride, Tris-HCl, sodium acetate, potassium acetate, sodium succinate, potassium succinate, are included within the scope of the buffering agents contemplated herein. The pH of the composition can be from about 3.5 to about 9, optionally from about 5 to about 7, from about 5 to about 6.5, from about 4.5 to about 6.5, from about 4.5 to about 5.5, from about 5.5 to about 6.5, from about 5.7 to about 6.5, from about 5.7 to about 6.3, about 5, or about 6.

The concentration of the buffering agent can be at least about 0.5 mM and not more than about 300 mM. In some embodiments, the concentration of the buffering agent may be from about 1 mM to about 100 mM, or from about 5 mM to about 50 mM, or from about 5 mM to about 15 mM.

A composition of the invention may comprise a salt, a carbohydrate, a surfactant and/or a sugar, among other possibilities, which may serve to tonicify the formulation. Exemplary salts include sodium, potassium, magnesium, and calcium salts such as, for example, sodium chloride, potassium chloride, magnesium chloride, and calcium chloride, among others. Salts can be used at concentrations of at least about 1, 5, or 10 mM and not more than about 300, 200, 100, 50, or 30 mM. Concentrations from about 50 mM to about 175 mM and from about 75 mM to about 150 mM are contemplated.

Exemplary sugars, polysaccharides, and/or carbohydrates include sucrose, dextrose, sorbitol, mannitol, xylitol, erythritol, threitol, glycerol, polyethylene glycol, sugar acids, glucose, fructose, mannose, maltose, maltotriose, lactose, lactulose, arabinose, xylose, ribose, rhamnose, galactose, trehalose, sorbose, melezitose, raffinose, polysaccharides such as dextran, alginates, hyaluronic acid, or cellulose, among others. Such sugars, polysaccharides, and/or carbohydrates can be used at various concentrations including, for example, from about 0.001% to about 25%, from about 1% to about 20%, or from about 1% to about 10%.

Exemplary surfactants include polysorbates, including polysorbate 20 and polysorbate 80, and polyaxmers, including polyaxmer 188. These can be used at concentrations from about 0.0001% to about 0.1%, optionally from about 0.001% to about 0.01%.

The pH and/or the specific buffering agent of a pharmaceutical composition comprising an antibody can affect the stability of the antibody. Different pHs and/or buffering agents can stabilize different antibodies or different structural variants or combinations of structural variants of a single antibody. Various physical and biological properties of an antibody can be measured. For example, size exclusion chromatography can determine whether an antibody has been cleaved into smaller-than-full-size pieces or has aggregated into dimers or higher order aggregates. Reversed phase chromatography can also provide information on whether an antibody has been cleaved into smaller fragments. In addition, the wavelength of maximal fluorescent emission (which can be expressed as a ratio between two wavelengths) can be determined by fluorescence spectroscopy. Changes in this wavelength can indicate a change in the secondary or tertiary structure of an antibody. Changes in pH may affect different aspects of physical structure in different ways. Moreover, effects on biological activity may or may not show a clear relationship to effects on physical structure. Biological activity can be measured by binding to an antigen, for example using an ELISA assay, using a cell-based in vitro assay, or using an in vivo assay.

Specific binding to interferon gamma can be measured essentially as described by Fishwild et al., 1996, *Nature Biotechnology* 14: 845-851. Briefly, microtiter plates can be coated using about 50 µl/well of a solution of IFN-γ at a concentration of about 1-2 µg/ml in phosphate buffered saline (PBS) and blocked using 5% chicken serum in PBS. The plates can then be sequentially incubated with the antibodies being tested for binding and with antibodies that will bind to the antibodies being tested (for example, an anti-human IgG1 Fc antibody would bind to human full length IgG1 test antibodies) conjugated to horseradish peroxidase. Finally, a detectable horseradish peroxidase substrate such as 2,2'-azino-bis [3-ethylbenziazolene-6-sulfonic acid] (ABTS) can be added, and absorbance at 490 and 415 nm can be measured. Absorbance at 490 nm is subtracted from that at 415 nm. A pH and/or a buffering agent that maximizes the amount of antibody having biological activity, binding activity, or the amount of antibody in monomer form is desirable. Plates can be washed extensively between steps with 0.5% Tween 20 in PBS. This well-known assay (ELISA) for antigen binding can be used to test for binding to almost any antigen.

The pharmaceutical compositions of the invention can be liquid, lyophilized, or frozen compositions. A liquid or frozen composition may or may not have been previously lyophilized. A liquid composition may or may not have been frozen.

IFN-γ is an important positive regulator of some aspects immune function. Inhibition of the biological activity of interferon gamma can therefore be a way to counteract various autoimmune and/or inflammatory diseases. Various IFN-γ antibodies that can inhibit its biological activity are known in the art. US Patent Application Nos. 2005/0004353 and 2003/0049647. Such antibodies can be useful in treating various autoimmune and/or inflammatory diseases. See e.g., U.S. Pat. Nos. 6,036,956, 6,333,032, and 6,558,661.

Numerous methods of producing and purifying antibodies are well-known in the art, and any of these may be used to produce antibodies used in the methods and compositions of the invention. Exemplary methods are described in, e.g., US Patent Application No. 2005/0004353. For example, the antibodies used in the methods and compositions of the invention may be produced by inoculating a mammal with an antigen and harvesting polyclonal antibodies against the antigen from the blood. Alternatively, spleen cells from the inoculated mammal can be harvested and fused to immortalized cells to produce hybridoma lines that produce and secrete monoclonal antibodies. Such lines can be screened for lines that produce antibodies that bind to the antigen. Further, nucleic acids encoding the antibody may be cloned in bacteria. In some embodiments, the antibodies can be produced by the bacteria. Alternatively, DNA encoding the antibody can be introduced into a eukaryotic host cell, such as a yeast, mammalian, plant, or insect cell, and the antibody can be produced by the mammalian cell. If the cell is a mammalian cell, it can be a Chinese hamster ovary (CHO) cell or a VERO, BHK, HeLa, CV1 (including Cos), MDCK, 293, 3T3, myeloma (e.g., NSO, NS1), PC12, or WI38 cell.

Antibodies can be purified by any one of or a combination of the many methods known in the art of protein purification. See e.g., Protein Purification Applications, A Practical Approach, Harris and Angal, eds., IRL Press at Oxford University Press, 1990; Wheelwright, Protein Purification: Design and Scale up of Downstream Processing, Hanser Publishers, 1991; Scopes, Protein Purification, Principles and Practice, Third Edition, Springer Verlag, 1993; Gagnon, Purification Tools for Monoclonal Antibodies, Validated Biosystems, Inc., 1996. One very common purification method for antibodies is Protein A chromatography.

The compositions of the invention can be used as treatments for a variety of disorders. For example, antibodies that bind to interferon gamma can be used to treat lupus erythematosus, and various autoimmune diseases including multiple sclerosis, rheumatoid arthritis, ankylosing spondylitis, juvenile rheumatoid arthritis, psoriatic arthritis, and inflammatory bowel diseases such as Crohn's disease and ulcerative colitis. See U.S. Pat. Nos. 6,036,956, 6,333,032, and 6,558,661. Many other uses of other antibodies are known in the art, such as, for example, the use of anti-TNF receptor antibodies to treat rheumatoid arthritis or the use of anti-EGF receptor antibodies to treat cancer. Antibodies may be used to treat cancers including, for example, osteosarcomas, glioblastomas, gliomas, melanomas, and meningiomas, and lung, breast, head and neck, bladder, ovarian, skin, prostate, cervical, gastric, renal cell, pancreatic, colorectal, endometrial, and esophageal cancers. As used herein, "gastrointestinal cancer" encompasses gastric, esophageal, pancreatic, and colorectal cancers. Also treatable using the methods of the invention are hematologic cancers.

Treatment of a disease encompasses alleviation of at least one symptom of the disorder, a reduction in the severity of the disease, or the delay or prevention of progression to a more serious disease that occurs with some frequency following the treated condition. Treatment need not mean that the disease is totally cured. A useful therapeutic agent needs only to reduce the severity of a disease, reduce the severity of symptom(s) associated with the disease or its treatment, or delay the onset of a more serious disease that can occur with some frequency following the treated condition. As meant herein, severity of disease can be assessed by methods known in the art and used to assess disease severity in clinical settings.

The compositions can be administered by any suitable route. They may be injected, for example, subcutaneously, intravenously, intraarticularly, intramuscularly, intraarterially, intraperitoneally, or directly into an affected area of the body such as, for example, a joint or a tumor. The composition may be administered by infusion or by bolus injection. In some embodiments, a composition may be administered by absorption through a mucus membrane, such as nasal, rectal, gastric, or vaginal administration or by inhalation. They may be administered transdermally, as suppositories inserted into a body cavity, or as eyedrops. Alternatively, they may be taken orally.

The compositions of the invention can be administered at a "therapeutically effective dose," that is, at any dosage, frequency, and duration that can be effective to treat the condition being treated. One of skill in the art will realize that this depends on the molecular nature of the antibody, the in vivo concentration of the antigen to which it binds, and the nature and severity of the disorder being treated, among other considerations. Treatment may be continued as long as necessary to achieve the desired results. Therapeutic molecules of the invention can be administered as a single dosage or as a series of dosages given periodically, including multiple times per day, daily, every other day, twice a week, three times per week, weekly, every other week, monthly, every other month, every 10 weeks, and every 12 weeks among other possible dosage regimens. The periodicity of treatment may or may not be constant throughout the duration of the treatment. For example, treatment may initially occur at weekly intervals and later occur every other week. Treatments having durations of days, weeks, months, or years are encompassed by the invention. Treatment may be discontinued and then restarted. Maintenance doses may be administered after an initial treatment. The compositions of the invention can be administered either alone or in combination other treatments, especially treatments that are normally administered to treat the disease.

Dosage may be measured as milligrams per kilogram of body weight (mg/kg) or as milligrams per square meter of skin surface (mg/m$^2$) or as a fixed dose, irrespective of height or weight. All of these are standard dosage units in the art. A person's skin surface area is calculated from her height and weight using a standard formula. Each dosage can be, for example, from about 0.001 mg/kg to about 50 mg/kg, from about 0.01 mg/kg to about 50 mg/kg, from about 0.02 to about 50 mg/kg of patient body weight. Optionally, the dosage can be from about 0.05 to about 20 mg/kg, from about 0.01 mg/kg to about 10 mg/kg, or from about 0.1 to about 10 mg/kg, or about 0.01 mg/kg, about 0.1 mg/kg, or about 1.0 mg/kg.

One of skill in the art is aware that the route of administration can influence the dosage and concentration of the composition of the invention. For example, if the composition is administered subcutaneously, the volume that can be administered may be limited to about 5 ml or less, optionally about 3, 2, or 1 ml or less. Thus, the concentration of the composition may be influenced by a limitation on volume. On the other hand, if the composition is infused intravenously, a larger volume may be injected, and the composition may thus be less concentrated.

In some embodiments, the compositions and methods of the invention require that the antibodies be at a concentration of less than about 50 mg/ml, optionally, less than or equal to about 45, 40, 35, 30, 25, 10, 5, 1, or 0.1 mg/mL. Alternatively, or in addition, the compositions and methods of the invention may require that the antibodies be at a concentration of greater than or equal to about 0.01, 0.1, 1, 5, 10, or 50 mg/ml, optionally, greater than or equal to about 75 mg/ml, about 100 mg/ml, 150 mg/ml, 200 mg/ml, or 250 mg/ml. One of skill in the art is aware that compositions of higher or lower concentrations may be more appropriate for certain different routes of administration for particular antibodies. Further, antibody concentration can affect what formulation may be optimal for an antibody. Thus, different formulations may be appropriate for the same antibody at different concentrations. Effective doses required for different antibodies may be very different, depending on factors such as binding affinity, dissociation constant, and the abundance of the antigen to which the antibody binds. Therefore, compositions having different concentrations of antibodies would be appropriate in different cases. Further, when an antibody is administered subcutaneously, the volume that can be administered in this way is limited. Therefore, an antibody composition that is administered subcutaneously may be more concentrated than a composition of the same antibody that is administered by, for example, intravenous infusion.

The invention having been described, the following examples are offered by way of illustration, and not limitation. All references cited herein are incorporated by reference in their entirety.

EXAMPLES

Example 1

Purification of Isoforms

In the following experiments, the antibody used was a full length human IgG1 antibody against human IFN-γ comprising two heavy and two light chains produced by cultured mammalian cells (CHO cells), and its heavy and light chain amino acid sequences are disclosed SEQ ID NO:17 and SEQ ID NO:18, respectively. The heavy chain amino acid sequence had N-glycan sites at amino acids 28 and 297 of SEQ ID NO:17, in the $V_H$ and $CH_2$ regions, respectively. In this example, isoforms having different numbers of sialic acids per molecule were isolated. Bulk antibody material refers to filtered purified bulk (referred to herein as FPB) antibody preparations, which have been purified using several column chromatography steps and in which the various structural variants, including isoforms, have not been separated from each other.

Figure 2:
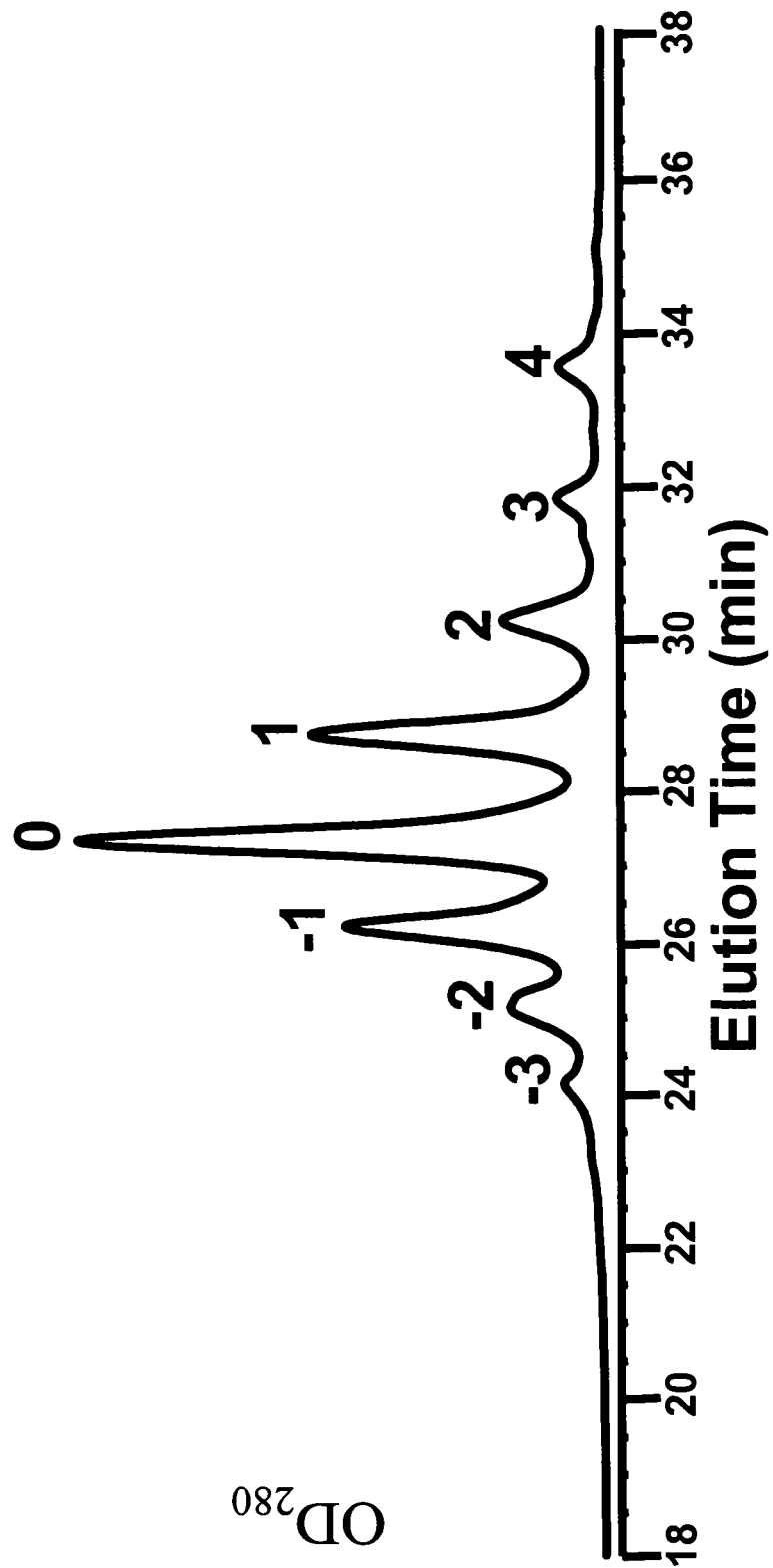
FIG. 2 shows an elution profile showing optical density at 280 nanometers ($OD_{280}$) from a cation exchange column onto which a purified preparation of an antibody having an N-glycan site in its heavy chain variable region has been loaded. At least eight different charged variants or isoforms were detected.

Bulk antibody material (FPB) was purified in three column chromatography steps from cultured mammalian cell supernatants and applied to a weak cation exchange (CEX) column, which separates molecules according to charge, and eluted using a mobile phase containing 10 mM sodium phosphate, pH 7.2 containing from 0-250 mM NaCl. A profile of this column is shown in FIG. 2. Fractions comprising isoforms, which contain different numbers of sialic acid residues, were collected and concentrated. Concomitantly, the fractions were buffer-exchanged to 10 mM sodium acetate, pH 5. The purity of each of the final concentrated isoform solution was determined by its corresponding CEX high performance liquid chromatography (HPLC) profile, which contained predominantly one CEX peak with elution time comparable to that prior to purification. The purity percentage was quantified by the area of the main CEX peak divided by the total area under all peaks including any minor CEX peaks detected at both 215 and 280 nm. Typical purity of each isoform solution was 93% to 96%. Table 2. The absorbance of each purified isoform solution was measured at 280 nm, and the concentration of each isoform solution was derived from this. Table 2 (below) shows the percent purity, the concentration, and the total amount of each purified isoform solution, as well as the percent of total FPB which each isoform comprises. This last number is calculated by dividing the area under each peak detected in the cation exchange column by the sum of the areas under all peaks. Peaks −3, +3, and +4, which are not included in Table 2, together comprise the remaining 6% of total FPB.

TABLE 2

| sample | % purity | Concentration (mg/mL) | Total amount (mg) | % of total FPB |
|---|---|---|---|---|
| Peak −2 | 95.7 | 108 | 15.1 | 10 |
| Peak −1 | 96.3 | 248 | 72.0 | 19 |
| Peak 0 | 96.1 | 657 | 256.2 | 36 |
| Peak 1 | 96.2 | 477 | 128.8 | 20 |
| Peak 2 | 92.8 | 173 | 22.5 | 9 |

Example 2

Formulation of the Isoforms and FPB at Different pH's and Assessment of their Stability The following experiment compares the stability of the purified isoforms and of FPB at a variety of pHs at both 4° C. and 37° C. Each of the purified isoforms, along with the FPB, was formulated in the following buffers at a final concentration of 1 mg/mL: 10 mM sodium acetate, pH 4; 10 mM sodium acetate, pH 5; 10 mM histidine, pH 6; 10 mM sodium phosphate, pH 7; and 10 mM sodium phosphate, pH 8. All samples also contained 5% (w/v) sorbitol. All formulated antibody solutions and corresponding placebos, i.e., formulated solutions lacking antibodies, were sterilized by filtration through 0.2 μm membranes prior to being aliquoted into sterile microtubes with o-ring caps, which were used to prevent evaporation. The total volume for each sample was from about 300 μL to 350 μL. One set of formulated antibody solutions and corresponding placebos was incubated at 4° C., while another was incubated at 37° C., both under static conditions.

The biophysical and biochemical stability of each sample was evaluated at time points 0, 2 weeks, 1 month, and 3 months using size exclusion chromatography (SEC), reversed phase HPLC, and fluorescence spectroscopy, among other techniques. Analytical ultracentrifugation (AUC) was used to determine the approximate molecular weight of the HMW species detected by SEC. Bioactivity was assessed on the samples that had been incubated for 3 months in formulation of pH 5. Each formulated protein solution, as well as each placebo, that had been stored at 4° C. and 37° C. was inspected for insoluble species and clarity. After 3 months at either 4° C. or 37° C., all samples, both with and without antibodies, remained colorless, translucent, and without particulate matter.

Figure 3:
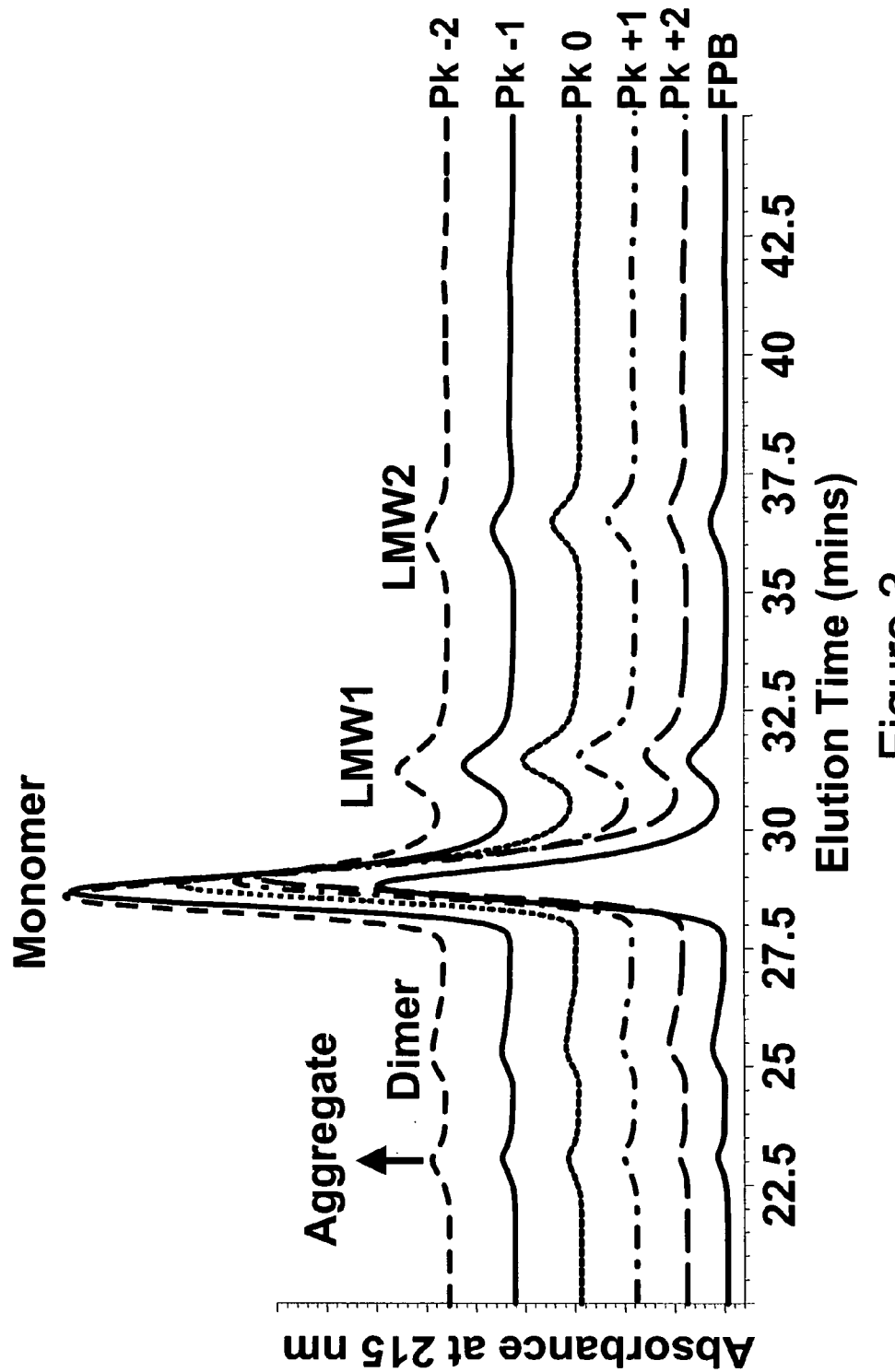
FIG. 3 shows a set of overlaid size exclusion chromatography (SEC) $OD_{215}$ column profiles from samples formulated in 10 mM sodium phosphate, pH 8, 5% sorbitol after 3 months storage at 37° C.

Using two SEC columns connected in tandem, SEC provided quantification of the levels of monomer (in this case, tetrameric antibodies having two heavy and two light chains), high molecular weight (HMW) (e.g. dimers and aggregates), and low molecular weight (LMW) species. Each column sample was 20 μg at concentration of 1 mg/mL. Multiple samples were run to ensure reproducibility. Detection wavelengths were set at 215 and 280 nm. In most of the samples, most of the material eluted as a single, dominant peak in SEC. This peak contains monomers. In this context, where the antibody is an IgG antibody, monomers are tetrameric antibodies comprising two heavy chains and two light chains with a molecular weight of approximately 150,000 daltons. However, four noticeable peaks other than the main monomer peak were observed among samples from formulations incubated at 37° C. SEC column profiles of samples containing FPB and different purified individual isoforms formulated at pH 8 in 10 mM sodium phosphate, 5% sorbitol and stored at 37° C. for three months are shown in FIG. 3. All of these samples showed a predominant main peak, containing monomers, and two higher molecular weight plus two lower molecular weight peaks. The two low molecular weight species were designated LMW1 and LMW2. The highest molecular weight species was designated as aggregates, and the next-eluting species was designated as dimers (meaning dimers comprising two tetrameric antibodies). These designations were based on molecular weights determined by analytical ultracentrifugations (AUC) and SDS-PAGE. AUC was used to determine the approximate molecular weight of the HMW species detected by SEC under non-reducing conditions. SDS-PAGE under reducing conditions, i.e., under condition in which the disulfide bonds are broken, was used to assess the size of the HMW species.

Figure 4A:
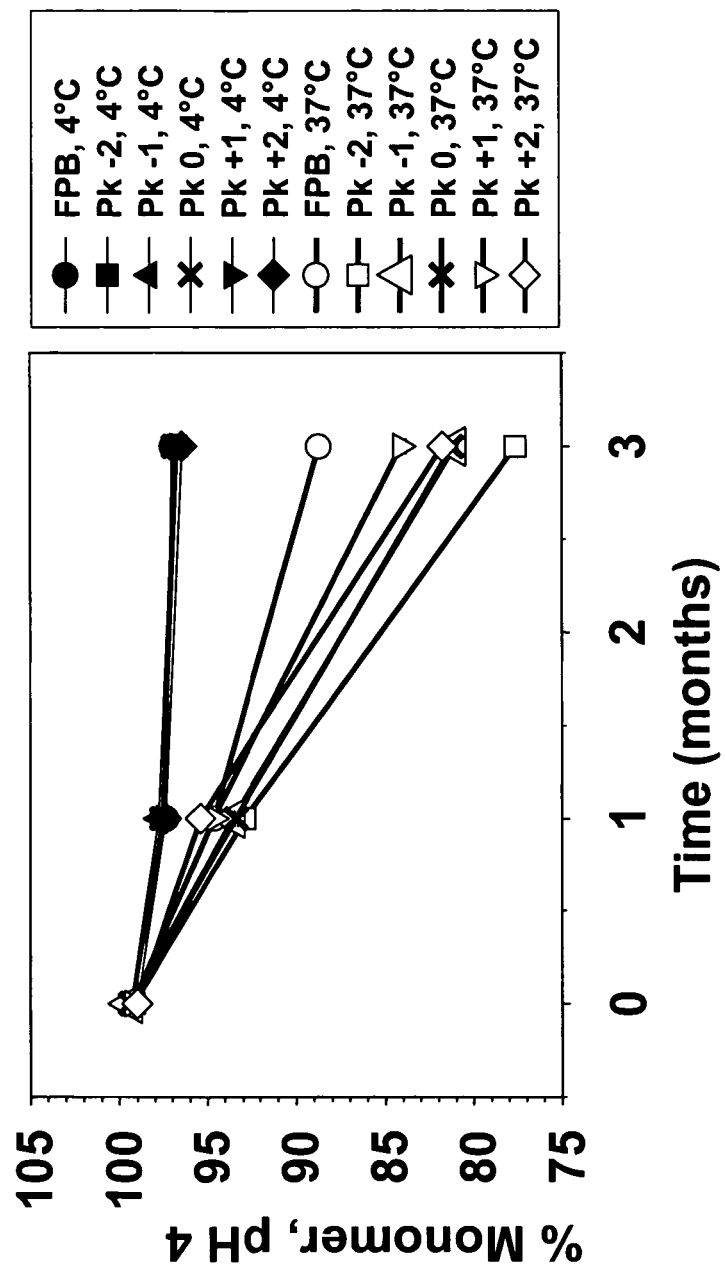
FIG. 4 shows the percent of total antibody that is in monomer form as detected by native SEC for purified isoform Peaks −2, −1, 0, +1, and +2 and FPB as a function of time, storage temperature, and pH. Each panel shows the percent monomer at time points from zero to three months at both 4° C. (filled symbols) and 37° C. (open symbols) for pH 4 (FIG. 4A), pH 5 (FIG. 4B), pH 6 (FIG. 4C), pH 7 (FIG. 4D), and pH 8 (FIG. 4E). The samples were formulated as follows: pH 4, 5% sorbitol 10 mM sodium acetate; pH 5, 5% sorbitol 10 mM sodium acetate; pH 6, 5% sorbitol, 10 mM histidine; and pH 7 and 8, 5% sorbitol, 10 mM sodium phosphate.
Figure 4B:
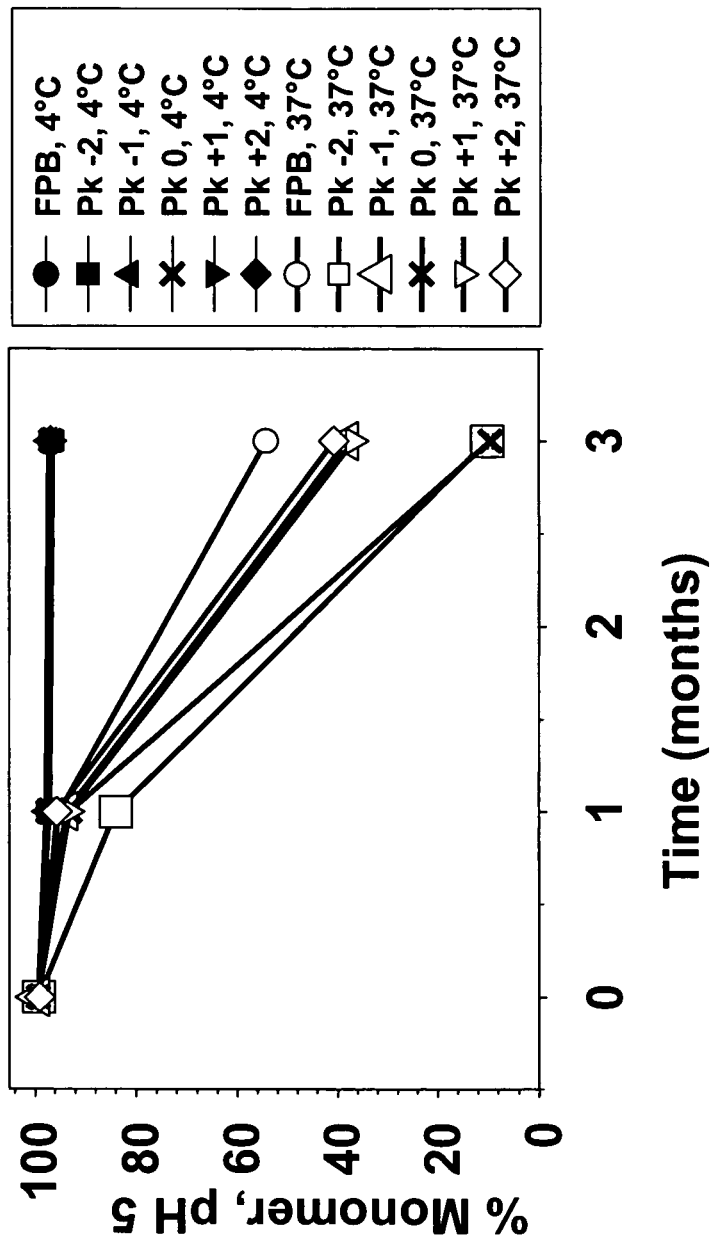

FIGS. 4A-4E show the percent of the total material which remained as monomers as measured by SEC at each time point. In all samples incubated at 4° C. at all pHs, most of the material remained as antibody monomers for at least three months. However, samples stored at 37° C. showed considerable loss of monomeric species, particularly among pH 5 samples (FIG. 4B). Isoform Peak −2 and peak 0 material stored at 37° C. at pH 5 lost more monomers than any other samples, and isoform Peak −2 and Peak 0 samples were among the lower scoring samples for percent monomer at most other pHs tested. As a group and individually, pH 5 samples at 37° C. showed much more loss of monomers than samples incubated at any other pH and temperature. As a group and individually, samples incubated at pH 6 at 37° C. contained higher percentages of monomers than any other 37° C. samples. FIGS. 4A-4E.

Figure 4C:
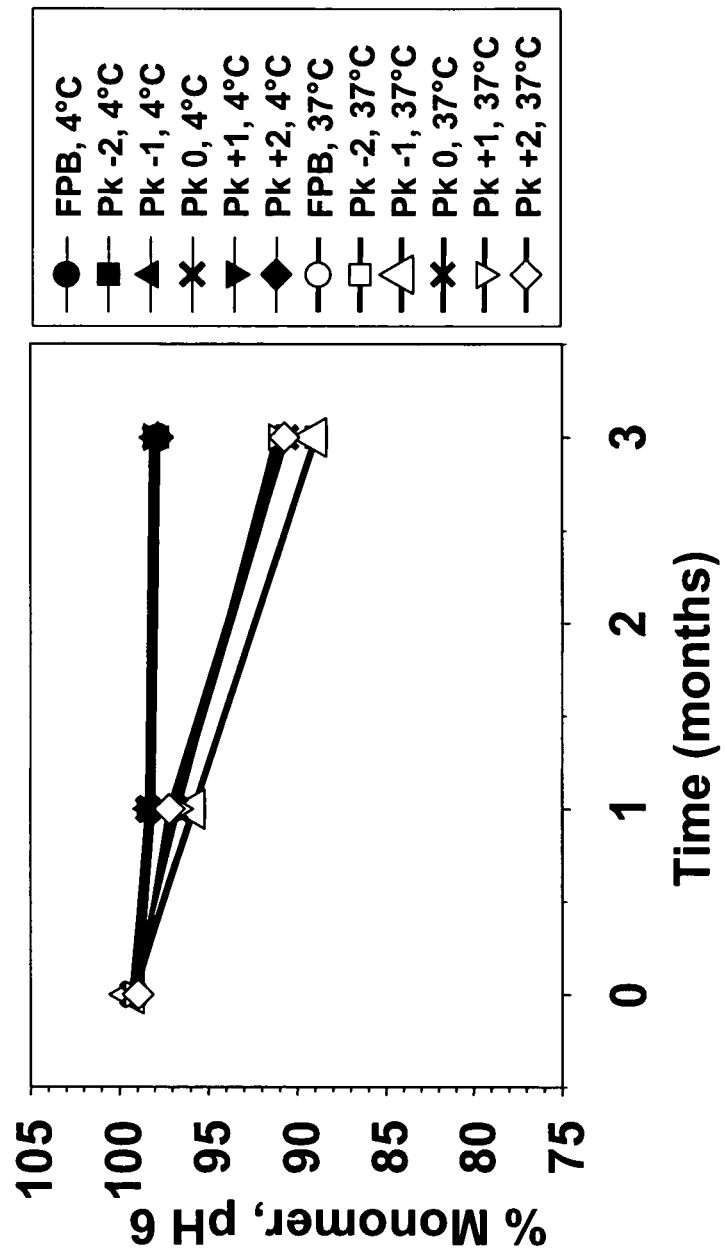
Figure 4D:
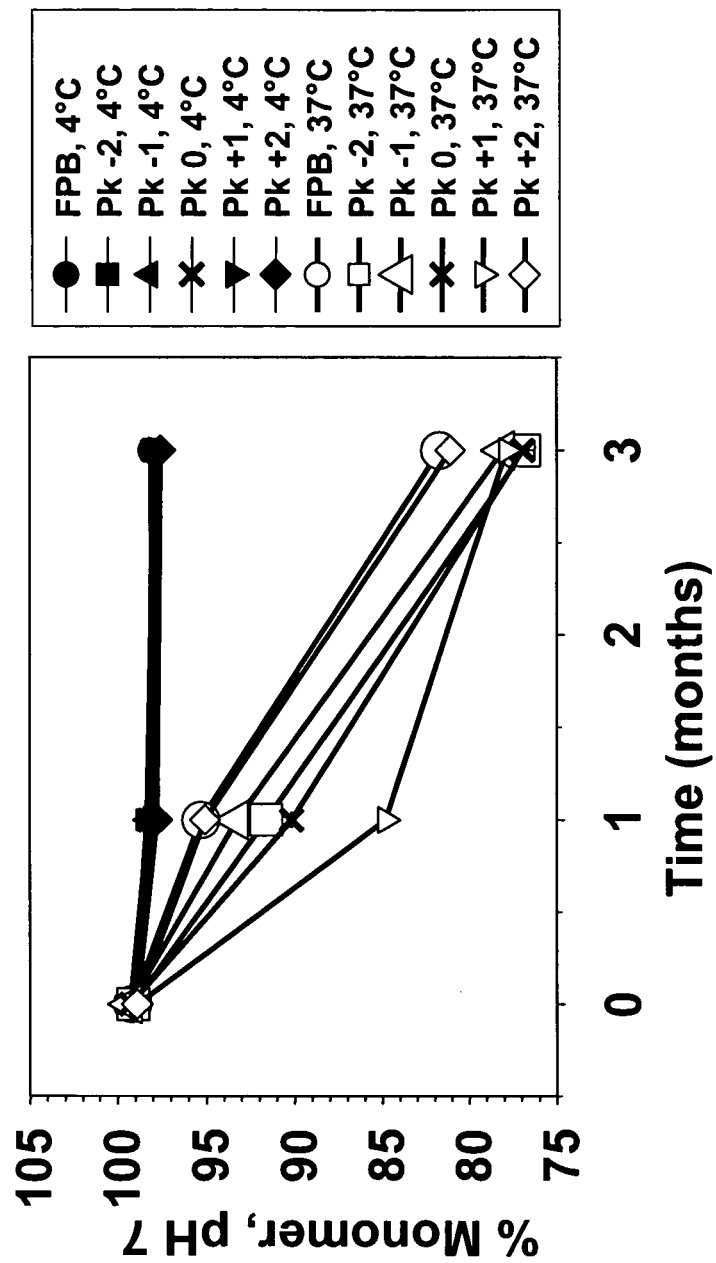
Figure 4E:
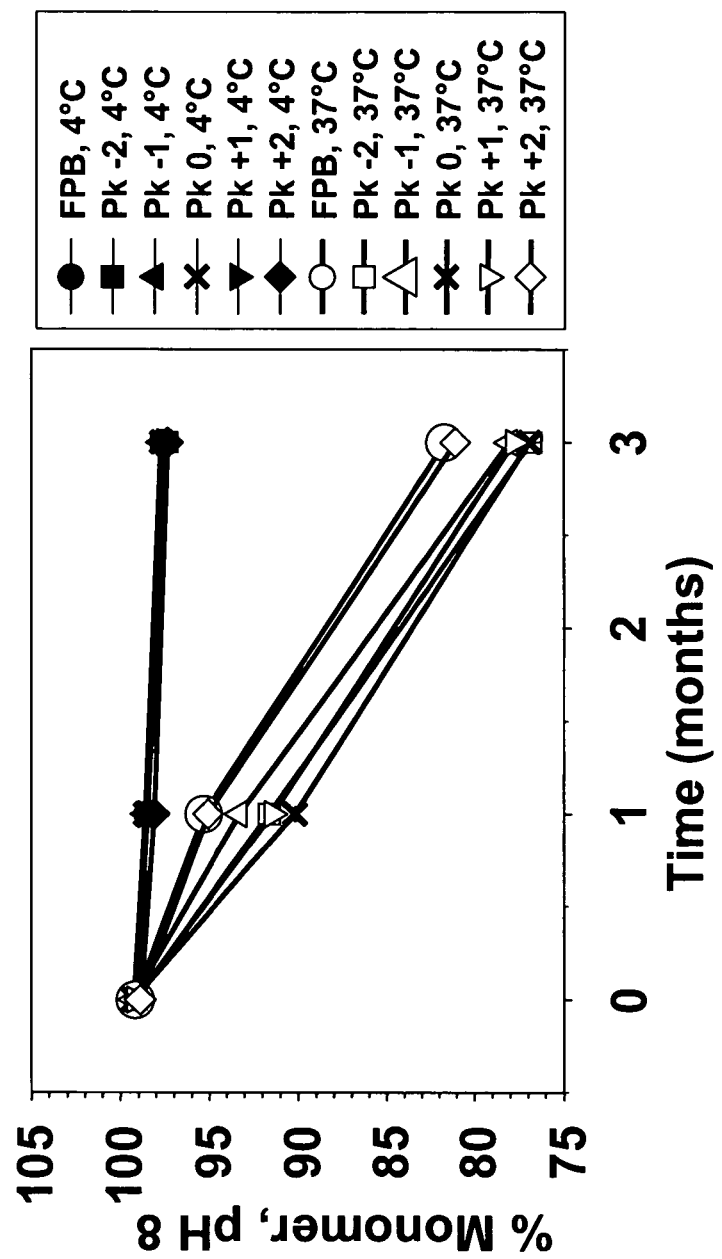

These experiments also revealed differences between the different isoforms and FPB, which were particularly evident in the 37° C. samples at pH 4 and 5. FPB was consistently among the samples having the highest amounts of monomer at all pHs. FIG. 4A-4E. At pH 4 and 5, FPB was more stable than any purified isoform, suggesting that a combination of isoforms stabilizes the mixture. FIG. 4A-4B. At pH 7 and 8, FPB is consistently as stable as the most stable purified isoform and more stable than isoforms −2, −1, +1, and 0, which together comprise about 85% of the total antibody contained in FPB. FIGS. 4D-4E. At pH 6, FPB and isoforms +2, +1, and 0 are approximately equally stable, and isoforms −1 and and −2 are slightly less stable. FIG. 4C. If each isoform in the mixture of isoforms in FPB had the same stability in FPB as it does in a purified form, FPB would be expected to have a stability between that of the least and most stable isoforms. This is not the case at any pH. Thus, these data may be interpreted to mean that the mixture of isoforms in FPB exerts a stabilizing influence.

Figure 5A:
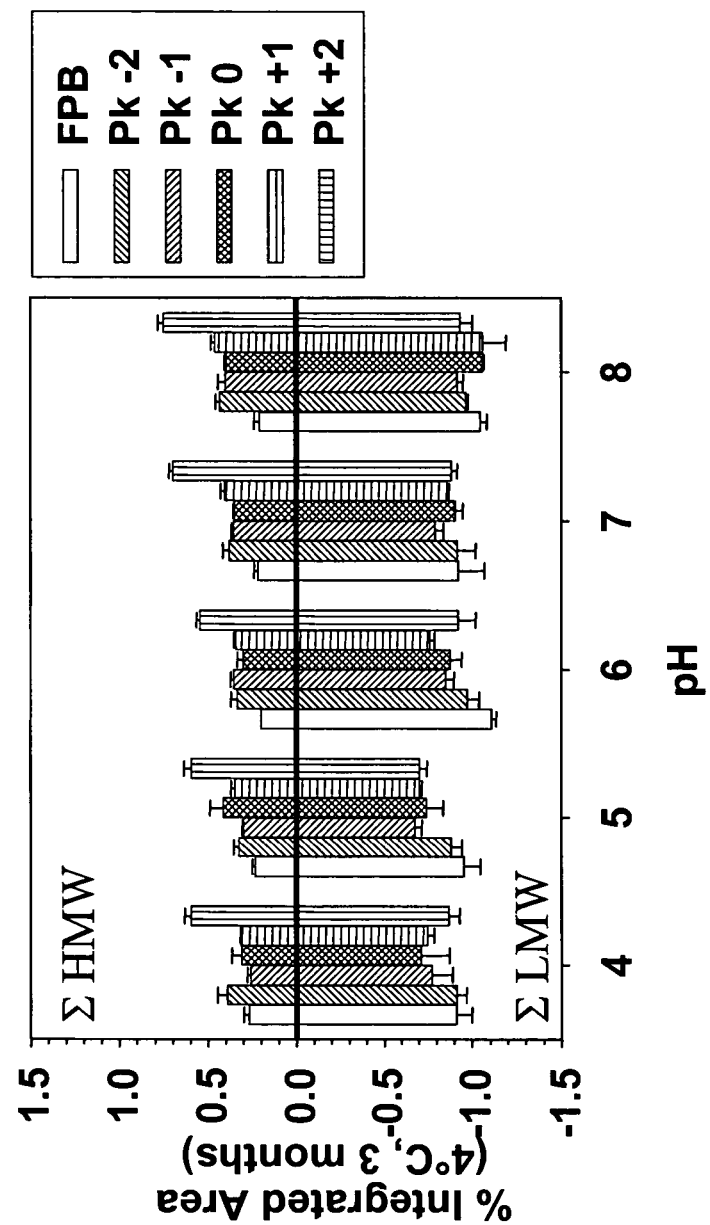
(FIG. 5A) and 37° C.
Figure 5B:
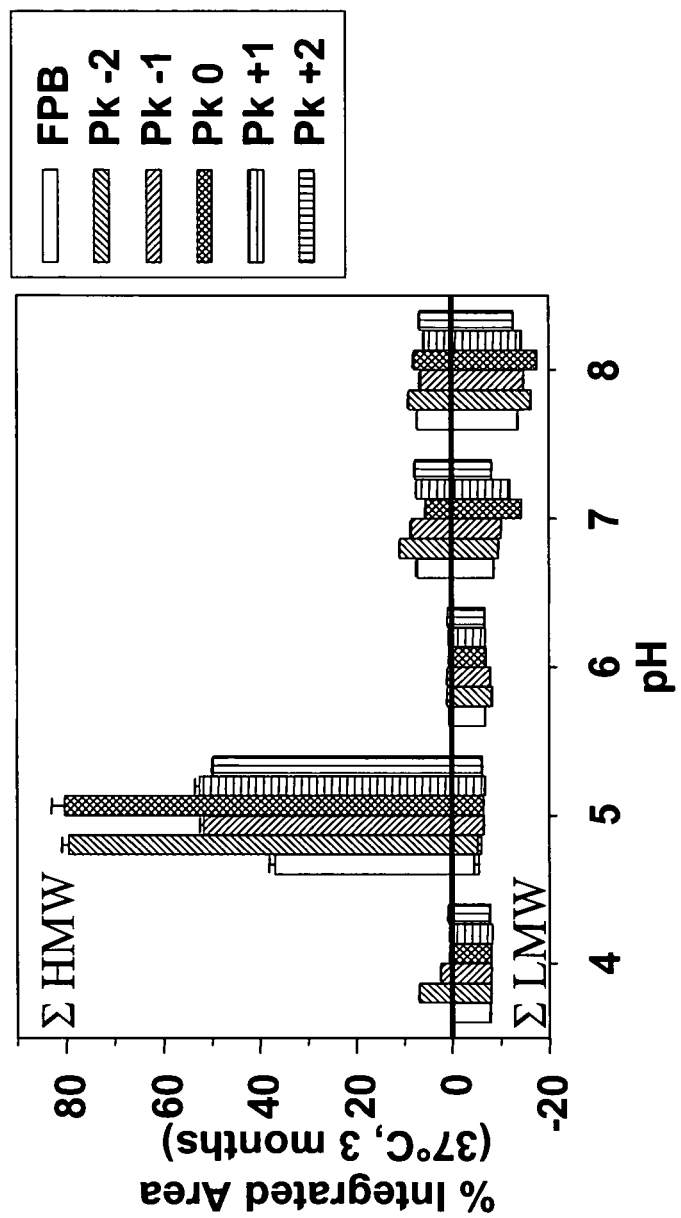
(FIG. 5B) at various pH's, as indicated. LMW and HMW species were detected by SEC. The samples were formulated as in FIG. 4.

FIG. 5 shows the percentage of the total area under the SEC column profile among samples incubated at 4° C. (FIG. 5A) and 37° C. (FIG. 5B) that is high molecular weight species (above the horizontal line, labeled Σ HMW), i.e. dimers and aggregates, and low molecular weight species (below the horizontal line, labeled Σ LMW), i.e., LMW1 and LMW2. Samples incubated at 4° C. at different pHs are similar. Nonetheless, FPB samples incubated at 4° C. consistently have lower levels of HMW species than other samples across all pHs, and isoform Peak +2 samples consistently have higher levels of HMW species than other samples. Samples incubated at 37° C. differ radically from each other, and pH 5 samples, particularly the isoform Peak 0 and −2 samples, contained a very substantial proportion of dimers and aggregates compared to samples incubated at other pHs. Samples incubated at pH 4, 7, and 8 contained a low percentage of HMW species, but pH 6 samples contained the lowest percentage of HMW species among the 37° C. samples. Further, pH 7 and 8 samples incubated at 37° C. have slightly higher amounts of LMW1 and LMW2 than 37° C. samples at other pHs. FIG. 5B.

Figure 6A:
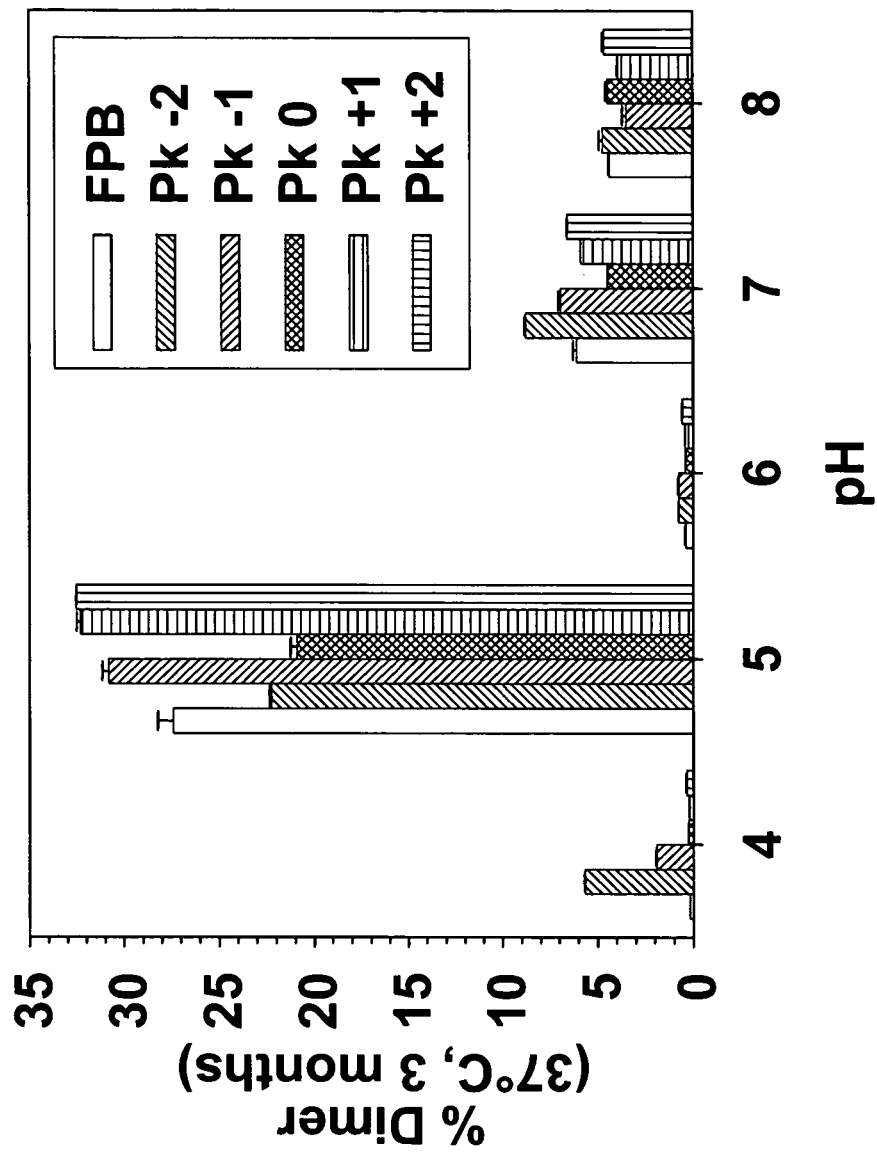
FIG. 6 shows the proportion of the total amount of antibody in material from purified isoform Peaks −2, −1, 0, +1, and +2 and FPB that was dimers (FIG. 6A) and aggregates (FIG. 6B)
Figure 6B:
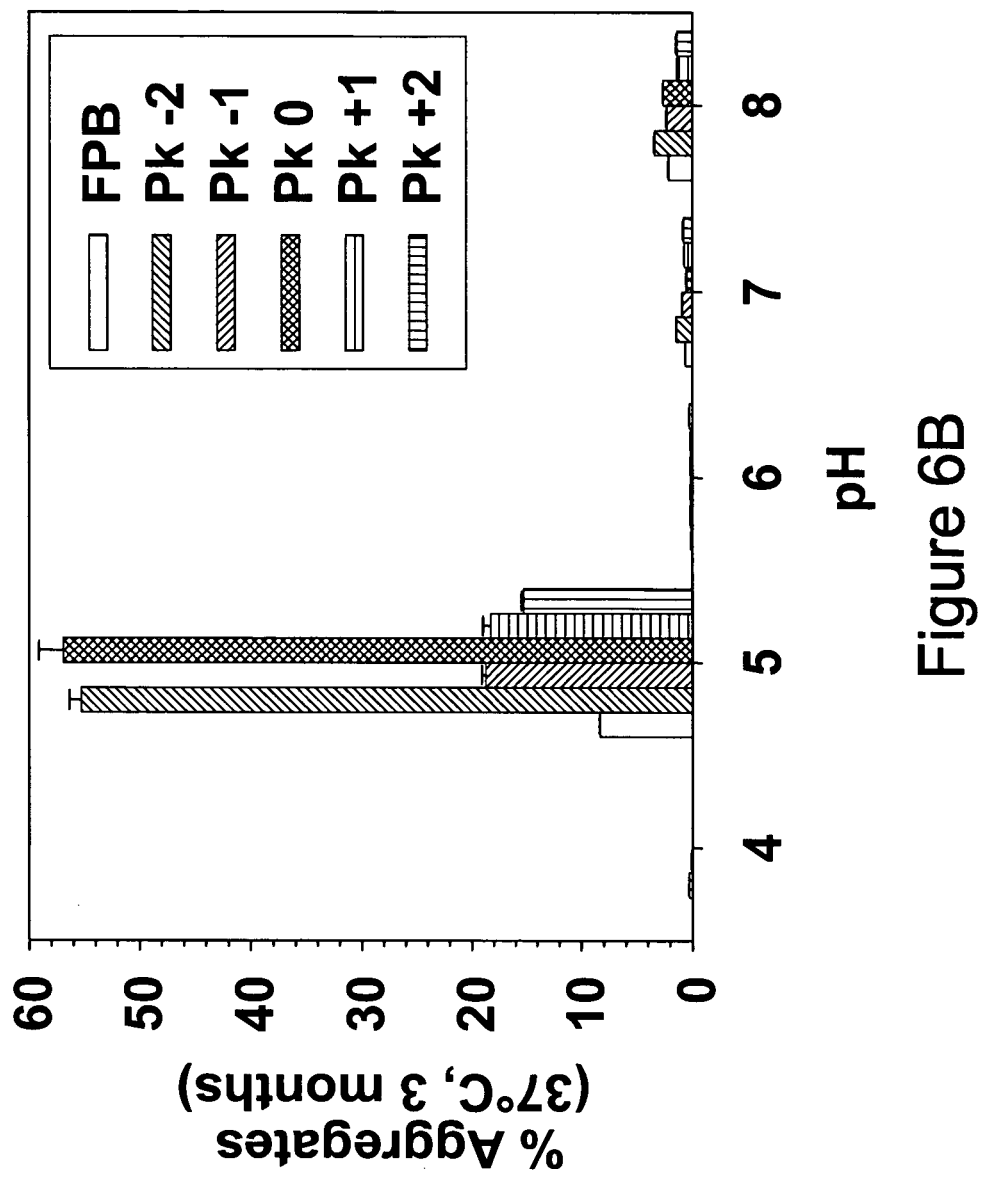

FIG. 6 shows the percentage of the total area under the SEC column profile among samples incubated at 37° C. that was dimers (FIG. 6A) or higher order aggregates (FIG. 6B). Samples incubated at pH 5 had a substantially higher percentage dimers and aggregates than samples incubated at other pHs. Among the pH 5 samples, the isoform Peak −2 and Peak 0 samples contained a higher percentage of aggregates than other samples. Samples incubated at pH 4, 7, and 8 contained a low percentage of aggregates and dimers, but pH 6 samples contained the lowest percentages of dimers and aggregates. Thus, the data in FIGS. 4-6 indicate that the pH 6 samples incubated at 37° C. contained less high molecular weight species than other 37° C. samples. Formation of aggregates is of particular concern in antibody formulations because aggregates are known to be immunogenic. Hermeling et al. (2004), Pharm. Res. 21(6): 897-903.

Reversed phase HPLC, performed on a Agilant Zorbax C-8 column, was used to further characterize changes in the formulated antibodies related to their hydrophobicity, properties that can be related to the folding of the antibody. In addition, reversed phase chromatography can detect the formation of hydrophilic or hydrophobic peptides that may form via cleavage of the antibody during storage. The reversed phase column was loaded in a 30:70 mixture of solutions B and A and eluted in a gradient that went from 30% solution B to 50% solution B. Solution A was 0.12% trifluoroacetic acid (TFA), and solution B was 60% isopropanol, 30% acetonitrile, 0.12% TFA. FIGS. 7A and 7B shows a group of reversed phase $OD_{215}$ column profiles from samples incubated for 3 months at 4° C. (FIG. 7A) and 37° C. (FIG. 7B) in 10 mM sodium phosphate, pH 8, 5% sorbitol. A small peak is observed early in the column profile of the 37° C. samples, which is presumably a small, hydrophilic peptide that is cleaved from the antibody. This peak does not occur in the 4° C. samples. The majority of the material at both temperatures migrates as a single peak, which is, however, broader in the 37° C. samples than in the 4° C. samples. FIG. 7.

FIG. 8 shows the percentage of the total area under the reversed phase column profiles of 37° C. samples at various indicated pHs that is a part of the main peak (FIG. 8A) or a part of the early-eluting, clipped species (FIG. 8B). More clipped species are observed at pH 8 than at any other pH tested. Samples at pH 5 to pH 7 have the lowest percentages of clipped species and the highest percentages of material in the main peak. Differences between the isoforms and FPB are largest at pH 8. Isoform Peaks −2 and 0, which yielded the most aggregate, also have the most hydrophilic clips at pH 8. FPB has less clips than isoform Peaks −2 and 0 but more than isoform Peaks −1, +1, and +2 at pH 8.

Changes in the tertiary and secondary structures of the samples at each time point were evaluated by fluorescence spectroscopy. Samples were diluted with their corresponding formulation buffer to a final concentration of 0.18 mg/mL. Intrinsic fluorescent measurements were obtained from a Photon Technology International dual-emission beam spectrofluorimeter operating in emission scan mode with sample chamber at 23° C. Emission scans were taken between 300 and 425 nm with excitation wavelength at 280 nm to assess fluorescence due to tyrosine and tryptophan residues. Emission scans were also taken with excitation wavelength at 293 nm to assess fluorescence due primarily to tryptophan residues.

The results indicated that the wavelength of maximal fluorescence emission was at 326 nm for all samples at the zero timepoint, for all 4° C. samples, and for 37° C. samples at pHs 6, 7, and 8 after 3 months storage. However, the wavelength of maximal fluorescence emission for 37° C. samples at pH 4 and 5 was 338 nm. Raw data not shown. These data are displayed in FIG. 9 as ratios between emission at 326 nm and 338 nm. The results indicate that the emission spectra have shifted in pH 4 and pH 5 samples incubated at 37° C. such that the 326 nm/338 nm ratio is about 1 or less, not clearly greater than 1 as in the pH 6, 7, or 8 samples at 37° C. The data indicate a change in the tertiary structure of the antibody in the pH 4 and 5 samples incubated at 37° C. Since the detected fluorescence is due to typtophan and tyrosine residue, the data also indicate greater exposure of these amino acids in the antibody samples at pH 4 and 5 incubated at 37° C.

Biological activity was assessed using an in vitro cell-based assay. This assay utilizes A549 lung cells. Proliferation of A549 cells can be inhibited by IFN-γ. The assay measures proliferation by staining the cells with ALAMARBLUE™ (AccuMed International, Inc., Chicago, Ill.). The concentration of antibody necessary to relieve the inhibition of proliferation by IFN-γ by half ($IC_{50}$) is indicated in Table 3. This assay is explained in more detail in US Patent Application No. 2005/0004353, which is incorporated herein by reference. Samples of purified isoforms and FPB stored for three months at pH 5 at the temperatures indicated in Table 3 were tested.

TABLE 3

| Sample (pH 5) | Storage temperature | $IC_{50}$ (µg/mL) |
|---|---|---|
| FPB | 4° C. | 0.0023 |
| Peak −2 | 4° C. | 0.0037 |
| Peak −1 | 4° C. | 0.0030 |
| Peak 0 | 4° C. | 0.0024 |
| Peak +1 | 4° C. | 0.0018 |
| Peak +2 | 4° C. | 0.0020 |
| FPB | 37° C. | 0.0027 |
| Peak −2 | 37° C. | 0.0038 |
| Peak −1 | 37° C. | 0.0033 |
| Peak 0 | 37° C. | 0.0033 |
| Peak +1 | 37° C. | 0.0028 |
| Peak +2 | 37° C. | 0.0032 |

These data indicate no clear relationship between the physical properties of the samples described above and biological activity as measured here. Given the substantial amounts of dimers and aggregates formed at 37° C. at pH 5, these data seem to suggest that the formation of dimers and aggregates does not affect biological function as measured here. However, in other experiments, it has been demonstrated that dilution can at least partially reverse the formation of the soluble aggregates and dimers present in the pH 5 samples. Data not shown. Since the samples are diluted to do this experiment, it is not possible to make any conclusions about the effects of aggregate and dimer formation on biological activity from this experiment. In summary, all samples are biologically active, at least that aspect of biological activity tested here. Immunogenicity of the samples is not assessed.

Taking the SEC, reversed phase, and fluorescence emission data together, the results suggest that the pH 6 storage conditions preserve the structure of the antibody better than other conditions tested. In particular, the fluorescence emission data indicate that the pH 6, 7, and 8 conditions were comparable and superior to the pH 4 and 5 conditions. The reversed phase data indicated that the pH 5, 6, and 7 conditions were comparable and superior to conditions at pH 4 and 8. Finally, the SEC data indicated that the pH 6 conditions were the most favorable for FPB and all individual isoforms at 37° C., followed by the pH 4, 7, and 8 conditions. In the pH 5 conditions, a large proportion of aggregates and dimers were observed at 37° C. A measurement of the pH of FPB samples in each of the formulations described here after almost 2 years at 4° C. showed that the pH was unchanged for each of the formulations. Samples that were formulated at pH 6, 7, and 8 and incubated at 37° C. for 3 months and thereafter stored at 4° C. for almost 21 months also had unchanged pH, while similarly treated samples formulated at pH 4 and 5 underwent an increase of almost one pH unit. Data not shown. The increase in pH of the samples formulated at pH 4 and 5 may be due to protein degradation and/or some property of the particular lot of the buffering agent used.

The data also show the FPB is as stable or more stable than the most stable individual isoform in each of the conditions tested. See FIGS. 4A-4E. If the individual isoforms had identical stability when incubated in isolation and as a constituent of FPB, then it would be expected that FPB would be interemediate in stability between the most and least stable isoforms. The fact that this is not the case suggests that a combination of isoforms may stabilize a composition.

Example 3

Formulations Using Various Buffers at a Range of pHs with and without Sorbitol

The following experiment was done to distinguish between the effects of the pH and the effects of the particular buffering agent used on the stability of a composition containing FPB, which, as described above, contains the various isoforms of the antibody described in Example 1. In addition, samples with and without sorbitol were compared to determine the effect of sorbitol on stability. Each sample was formulated at a final concentration of approximately 1 mg/mL at target pHs of 4, 5, 6, 7, or 8 in 10 mM sodium citrate, potassium phosphate, sodium phosphate, sodium acetate, or histidine. The formulation solutions were made up with all components other than the antibody at final concentrations and with the pH as close to the target pH as possible. The antibody preparation was diluted approximately 29 fold from a concentrated solution directly into the formulation solution, which, in some cases changed the pH substantially. This was not surprising because some pHs tested were not within the buffering range of some of the buffering agents. Table 4 describes the samples and gives the actual pHs of the final formulations after addition of the antibody. Protein concentration of each complete formulation was determined by measuring optical density at 280 nanometers ($OD_{280}$) using a NANODROP™ spectrophotometer (NanoDrop Technologies, Wilmington, Del., USA) and calculating protein concentration using an extinction coefficient of 1.5 µg/mL/$OD_{280}$.

Samples were incubated under static conditions at 4° C. or 37° C. All formulated antibody solutions and corresponding placebos, i.e., formulated solutions lacking antibodies, were sterilized by filtration through 0.2 µm membranes prior to aliquoting into sterile microtubes with o-ring caps, which were used to prevent evaporation. The total volume for each sample was about 650 µL.

TABLE 4

Sample Descriptions

| Sample Designation | Buffer | Sorbitol Concentration (%) | Actual pH | Protein Concentration (mg/mL) |
|---|---|---|---|---|
| NaC4 | Sodium Citrate | 0 | 4.10 | 1.02 |
| NaC4S | Sodium Citrate | 5 | 4.02 | 0.99 |
| NaC5 | Sodium Citrate | 0 | 5.01 | 1.02 |
| NaC5S | Sodium Citrate | 5 | 4.99 | 1.05 |
| NaC6 | Sodium Citrate | 0 | 6.00 | 1.02 |
| NaC6S | Sodium Citrate | 5 | 5.99 | 1.02 |
| NaC7 | Sodium Citrate | 0 | 6.90 | 1.04 |
| NaC7S | Sodium Citrate | 5 | 6.86 | 1.01 |
| NaC8 | Sodium Citrate | 0 | 7.38 | 1.02 |
| NaC8S | Sodium Citrate | 5 | 7.29 | 1.09 |
| KP4 | Potassium Phosphate | 0 | 4.69 | 1.08 |
| KP4S | Potassium Phosphate | 5 | 4.66 | 1.03 |
| KP5 | Potassium Phosphate | 0 | 5.23 | 1.07 |
| KP5S | Potassium Phosphate | 5 | 5.12 | 1.03 |
| KP6 | Potassium Phosphate | 0 | 5.92 | 1.06 |
| KP6S | Potassium Phosphate | 5 | 5.89 | 1.03 |
| KP7 | Potassium Phosphate | 0 | 6.96 | 1.05 |
| KP7S | Potassium Phosphate | 5 | 6.91 | 1.02 |
| KP8 | Potassium Phosphate | 0 | 7.79 | 0.97 |
| KP8S | Potassium Phosphate | 5 | 7.77 | 1.04 |
| NaP4 | Sodium Phosphate | 0 | 4.84 | 1.02 |
| NaP4S | Sodium Phosphate | 5 | 4.73 | 1.02 |
| NaP5 | Sodium Phosphate | 0 | 5.22 | 1.02 |
| NaP5S | Sodium Phosphate | 5 | 5.12 | 1.06 |
| NaP6 | Sodium Phosphate | 0 | 6.04 | 1.07 |
| NaP6S | Sodium Phosphate | 5 | 5.92 | 1.04 |
| NaP7 | Sodium Phosphate | 0 | 7.05 | 1.03 |
| NaP7S | Sodium Phosphate | 5 | 6.94 | 1.04 |
| NaP8 | Sodium Phosphate | 0 | 7.92 | 1.04 |
| NaP8S | Sodium Phosphate | 5 | 7.78 | 1.03 |
| A4 | Sodium Acetate | 0 | 4.18 | 1.07 |
| A4S | Sodium Acetate | 5 | 4.13 | 1.02 |
| A5 | Sodium Acetate | 0 | 5.04 | 1.03 |
| A5S | Sodium Acetate | 5 | 4.97 | 1.06 |
| A6 | Sodium Acetate | 0 | 5.98 | 1.07 |
| A6S | Sodium Acetate | 5 | 5.9 | 1.03 |
| A7 | Sodium Acetate | 0 | 6.45 | 1.05 |
| A7S | Sodium Acetate | 5 | 6.41 | 1.01 |
| A8 | Sodium Acetate | 0 | 6.53 | 1.01 |
| A8S | Sodium Acetate | 5 | 6.49 | 1.07 |
| H4 | Histidine | 0 | 4.65 | 1.05 |
| H4S | Histidine | 5 | 4.59 | 1.04 |
| H5 | Histidine | 0 | 5.18 | 1.05 |
| H5S | Histidine | 5 | 5.03 | 1.06 |
| H6 | Histidine | 0 | 6.07 | 1.03 |
| H6S | Histidine | 5 | 5.98 | 1.03 |
| H7 | Histidine | 0 | 7.00 | 1.02 |
| H7S | Histidine | 5 | 6.85 | 1.05 |
| H8 | Histidine | 0 | 7.86 | 1.02 |
| H8S | Histidine | 5 | 7.64 | 1.02 |

Stability was assessed after 0, 4, 8, and 12 weeks of storage using SEC, as explained in Example 2. FIG. 13 shows the percent monomer as measured by SEC at the zero time point with (left panel) and without (right panel) sorbitol. In FIG. 13 and the following figures, the pH listed is the target pH, which is somewhat different from the actual pH (which is listed in Table 4) in some cases, as explained above. Data points where the pH of the formulation deviates substantially from the target pH (other than the target pH 4, which are all included) are omitted from the figures. All formulations, with and without sorbitol, had comparable percent monomer (of approximately 98%) at time zero. FIG. 13. FIG. 14 shows the percent monomer after 12 weeks at 37° C. in the presence (left panel) and absence (right panel) of sorbitol. Samples at a target pH of 4 generally had about 95% monomer or less, as did sodium citrate samples at a target pH of 5 and sodium phosphate and potassium phosphate samples at target pHs of 7 and 8 and histidine samples without sorbitol at target pH 8. Data for samples with and without sorbitol was generally comparable, although sorbitol did show a protective effect in a few instances. After 12 weeks at 37° C., the best samples in histidine, sodium acetate, and sodium citrate plus sorbitol had close to 97% monomer, whereas the best samples in sodium or potassium phosphate plus sorbitol had slightly lower percent monomer. FIG. 14. Samples with sorbitol plus any one of the buffering agents tested incubated at 4° C. showed essentially no change in percent monomer after 12 weeks. Data not shown.

For samples containing histidine or sodium acetate, with or without sorbitol, pH 6 samples had the highest percent monomer among all samples in the same buffering agent after 12 weeks at 37° C. FIGS. 15 and 16. The same was true for samples containing potassium phosphate with sorbitol. FIG. 18. In the remaining samples (sodium citrate and sodium phosphate with and without sorbitol and potassium phosphate without sorbitol) the pH 6 sample was one of two samples with the highest, and approximately equal, percent monomer after 12 weeks at 37° C. FIGS. 17-19. Thus, pH 6 was either the best pH or one of the best two pHs for stabilizing the antibody, regardless of the buffering agent used.

FIG. 20 shows the percent monomer for all buffering agents and pHs tested, with and without sorbitol after 12 weeks at 37° C. It indicates that the stability of the antibody is much more dependent on the buffering agent used at pHs other than about pH 6, since the percent monomer for all buffers tested was very close at pH 6, but not at other pHs. It also illustrates the protective effect of sorbitol, particularly in samples at pH 8. However, different buffering agents were effective over different pH ranges. For example, sodium phosphate and potassium phosphate were most effective at target pH 5 and 6, but had much lower percent monomer at target pH 7 and 8 than did histidine and citrate. Histidine was effective at target pH 5-7, although it was best at target pH 6. Sodium acetate performed well at target pH 5-6, and sodium citrate was most effective at target pH 6-7. Also, sodium citrate had very low percent monomer at target pH 4 compared to other buffering agents, which may reflect the fact that the actual pH of the sodium citrate sample was closer to pH 4 (and more acidic) than that of any other samples with at target pH 4. Sodium citrate also had the lowest percent monomer of all buffers tested at pH 5, even though all agents tested had a pH within, at most, 0.23 pH units of pH 5.

FIG. 21 shows the percent of low molecular weight species (LMW 1 and LMW 2) as determined by SEC (as explained in Example 2) for samples with and without sorbitol. When viewed in conjunction with FIG. 20, FIG. 21 indicates that most of the loss of monomers is due to the formation of low molecular weight species in samples with and without sorbitol.

FIG. 22 show the percent of the total sample that was dimers as measured by SEC after 12 weeks static incubation at 37° C. Samples incubated at pH 7 or 8 had a higher percent dimer, particularly samples in sodium or potassium phosphate. Sorbitol had a slight protective effect on histidine samples at pH 8. Thus, dimer formation accounts for some of the decrease in percent monomer seen in samples in sodium or potassium phosphate at pH 7 or 8.

Taken together, these data indicate that the antibody is relatively stable at about pH 6 in a variety of buffering agents. Sorbitol has a stabilizing effect under some conditions. Most of the loss in percent monomer in samples incubated at 37° C. was due to the formation of low molecular weight species, although dimer formation also contributed in some samples at pH 7 and 8. A measurement of the pH of all samples, with and without sorbitol, after storage at 37° C. for 12 weeks showed no change in pH from that measured at time zero. Data not shown.

Example 4

Testing Mixtures of Purified Isoforms for Stability

Different purified isoforms (described in Example 1) were shown in Example 2 to have different stabilities, and FPB (which contains all isoforms) was generally as stable as the most stable of the purified isoforms. A possible explanation of this observation is that some element present in FPB samples is removed during isolation of the individual isoforms. If this were true, then one would expect a mixture of isoforms in approximately the same ratio as found in FPB (like the IsoBulk mixture described in Table 5 below) to be less stable than FPB.

In the experiment described below, various combinations of purified isoforms were tested for stability. In addition, mixtures of isoforms −2, −1, 0, 1, and 2 in approximately the same ratios as they occur in FPB (called IsoBulk) were tested to determine whether such mixtures would behave like FPB. FPB contains minor amounts three species, i.e., 3, 4, and −3, in addition to those used to make IsoBulk. See FIG. 2. Table 5 describes the samples.

TABLE 5

Description of the samples

| Sample Designation | Isoforms | Mass Ratio | Formulation | Protein concentration (mg/mL) |
|---|---|---|---|---|
| A5S (0, 1) | 0, 1 | 1:1 | 5% sorbitol, 10 mM sodium acetate pH 5 | 1.05 |
| A5S (0, −1) | 0, −1 | 1:1 | 5% sorbitol, 10 mM sodium acetate pH 5 | 1.06 |
| A5S (1, −1) | 1, −1 | 1:1 | 5% sorbitol, 10 mM sodium acetate pH 5 | 1.05 |
| A5S (−1, −2, −3) | −1, −2, −3 | 1:1:1 | 5% sorbitol, 10 mM sodium acetate pH 5 | 1.08 |
| A5S (1, 2, 3, 4) | 1, 2, 3, 4 | 1:1:1:1 | 5% sorbitol, 10 mM sodium acetate pH 5 | 1.05 |
| A5S (2, −2) | 2, −2 | 1:1 | 5% sorbitol, 10 mM sodium acetate pH 5 | 1.05 |
| H6S (0, 1) | 0, 1 | 1:1 | 5% sorbitol, 10 mM histidine pH 6 | 1.05 |

TABLE 5-continued

Description of the samples

| Sample Designation | Isoforms | Mass Ratio | Formulation | Protein concentration (mg/mL) |
|---|---|---|---|---|
| H6S (0, −1) | 0, −1 | 1:1 | 5% sorbitol, 10 mM histidine pH 6 | 1.07 |
| H6S (1, −1) | 1, −1 | 1:1 | 5% sorbitol, 10 mM histidine pH 6 | 1.07 |
| H6S (−1, −2, −3) | −1, −2, −3 | 1:1:1 | 5% sorbitol, 10 mM histidine pH 6 | 1.02 |
| A4S (IsoBulk) | −2, −1, 0, 1, 2 | 1.0:1.9:3.6:2.3:1.0 | 5% sorbitol, 10 mM sodium acetate pH 4 | 1.01 |
| A5S (IsoBulk) | −2, −1, 0, 1, 2 | 1.0:1.9:3.5:2.1:1.0 | 5% sorbitol, 10 mM sodium acetate pH 5 | 1.01 |
| H6S (IsoBulk) | −2, −1, 0, 1, 2 | 1.2:2.2:4.4:2.7:1.0 | 5% sorbitol, 10 mM histidine pH 6 | 1.02 |
| NaP7S (IsoBulk) | −2, −1, 0, 1, 2 | 1.0:1.9:3.6:2.3:1.0 | 5% sorbitol, 10 mM sodium phosphate pH 7 | 1.02 |
| NaP8S (IsoBulk) | −2, −1, 0, 1, 2 | 1.0:1.9:3.6:2.3:1.0 | 5% sorbitol, 10 mM sodium phosphate pH 8 | 1.01 |

FIG. 23 shows a comparison of FPB (left panel) with IsoBulk (right panel) at pH 4 to 8 in formulations comprising 5% sorbitol plus a buffering agent with good buffering capacity at the selected pH after 12 weeks incubation at 4° C. or 37° C. Percent monomer was determined by SEC as explained in Example 2. Sodium acetate was the buffering agent used at pH 4 and 5, histidine was used at pH 6, and sodium phosphate was used at pH 7 and 8. Both FPB and IsoBulk samples incubated at 4° C. (FIG. 23, closed circles) were substantially the same as samples at the zero timepoint. Data not shown. All IsoBulk samples incubated at 4° C. had a slightly lower percent monomer (about 98%) compared to that observed for FPB samples incubated at 4° C. (about 99%). The FPB samples incubated at 37° C. had slightly higher percent monomer than IsoBulk samples at pH 4, 5, and 6 and a noticeably higher percent monomer at pH 7 and 8. The differences between the starting percent monomer and the percent monomer after 12 weeks at 37° C. at pH 4, 5, or 6 for FPB versus IsoBulk were approximately the same. Thus, FPB and IsoBulk are approximately equally stable at pH 4, 5, or 6. The data also indicates that IsoBulk is less stable than FPB at pH 7 and 8. Thus, at least at pH 4-6, the results observed in FIG. 4 cannot be explained by the elimination of a stabilizing element in FPB during purification of the isoforms. Such an explanation could potentially account for the decreased stability of IsoBulk compared to FPB at pH 7 and 8.

FIGS. 24 and 25 show the net percent monomer loss as determined by SEC (as described above) of individual samples containing purified isoforms or mixtures of isoforms after eight weeks of static incubation at 31° C. The samples were formulated in either 5% sorbitol, 10 mM sodium acetate at pH 5 (FIG. 24) or in 5% sorbitol, 10 mM histidine at pH 6 (FIG. 25). Samples containing single, purified isoforms had the greatest losses in percent monomer, followed by samples containing mixtures of two purified isoforms. This was true in both formulations tested. FIGS. 24 and 25. Samples containing mixtures of three or more isoforms had comparable loss in percent monomer, which was generally lower than that observed for single isoforms or mixtures of two isoforms. One mixture of two tested (isoforms 2 and −2) was comparable to the mixtures of 3 or more isoforms. These data indicate that mixtures containing three or more isoforms are stabilized compared to mixtures containing fewer isoforms.

What is claimed is:

1. A stable pharmaceutical composition comprising a purified preparation of a monoclonal antibody and a buffering agent,
wherein the composition is at a pH from 5.7 to 6.5,
wherein the buffering agent is histidine, acetate, phosphate, or citrate or a salt thereof,
wherein the purified preparation comprises the isoforms represented by peaks −2, −1, 0, 1, and 2 shown in FIG. 2,
wherein the antibody comprises a heavy chain comprising the amino acid sequence of SEQ ID NO:17 and a light chain comprising the amino acid sequence of SEQ ID NO:18, and
wherein the antibody is produced by a CHO cell.

2. The pharmaceutical composition of claim 1, wherein the buffering agent is acetate or a salt thereof.

3. The pharmaceutical composition of claim 1, wherein the buffering agent is histidine, sodium acetate, sodium phosphate, potassium phosphate, or sodium citrate.

4. The pharmaceutical composition of claim 1, wherein the composition further comprises a sugar, a carbohydrate, and/or a salt.

5. The pharmaceutical composition of claim 4, wherein the composition comprises sorbitol.

6. The pharmaceutical composition of claim 1, wherein the buffer is citrate or a salt thereof.

7. The pharmaceutical composition of claim 1, wherein the composition is at a pH from 5.7 to 6.3.

8. A stable pharmaceutical composition comprising a purified preparation of a monoclonal antibody and a buffering agent,
wherein the composition is at a pH from 5.7 to 6.5,
wherein the purified preparation comprises the isoforms represented by peaks −2, −1, 0, 1, and 2 shown in FIG. 2,
wherein the buffering agent is histidine or a salt thereof,
wherein the antibody comprises a heavy chain comprising the amino acid sequence of SEQ ID NO:17 and a light chain comprising the amino acid sequence of SEQ ID NO:18, and
wherein the antibody is produced by a CHO cell.

9. The pharmaceutical composition of claim 8, wherein the pH is from 5.7 to 6.3.

10. The pharmaceutical composition of claim 9, wherein the composition further comprises sorbitol.

11. A stable pharmaceutical composition comprising a purified preparation of a monoclonal antibody and a buffering agent,
wherein the composition is at a pH from 5.7 to 6.5,
wherein the purified preparation comprises the isoforms represented by peaks −2, −1, 0, 1, and 2 shown in FIG. 2,
wherein the antibody comprises a heavy chain comprising the amino acid sequence of SEQ ID NO:17 and a light chain comprising the amino acid sequence of SEQ ID NO:18, and
wherein the antibody is produced by a CHO cell.

12. The pharmaceutical composition of claim 11, wherein the buffering agent is histidine, acetate, phosphate, or citrate or a salt thereof.

13. The pharmaceutical composition of claim 11, wherein the composition is at a pH from 5.7 to 6.3.

14. A stable pharmaceutical composition comprising a purified preparation of a monoclonal antibody and a buffering agent,
wherein the composition is at a pH from 5.7 to 6.5,
wherein the buffering agent is acetate or a salt thereof,
wherein the purified preparation comprises the isoforms represented by peaks −2, −1, 0, 1, and 2 shown in FIG. 2,
wherein the antibody comprises the amino acid sequences of SEQ ID NO:17 and SEQ ID NO:18, and
wherein the antibody is produced in CHO cells.

15. The pharmaceutical composition of claim 14, wherein the buffering agent is sodium acetate or potassium acetate.

16. The pharmaceutical composition of claim 15, wherein the composition comprises sorbitol.

17. The pharmaceutical composition of claim 14, wherein the composition is at a pH from 5.7 to 6.3.

18. The pharmaceutical composition of claim 15, wherein the buffering agent is sodium acetate.

19. A stable pharmaceutical composition comprising a purified preparation of a monoclonal antibody and a buffering agent,
wherein the buffering agent is citrate or a salt thereof,
wherein the composition is at a pH from 5.7 to 6.5, and
wherein the purified preparation comprises the isoforms represented by peaks −2, −1, 0, 1, and 2 shown in FIG. 2, and
wherein the antibody comprises the amino acid sequences of SEQ ID NO:17 and SEQ ID NO:18.

20. The pharmaceutical composition of claim 19, wherein the buffering agent is sodium citrate and wherein the composition is at a pH from 5.7 to 6.3.

21. The pharmaceutical composition of claim 19, wherein the composition comprises sorbitol.

22. The pharmaceutical composition of claim 1, wherein the buffering agent is potassium citrate.

23. The pharmaceutical composition of claim 22, further comprising sorbitol.

24. The pharmaceutical composition of claim 3, wherein the buffering agent is sodium phosphate.

25. The pharmaceutical composition of claim 24, further comprising sorbitol.

26. The pharmaceutical composition of claim 3, wherein the buffering agent is sodium citrate.

27. The pharmaceutical composition of claim 26, further comprising sorbitol.

28. The pharmaceutical composition of claim 3, wherein the buffering agent is potassium phosphate.

29. The pharmaceutical composition of claim 28, further comprising sorbitol.

* * * * *